(12) United States Patent
Rosen et al.

(10) Patent No.: US 10,588,739 B2
(45) Date of Patent: Mar. 17, 2020

(54) OPHTHALMIC DEVICES, SYSTEM AND METHODS THAT IMPROVE PERIPHERAL VISION

(71) Applicant: AMO GRONINGEN B.V., Groningen (NL)

(72) Inventors: Robert Rosen, Groningen (NL); Hendrik A. Weeber, Groningen (NL); Carmen Canovas Vidal, Groningen (NL); Marrie H. Van Der Mooren, Groningen (NL); Mihai State, Groningen (NL); Patricia Ann Piers, Groningen (NL); Aixa Alarcon Heredia, Groningen (NL)

(73) Assignee: AMO GRONINGEN B.V., Groningen (NL)

(*) Notice: Subject to any disclaimer, the term of this patent is extended or adjusted under 35 U.S.C. 154(b) by 0 days.

(21) Appl. No.: 16/025,958

(22) Filed: Jul. 2, 2018

(65) Prior Publication Data
US 2018/0318065 A1    Nov. 8, 2018

Related U.S. Application Data

(62) Division of application No. 14/692,609, filed on Apr. 21, 2015, now Pat. No. 10,010,407.
(Continued)

(51) Int. Cl.
*A61F 2/16* (2006.01)

(52) U.S. Cl.
CPC ............ *A61F 2/164* (2015.04); *A61F 2/1613* (2013.01); *A61F 2/1618* (2013.01); *A61F 2/1648* (2013.01)

(58) Field of Classification Search
CPC ...... A61F 2/164; A61F 2/1613; A61F 2/1618; A61F 2/1637; A61F 2/1656;
(Continued)

(56) References Cited

U.S. PATENT DOCUMENTS

| 3,367,734 A | 2/1968 | Bystricky et al. |
| 4,581,031 A | 4/1986 | Koziol et al. |

(Continued)

FOREIGN PATENT DOCUMENTS

| EP | 0343067 A1 | 11/1989 |
| EP | 0457553 A2 | 11/1991 |

(Continued)

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.
(Continued)

*Primary Examiner* — Paul B Prebilic
(74) *Attorney, Agent, or Firm* — Johnson & Johnson Surgical Vision, Inc.

(57) ABSTRACT

The present disclosure relates to devices, systems, and methods for improving or optimizing peripheral vision. In particular, methods are disclosed which include utilizing particular characteristics of the retina in improving or optimizing peripheral vision. Additionally, various IOL designs, as well as IOL implantation locations, are disclosed which improve or optimize peripheral vision.

14 Claims, 44 Drawing Sheets

Related U.S. Application Data

(60) Provisional application No. 62/038,667, filed on Aug. 18, 2014, provisional application No. 61/982,135, filed on Apr. 21, 2014.

(58) Field of Classification Search
CPC ........ A61F 2240/002; A61F 2250/0053; A61F 2250/0091
See application file for complete search history.

(56) References Cited

U.S. PATENT DOCUMENTS

| | | | |
|---|---|---|---|
| 4,592,630 A * | 6/1986 | Okazaki | G02C 7/061 351/159.42 |
| 4,624,538 A | 11/1986 | MacFarlane | |
| 4,637,697 A | 1/1987 | Freeman | |
| 4,642,112 A | 2/1987 | Freeman | |
| 4,648,878 A | 3/1987 | Kelman | |
| 4,655,565 A | 4/1987 | Freeman | |
| 4,666,446 A | 5/1987 | Koziol et al. | |
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,828,558 A | 5/1989 | Kelman | |
| 4,932,970 A | 6/1990 | Portney | |
| 4,995,714 A | 2/1991 | Cohen | |
| 4,995,715 A | 2/1991 | Cohen | |
| 5,016,977 A | 5/1991 | Baude et al. | |
| 5,056,908 A | 10/1991 | Cohen | |
| 5,066,301 A | 11/1991 | Wiley | |
| 5,089,023 A | 2/1992 | Swanson | |
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,144,483 A | 9/1992 | Cohen | |
| 5,225,858 A | 7/1993 | Portney | |
| 5,229,797 A | 7/1993 | Futhey et al. | |
| 5,354,334 A | 10/1994 | Fedorov et al. | |
| 5,549,669 A | 8/1996 | Jansen | |
| 5,652,638 A | 7/1997 | Roffman et al. | |
| 5,683,457 A | 11/1997 | Gupta et al. | |
| 5,699,142 A | 12/1997 | Lee et al. | |
| 5,728,156 A | 3/1998 | Gupta et al. | |
| 5,748,282 A | 5/1998 | Freeman | |
| 5,760,871 A | 6/1998 | Kosoburd et al. | |
| 5,777,719 A | 7/1998 | Williams et al. | |
| 5,796,462 A | 8/1998 | Roffman et al. | |
| 5,968,094 A | 10/1999 | Werblin et al. | |
| 6,126,283 A | 10/2000 | Wen et al. | |
| 6,126,286 A | 10/2000 | Portney | |
| 6,142,625 A | 11/2000 | Sawano et al. | |
| 6,183,084 B1 | 2/2001 | Chipman et al. | |
| 6,197,057 B1 | 3/2001 | Peyman et al. | |
| 6,210,005 B1 | 4/2001 | Portney | |
| 6,338,559 B1 | 1/2002 | Williams et al. | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,533,814 B1 | 3/2003 | Jansen | |
| 6,536,899 B1 | 3/2003 | Fiala | |
| 6,537,317 B1 | 3/2003 | Steinert et al. | |
| 6,547,822 B1 | 4/2003 | Lang | |
| 6,554,859 B1 | 4/2003 | Lang et al. | |
| 6,557,992 B1 | 5/2003 | Dwyer et al. | |
| 6,609,793 B2 | 8/2003 | Norrby et al. | |
| 6,705,729 B2 | 3/2004 | Piers et al. | |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,851,803 B2 | 2/2005 | Wooley et al. | |
| 6,913,620 B2 | 7/2005 | Lipshitz | |
| 6,923,539 B2 | 8/2005 | Simpson et al. | |
| 6,923,540 B2 | 8/2005 | Ye et al. | |
| 6,986,578 B2 | 1/2006 | Jones | |
| 7,025,456 B2 | 4/2006 | Morris et al. | |
| 7,025,460 B2 | 4/2006 | Smith, III | |
| 7,036,931 B2 | 5/2006 | Lindacher et al. | |
| 7,048,760 B2 | 5/2006 | Cumming | |
| 7,061,693 B2 | 6/2006 | Zalevsky | |
| 7,073,906 B1 | 7/2006 | Portney | |
| 7,137,702 B2 | 11/2006 | Piers et al. | |
| 7,156,516 B2 | 1/2007 | Morris et al. | |
| 7,186,266 B2 | 3/2007 | Peyman | |
| 7,188,949 B2 | 3/2007 | Bandhauer et al. | |
| 7,238,201 B2 | 7/2007 | Portney et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,410,500 B2 | 8/2008 | Claoue | |
| 7,441,894 B2 | 10/2008 | Zhang et al. | |
| 7,475,986 B2 | 1/2009 | Dai et al. | |
| 7,503,655 B2 | 3/2009 | Smith, III | |
| 7,615,073 B2 | 11/2009 | Deacon et al. | |
| 7,665,842 B2 | 2/2010 | Ho et al. | |
| 7,766,482 B2 | 8/2010 | Smith, III et al. | |
| 7,871,162 B2 | 1/2011 | Weeber | |
| 7,997,727 B2 | 8/2011 | Ho et al. | |
| 8,057,034 B2 | 11/2011 | Ho et al. | |
| 8,062,361 B2 | 11/2011 | Nguyen et al. | |
| 8,201,943 B2 | 6/2012 | Hammer et al. | |
| 8,206,442 B2 | 6/2012 | Sel et al. | |
| 8,262,728 B2 | 9/2012 | Zhang et al. | |
| 8,382,832 B2 | 2/2013 | Deacon et al. | |
| 8,430,508 B2 | 4/2013 | Weeber | |
| 8,540,365 B2 | 9/2013 | Varnas | |
| 8,862,447 B2 | 10/2014 | Weeber | |
| 9,345,570 B2 | 5/2016 | Sieber et al. | |
| 2002/0044255 A1 | 4/2002 | Ye | |
| 2002/0101564 A1 | 8/2002 | Herrick | |
| 2002/0118337 A1 | 8/2002 | Perrott et al. | |
| 2002/0176049 A1 | 11/2002 | Sakai et al. | |
| 2003/0076478 A1 | 4/2003 | Cox | |
| 2003/0171808 A1 | 9/2003 | Phillips | |
| 2004/0085515 A1 | 5/2004 | Roffman et al. | |
| 2004/0106992 A1 | 6/2004 | Lang et al. | |
| 2004/0111153 A1 | 6/2004 | Woods et al. | |
| 2004/0156014 A1 | 8/2004 | Piers et al. | |
| 2005/0043794 A1 | 2/2005 | Geraghty et al. | |
| 2005/0096226 A1 | 5/2005 | Stock et al. | |
| 2005/0128432 A1 | 6/2005 | Altmann | |
| 2005/0203619 A1 | 9/2005 | Altmann | |
| 2006/0009816 A1 | 1/2006 | Fang et al. | |
| 2006/0030938 A1 | 2/2006 | Altmann | |
| 2006/0058874 A1 | 3/2006 | Peli | |
| 2006/0066808 A1 | 3/2006 | Blum et al. | |
| 2006/0098162 A1 | 5/2006 | Bandhauer et al. | |
| 2006/0109421 A1 | 5/2006 | Ye et al. | |
| 2006/0116763 A1 | 6/2006 | Simpson | |
| 2006/0116764 A1 | 6/2006 | Simpson | |
| 2006/0116765 A1 | 6/2006 | Blake et al. | |
| 2006/0158611 A1 | 7/2006 | Piers et al. | |
| 2006/0227286 A1 | 10/2006 | Hong et al. | |
| 2006/0238702 A1 | 10/2006 | Glick et al. | |
| 2006/0244904 A1 | 11/2006 | Hong et al. | |
| 2006/0247766 A1 | 11/2006 | Marin | |
| 2007/0052920 A1 | 3/2007 | Stewart et al. | |
| 2007/0093891 A1 | 4/2007 | Tabernero et al. | |
| 2007/0129803 A1 | 6/2007 | Cumming et al. | |
| 2007/0171362 A1 | 7/2007 | Simpson et al. | |
| 2007/0182924 A1 | 8/2007 | Hong et al. | |
| 2007/0268453 A1 | 11/2007 | Hong et al. | |
| 2008/0030677 A1 | 2/2008 | Simpson | |
| 2008/0161913 A1 | 7/2008 | Brady et al. | |
| 2008/0161914 A1 | 7/2008 | Brady et al. | |

(56) References Cited

U.S. PATENT DOCUMENTS

| | | | |
|---|---|---|---|
| 2008/0212024 A1* | 9/2008 | Lai | G02C 7/028 351/205 |
| 2008/0269883 A1 | 10/2008 | Das et al. | |
| 2008/0269884 A1* | 10/2008 | Vannoy | A61F 2/1613 623/6.17 |
| 2008/0269885 A1 | 10/2008 | Simpson et al. | |
| 2008/0269886 A1 | 10/2008 | Simpson et al. | |
| 2008/0269890 A1 | 10/2008 | Simpson et al. | |
| 2008/0312738 A1 | 12/2008 | Wanders | |
| 2009/0018652 A1 | 1/2009 | Hermans et al. | |
| 2009/0062911 A1 | 3/2009 | Bogaert | |
| 2009/0164008 A1 | 6/2009 | Hong et al. | |
| 2009/0187242 A1 | 7/2009 | Weeber et al. | |
| 2009/0198326 A1 | 8/2009 | Zhou et al. | |
| 2009/0204211 A1 | 8/2009 | Angelopoulos et al. | |
| 2009/0210054 A1 | 8/2009 | Weeber et al. | |
| 2009/0234448 A1 | 9/2009 | Weeber et al. | |
| 2009/0268155 A1 | 10/2009 | Weeber | |
| 2009/0292354 A1 | 11/2009 | Gontijo et al. | |
| 2009/0295295 A1 | 12/2009 | Shannon et al. | |
| 2009/0323020 A1 | 12/2009 | Zhao et al. | |
| 2010/0016961 A1 | 1/2010 | Hong et al. | |
| 2010/0100177 A1 | 4/2010 | Zhao | |
| 2010/0100178 A1 | 4/2010 | Weeber et al. | |
| 2010/0157240 A1 | 6/2010 | Schmid et al. | |
| 2010/0161048 A1 | 6/2010 | Schaper, Jr. | |
| 2010/0188636 A1 | 7/2010 | Pinto et al. | |
| 2011/0130833 A1 | 6/2011 | Scott et al. | |
| 2011/0153014 A1 | 6/2011 | Zhang et al. | |
| 2011/0279912 A1 | 11/2011 | Fiala | |
| 2012/0277857 A1 | 11/2012 | Purchase et al. | |
| 2013/0013060 A1 | 1/2013 | Zadno-Azizi et al. | |
| 2013/0211515 A1 | 8/2013 | Blum et al. | |
| 2013/0226294 A1 | 8/2013 | Van Der Mooren et al. | |
| 2014/0022649 A1 | 1/2014 | Eckhardt | |
| 2014/0168602 A1 | 6/2014 | Weeber et al. | |
| 2014/0253877 A1 | 9/2014 | Li et al. | |
| 2015/0005877 A1 | 1/2015 | Wanders | |
| 2015/0250583 A1 | 9/2015 | Rosen et al. | |
| 2015/0250585 A1 | 9/2015 | Rosen et al. | |
| 2015/0265399 A1 | 9/2015 | Rosen et al. | |
| 2015/0297342 A1 | 10/2015 | Rosen et al. | |
| 2015/0320547 A1 | 11/2015 | Rosen et al. | |
| 2016/0067037 A1 | 3/2016 | Rosen et al. | |
| 2016/0161364 A1 | 6/2016 | Alarcon Heredia et al. | |
| 2016/0193040 A1 | 7/2016 | Qureshi et al. | |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | 9222264 A1 | 12/1992 |
| WO | 9303409 A1 | 2/1993 |
| WO | 0019906 A1 | 4/2000 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03000154 A2 | 1/2003 |
| WO | 03009053 A1 | 1/2003 |
| WO | 03022137 A2 | 3/2003 |
| WO | 2004034129 A1 | 4/2004 |
| WO | 2004049979 A1 | 6/2004 |
| WO | 2004068214 A1 | 8/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008065362 A1 | 6/2008 |
| WO | 2009076670 A1 | 6/2009 |
| WO | 2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

Atchison D.A., et al., "Shape of the Retinal Surface in Emmetropia and Myopia," Investigative Ophthalmology & Visual Science, Aug. 2005, vol. 46 (8), pp. 2698-2707.

Baskaran K., et al., "Benefit of Adaptive Optics Aberration Correction at Preferred Retinal Locus," Optometry and Vision Science, Sep. 2012, vol. 89 (9), pp. 1417-1423.

Buralli D.A., et al, "Optical Performance of Holographic Kinoforms," Applied Optics, Mar. 1989, vol. 28 (5), pp. 976-983.

Canovas C., et al., "Hybrid Adaptive-Optics Visual Simulator," Optical Letters, Jan. 15, 2010, vol. 35 (2), pp. 196-198.

Cohen A.L., "Practical Design of a Bifocal Hologram Contact Lens or Intraocular Lens," Applied Optics, Jul. 1, 1992, vol. 31 (19), pp. 3750-3754.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Escudero-Sanz I., et al., "Off-Axis Aberrations of a Wide-Angle Schematic Eye Model," Journal of the Optical Society of America. A, Optics, Image Science, and Vision, Aug. 1999, vol. 16 (8), pp. 1881-1891.

Hoffmann, P.C., et al., "Analysis of Biometry and Prevalence Data for Corneal Astigmatism in 23 239 Eyes," Journal of Cataract and Refractive Surgery, Sep. 2010, vol. 36(9), pp. 1479-1485.

International Search Report and Written Opinion for Application No. PCT/IB2015/000989, dated Sep. 8, 2015, 13 pages.

International Search Report and Written Opinion for Application No. PCT/IB2015/001027, dated Sep. 8, 2015, 14 pages.

International Search Report and Written Opinion for Application No. PCT/IB2015/001244, dated Nov. 8, 2015, 14 pages.

International Search Report and Written Opinion for Application No. PCT/IB2015/001588, dated Oct. 15, 2015, 11 pages.

International Search Report and Written Opinion for Application No. PCT/IB2015/002000, dated Feb. 12, 2016, 12 pages.

International Search Report and Written Opinion for Application No. PCT/IB2017/000318, dated Aug. 4, 2017, 14 pages.

International Search Report and Written Opinion for Application No. PCT/IB2017/000553, dated Aug. 28, 2017, 19 pages.

International Search Report and Written Opinion for Application No. PCT/US2012/052311, dated Dec. 21, 2012, 14 pages.

International Search Report and Written Opinion for Application No. PCT/US2014/020343, dated May 15, 2014, 10 pages.

Jaeken B., et al., "Comparison of the Optical Image Quality in the Periphery of Phakic and Pseudophakic Eyes," Investigative Ophthalmology & Visual Science, May 1, 2013, vol. 54 (5), pp. 3594-3599.

Jafari-Nodoushan M., et al., "Control-Flow Checking Using Branch Instructions," IEEE/IFIP International Conference on Embedded and Ubiquitous Computing, Dec. 17-20, 2008, pp. 66-72.

Lewis P., et al., "Resolution of Static and Dynamic Stimuli in the Peripheral Visual Field," Vision Research, Aug. 15, 2011, vol. 51 (16), pp. 1829-1834.

(56) References Cited

OTHER PUBLICATIONS

Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Lundstroma L., et al., "Symmetries in Peripheral Ocular Aberrations," Journal of Modern Optics, Mar. 16, 2011, vol. 58 (19-20), pp. 1690-1695.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), pp. 13858-13864.
Norrby S., et al., "Model Eyes for Evaluation of Intraocular Lenses," Applied Optics, Sep. 7, 2007, vol. 46 (26), pp. 6595-6605.
Oh N., et al., "Control-Flow Checking by Software Signatures," IEEE Transactions on Reliability, Mar. 2, 2002, vol. 51 (2), pp. 111-122.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Rosen R., et al., "Adaptive Optics for Peripheral Vision," Journal of Modern Optics, Jul. 10, 2012, vol. 59 (12), pp. 1064-1070.
Rosen R., et al., "Evaluating the Peripheral Optical Effect of Multifocal Contact Lenses," Ophthalmic and Physiological Optics, Nov. 2012, vol. 32 (6), pp. 527-534.
Rosen R., et al., "Have We Misinterpreted the Study of Hoogerheide et al. (1971)?," Optometry and Vision Science, Aug. 2012, vol. 89 (8), pp. 1235-1237.
Rosen R., et al., "Sign-dependent Sensitivity to Peripheral Defocus for Myopes Due to Aberrations," Investigative Ophthalmology & Visual Science, Oct. 17, 2012, vol. 53 (11), pp. 7176-7182.
Rosen R., et al., "Influence of Optical Defocus on Peripheral Vision," Visual Psychophysics and Physiological Optics, Jan. 2011, vol. 52 (1), pp. 318-323.
Rosen R., "Peripheral Vision: Adaptive Optics and Psychophysics," Doctoral Thesis Department of Applied Physics Royal Institute of Technology Stockholm, Sweden Apr. 2013, 86 pages.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Villegas E.A., et al., "Correlation between Optical and Psychophy, Sical Parameters as a Function of Defocus," Optometry and Vision Science, Jan. 1, 2002, vol. 79 (1), pp. 60-67.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

\* cited by examiner

OPHTHALMIC DEVICES, SYSTEM AND METHODS THAT IMPROVE PERIPHERAL VISION

CROSS-REFERENCE TO RELATED APPLICATIONS

This application is a divisional of and claims priority to U.S. patent application Ser. No. 14/692,609. filed Apr. 21, 2015, now U.S. Pat. No. 10,010,407 which claims the benefit under 35 U.S.C. § 119(e) of U.S. Provisional Application No. 61/982,135, filed on Apr. 21, 2014, titled "OPHTHALMIC DEVICES, SYSTEM AND METHODS FOR IMPROVING PERIPHERAL VISION." U.S. patent application Ser. No. 14/692,609 also claims the benefit under 35 U.S.C. § 119(e) of U.S. Provisional Application No. 62/038,667, filed on Aug. 18, 2014, titled "OPHTHALMIC DEVICES, SYSTEM AND METHODS FOR IMPROVING PERIPHERAL VISION." The entire content of each of the above identified applications are incorporated by reference herein in its entirety for all it discloses and are made part of this specification.

BACKGROUND

Field

This disclosure generally relates to devices, systems and methods that improve peripheral vision.

Description of Related Art

Intraocular Lenses (IOLs) may be used for restoring visual performance after a cataract or other ophthalmic procedure in which the natural crystalline lens is replaced with or supplemented by implantation of an IOL. When such a procedure changes the optics of the eye, generally a goal is to improve vision in the central field. Recent studies have found that, when a monofocal IOL is implanted, peripheral aberrations are changed, and that these aberrations differ significantly from those of normal, phakic eyes. The predominant change is seen with respect to peripheral astigmatism, which is the main peripheral aberration in the natural eye, followed by sphere, and then higher order aberrations. Such changes may have an impact on overall functional vision, on myopia progression, and—for newborns and children—on eye development.

There are also certain retinal conditions that reduce central vision, such as AMD or a central scotoma. Other diseases may impact central vision, even at a very young age, such as Stargardt disease, Best disease, and inverse retinitis pigmentosa. The visual outcome for patients suffering from these conditions can be improved by improving peripheral vision.

SUMMARY

The systems, methods and devices of the disclosure each have several innovative aspects, no single one of which is solely responsible for the desirable attributes disclosed herein.

Various systems, methods and devices disclosed herein are directed towards intraocular lenses (IOLs) including, for example, posterior chamber IOLs, phakic IOLs and piggyback IOLs, which are configured to improve peripheral vision. For normal patients, e.g., uncomplicated cataract patients, peripheral vision may be balanced with good central vision in order to improve or maximize overall functional vision. For those patients having a pathological loss of central vision, peripheral vision may be improved or maximized, taking into account the visual angle where the retina is healthy.

In some embodiments, an IOL can be configured to reduce peripheral aberrations by tailoring parameters of the IOL according to stop-shift equations, which are discussed in greater detail herein. The IOL can be configured to position its principal plane posterior (relative to the pupil) to a standard IOL's principal plane by tailoring the shape factor of the lens, the axial displacement (physical or virtual) of the lens, the index of refraction of the lens, the asphericity of one or more surfaces of the lens, by adding an extra aperture, or any combination of these techniques. In various embodiments, the principal place can be shifted by a distance between about 0.1 mm and about 4.5 mm by movement of haptics. In some embodiments, the shape factor of the IOL can be altered by altering the geometry (e.g., radius of curvature and/or thickness) or changing the refractive index of the material of the IOL. Altering the shape factor of the IOL can shift the principal plane by about a few hundred microns. In various embodiments, shifting the principal plane by movement of haptics and by altering the shape factor of the lens can advantageously reduce peripheral astigmatism.

In one embodiment, the principal plane of the lens is moved posteriorly, further from the iris, which is the natural aperture at the eye, or closer to the nodal point of the eye as compared to standard IOLs. This effectively changes the field curvature in the image plane, to better align with the shape of the retina. In some embodiments, the axial position of the IOL is between about 1.5 mm and about 2.5 mm behind the iris. For example, the axial position of the IOL may be about 1.9 mm behind the iris. In certain embodiments, the axial position of the IOL is between about 2.5 mm and about 3.5 mm behind the iris. For example, the axial position of the IOL may be about 2.9 mm behind the iris.

In some embodiments, the axial position of the IOL may be between about 3.5 mm and about 4.1 mm behind the iris. For example, the axial position of the IOL may be about 3.9 mm behind the iris. For regular eye dimensions, the position of the lens may be limited by the vitreous body, to not exceed about 4.5 mm behind the iris. For some embodiments of the lenses used in this example, the principal plane is about 0.4 mm posterior to the anterior lens surface. The location of the principal plane posterior to the anterior lens surface can be altered by modifying the shape factor. For example, depending on the shape factor of the lens, the principal planes can be located placed at different distances, such as, for example, greater than or equal to 0.1 mm posterior to the anterior lens surface, greater than or equal to 0.5 mm posterior to the anterior lens surface, greater than or equal to 0.8 mm posterior to the anterior lens surface, greater than or equal to 1.0 mm posterior to the anterior lens surface, greater than or equal to 1.5 mm posterior to the anterior lens surface, greater than or equal to 1.8 mm posterior to the anterior lens surface, greater than or equal to 2.1 mm posterior to the anterior lens surface, greater than or equal to 2.5 mm posterior to the anterior lens surface, greater than or equal to 3.0 mm posterior to the anterior lens surface, greater than or equal to 3.5 mm posterior to the anterior lens surface and greater than or equal to 4.0 mm posterior to the anterior lens surface. Therefore, when the example refers to a distance of the lens of, e.g., 1.5 mm behind the iris, it means the principal plane of the lens is about 1.9 mm behind the iris.

Instead of moving the lens posteriorly relative to a conventional position in the eye, a lens configuration may be applied that moves the principal plane of the lens posteriorly, while the physical lens is still in the conventional position in the eye. One way to achieve this is to change the shape factor of the lens, e.g., to a meniscus lens having a concave anterior surface and a convex posterior surface. The meniscus lens can also advantageously reduce astigmatism. Without subscribing to any particular theory, a modification of shape factor can be achieved by changing the geometry (e.g., radius of curvature, thickness) of the lens, refractive index of the material of the lens or a combination of both. Accordingly, in some embodiments, the location of the principal place can be altered by increasing or decreasing the thickness of the lens. In some embodiments, the location of the principal place can be altered by increasing or decreasing the radius of curvature of the lens. In some embodiments, an intraocular lens system of 2 lenses is used, e.g., having a negative power anterior lens and a positive power posterior lens. Those skilled in the art will appreciate that other combinations are possible.

The lens may be a multifocal lens, a lens including a prism, or a telescope lens, having the principal plane moved posteriorly by one of the methods described above. In a multifocal lens, the position of the principal plane may be determined based on analysis using one focal point, several of the focal points, or all focal points of the multifocal lens. In a preferred embodiment, a multifocal IOL has at least 2 zones, wherein the at least 2 zones have about the same optical power. The inner zone may be a spherical lens producing a good central focus. The outer zone(s) comprise of a spherical lens combined with a prism, producing a good focus at a predetermined spot in the periphery. A similar affect may be achieved if the outer zone(s) are aspheric. Alternatively, a bag-filling lens with a gradient refractive index may be used. Such lenses can also advantageously reduce age related macular degeneration (AMD).

In some embodiments, an artificial pupil may be implanted between the lenses of a dual lens system or posterior to an IOL or lens combination. Such an artificial pupil may have a similar impact as moving the IOL posteriorly.

In some embodiments, a singular circular surface structure, which acts as a phase shifting profile extends the depth of focus in the peripheral field. Implementations of such structures are described in U.S. Pat. No. 8,430,508, which is hereby incorporated by reference herein in its entirety. An implementation of a single ring IOL includes an anterior face and a posterior face. A profile can be imposed on the anterior or posterior surface or face. The profile can have an inner portion and an outer portion. The inner portion typically presents a parabolic curved shape. The inner portion may also be referred to as a microstructure, an isolated echelette, or a central echelette. Between the inner portion and the outer portion, there may be a transition zone that connects the inner and outer portions. An IOL with such a structure provides for a reduction in peripheral aberrations, including astigmatism and other higher order aberrations. In certain embodiments, a multifocal IOL is used to induce multiple foci. While traditional multifocal IOLs utilize multiple foci at multiple powers, in this embodiment, the multiple foci are of the same optical power. In addition, the multiple foci focus images on different parts of the retina, thus producing optimal optical quality at those regions of the retina that are healthy.

In some embodiments, characteristics of the retina are considered for the IOL design. In particular, a geographical map of retinal functionality and/or the retinal shape are combined with other ocular geometry, such as pupil size and location, axial positions of the pupil, lens, and retina, anterior and/or posterior corneal aberrations, tilts and decentrations within the eye, and angle kappa. A metric function can be used to improve or optimize the IOL, accounting for both central and peripheral optical quality. In some embodiments, the IOL power distribution at the periphery can be related with retinal shape. Therefore, while measuring retinal shape it might be possible to select the IOL with the peripheral power distribution that matches patient's retina.

In some embodiments, a dual-optics IOL system can be used to improve natural vision by reducing peripheral aberrations. The dual-optics lens can comprise an anterior lens and a posterior lens. The dual-optics lens can have a shape factor based on the optical powers of the anterior and posterior lenses, the shape factor being tailored to reduce peripheral aberration. The shape factor can be modified for each lens while maintaining the total optical power relatively constant. The shape factors can be modified by adjusting the anterior and posterior radii of curvature of each lens, e.g., the anterior lens and the posterior lens. The shape factors can be tailored to reduce astigmatism and spherical equivalent in the periphery of the retina while maintaining on-axis optical quality on the retina.

In some embodiments, one or more IOLs can be used which have one or more aspherical surfaces configured to improve peripheral vision by reducing peripheral aberrations. The asphericity of the surfaces can be tailored to improve off-axis contrast, thereby improving peripheral vision relative to IOLs with typical surface geometries.

In some embodiments, a method is provided for improving vision using an intraocular lens which reduces peripheral aberrations. The method includes determining a principal plane of an intraocular lens; determining a value of at least one peripheral aberration at the retina of an eye based at least in part on an initial proposed placement of the principal plane of the intraocular lens in the eye and based at least in part on a computer model of an eye; modifying a parameter of the intraocular lens, wherein the parameter consists of at least one of a shape factor of the intraocular lens, an axial displacement of the intraocular lens, an index of refraction of the intraocular lens, or an asphericity of the intraocular lens; comparing the value of the at least one peripheral aberration with a value of the at least one peripheral aberration after modification of the parameter; and incorporating the modified parameter into the intraocular lens if the modification improves the vision of the patient by reducing the at least one peripheral aberration.

Various implementations of the method can comprise determining a modified value of the at least one peripheral aberration after modification of the parameter using at least one stop-shift equation. The at least one peripheral aberration can include coma or astigmatism. The method can further comprise determining a constraint on the parameter of the intraocular lens. The intraocular lens designed using the method above can include a lens element which has an aspherical surface. The asphericity of the surface of the intraocular lens can be further modified to increase an off-axis contrast produced by the intraocular lens. In various implementations of the method modifying a parameter of the intraocular lens can include providing an additional aperture. The method can include determining a target position of the intraocular lens in an eye of a patient, wherein the target position of the intraocular lens is such that the principal plane of the intraocular lens is between 1.9 mm and 4.5 mm behind the iris.

In some embodiments, a method is provided for improving vision using a dual-optic intraocular lens comprising an anterior lens element having an anterior optical power and a posterior lens element having a posterior optical power. The method includes calculating a shape factor of the intraocular lens where the shape factor is equal to the sum of the anterior optical power and the posterior optical power divided by the difference between the posterior optical power and the anterior optical power; determining a value of at least one peripheral aberration at the retina of an eye based at least in part on the shape factor of the intraocular lens and based at least in part on a computer model of an eye; modifying an anterior shape factor of the anterior lens element by modifying an anterior radius of the anterior lens element or the posterior radius of the anterior lens element; modifying a posterior shape factor of the posterior lens element by modifying an anterior radius of the posterior lens element or the posterior radius of the posterior lens element; determining a modified value of the at least one peripheral aberration at the retina of the eye based at least in part on the shape factor of the intraocular lens and based at least in part on the computer model of an eye; comparing the value of the at least one peripheral aberration with the modified value of the at least one peripheral aberration; and incorporating the modified anterior lens element and the posterior lens element into the intraocular lens if the modification improves the vision of the patient by reducing the at least one peripheral aberration, wherein a total optical power of the intraocular lens remains substantially unchanged after modification of the anterior shape factor and the posterior change factor. In various implementations of the dual-optic intraocular lens designed by the method described above, a surface of the anterior lens element or a surface of the posterior lens element can be aspheric. The asphericity of the surface of the anterior lens element or the surface of the posterior lens element can be modified to increase an off-axis contrast produced by the intraocular lens.

One aspect of the innovative aspect disclosed herein can be implemented in a dual-optic intraocular lens comprising an anterior optic and a posterior optic. The anterior optic can have an anterior optical power. The anterior optic can include a first surface with a first radius of curvature and a second surface opposite the first surface with a second radius of curvature. The anterior optic can have an anterior shape factor that is associated with the first and the second radius of curvature. The posterior optic can have a posterior optical power. The posterior optic can include a third surface with a third radius of curvature and a fourth surface opposite the third surface with a fourth radius of curvature. The posterior optic can have a posterior shape factor that is associated with the third and the fourth radius of curvature. A shape factor of the intraocular lens given by the sum of the anterior optical power and the posterior optical power divided by the difference between the posterior optical power and the anterior optical power can be optimized by optimizing the anterior shape factor or the posterior shape factor such that a degradation in the visual information obtained from a peripheral retinal location is below a threshold degradation. A total optical power of the intraocular lens can remain substantially unchanged after modification of the anterior shape factor or the posterior shape factor.

In various implementations, the posterior optic can be disposed in the capsular bag of the eye of a patient. The anterior optic can be disposed in the capsular bag of the eye of a patient or at a location between the iris and the capsular bag. In various implementations, at least one of the first, second, third or fourth surface can be aspheric.

In some embodiments, a method is provided for increasing contrast sensitivity function (CSF) for peripheral vision. The method includes providing a first IOL for implanting into a first eye of the patient, the first IOL configured to increase acuity of a sagittal image; and providing a second intraocular lens (IOL) for implanting into a second eye of a patient, the second IOL configured to increase CSF of a tangential image.

In various implementations of the method, the first IOL can be configured to increase contrast of the sagittal image when implanted at a first distance from the pupil. The second IOL can be configured to increase contrast of the tangential image when implanted at a second distance from the pupil. The first IOL can be configured to be implanted in the first eye at a first distance from the pupil and the second IOL can be configured to be implanted in the second eye at a second distance from the pupil. The first distance can be lesser than the second distance. A difference between the first distance and the second distance can be between about 0.5 mm and about 5 mm.

In some embodiments, an IOL is provided that is configured to increase CSF in the horizontal field of view without increasing CSF in the vertical field of view to improve peripheral vision. The IOL includes at least one toric portion and at least one non-toric portion. In various implementations of the IOL, the at least one toric portion can have a higher optical power along the vertical axis than the horizontal axis. The at least one toric portion can be disposed in a central region of the IOL. The at least one toric portion can be disposed in a peripheral region of the IOL. The IOL can include features that induce spherical aberrations. The IOL can include features that induce aspherical aberrations. The IOL can include diffractive features. The IOL can be configured to provide astigmatic correction. The IOL can be configured to provide extended depth of focus. The IOL can be configured to provide acuity for peripheral vision. The toric portion can improve acuity for peripheral vision along a horizontal direction.

In some embodiments, an IOL is provided that is configured to compensate for peripheral aberrations, such as, for example, peripheral astigmatism and horizontal coma arising from light incident at oblique angles. Various embodiments of IOL that compensate for peripheral aberrations can reduce coma and/or astigmatism in the peripheral field of view. Due to the oblique incidence of the light in the eye, astigmatism increases with eccentricity. The increase in astigmatism with eccentricity follows a fixed trend. As previous studies have found, this dependence does not change with age and/or foveal refractive errors, either for foveal sphere or astigmatism. Therefore patients can benefit from embodiments of IOLs having an arrangement of optical features (e.g. optical elements, grooves, volume or surface diffractive features, regions of varying refractive index, etc.) that results in a peripheral astigmatism that decreases with eccentricity. The decrease in astigmatism with eccentricity for the IOL can follow an opposite trend.

Recent studies indicate that similar to peripheral astigmatism, horizontal coma is also independent of the patient's age and/or foveal refractive errors, axial length of the cornea, corneal curvature, etc. and depends on the eccentricity or field of view according to a fixed trend. Accordingly, errors in peripheral vision can be compensated by an IOL having an arrangement of optical features (e.g. optical elements, grooves, volume or surface diffractive features, regions of varying refractive index, etc.) such that the dependence of horizontal coma for the IOL on the eccentricity or field of view has an opposite trend.

For example, in various implementations, an IOL configured to correct for peripheral aberrations in a patient can include an arrangement of a first set of optical features and an arrangement of a second set of optical features that compensate for peripheral aberrations. The arrangement of the first set of optical features can be determined based on the direction of incident light and independent of the spherical power required to achieve emmetropia. The arrangement of the second set of optical features can be determined based on the spherical power required to achieve emmetropia. The arrangement of the first set of optical features can compensate for peripheral astigmatism and/or horizontal coma. The arrangement of the second set of optical features can compensate for peripheral defocus. The arrangement of the second set of optical features can be determined based on an axial length of the patient's eye or a curvature of the cornea.

Generally, peripheral defocus changes as a function of the foveal refractive state. Accordingly, in various embodiments of IOLs, the amount of defocus can vary based on the refractive power of the IOL, which ultimately depends on the preoperative refractive state or preoperative biometry of the patient. For example, since patients with hypermetropia have a different defocus distribution as compared to patients with myopia the arrangement of optical features that compensates for peripheral defocus will be different in both cases. As a way of example, patients with hypermetropia have relative peripheral myopia. In such patients, a higher central power of the IOL can be associated with a lower peripheral power distribution, as compared to the central power. On the other hand, patients with myopia tend to have relative peripheral hyperopia. In such patients, a lower central power of the IOL can be associated with a higher peripheral power distribution, relative to the central power.

Thus, the present disclosure provides a lens apparatus, system and method that improve peripheral visual acuity at least in part by reducing aberrations arising from light directed to peripheral or high field angle retinal areas (sometimes referred to herein as peripheral aberration) relative to standard IOLs while maintaining good vision arising from light directed to most sensitive or low field angle or central retinal areas (sometimes referred to herein as central vision).

Various implementations of an IOL configured to correct for peripheral aberrations in a patient's eye can include a first optical power distribution that compensates for peripheral astigmatism; a second optical power distribution that compensates for horizontal coma in peripheral regions; and a third optical power distribution that compensates for defocus in the peripheral regions. The first and second optical power distribution can be independent of foveal refractive state of the patient's eye and the third optical power distribution can depend on the foveal refractive state of the patient's eye and/or the IOL power required for the patient to achieve foveal emmetropia. The first power distribution can vary nonlinearly with visual field angle. The first power distribution can vary quadratically with visual field angle. The first power distribution can have a higher absolute value of cylinder power at visual field angle having an absolute value greater than or equal to 10 degrees than the absolute value of cylinder power at visual field angle having an absolute value less than 10 degrees. The first power distribution can have increased astigmatic correcting power in the peripheral regions and decreased astigmatic correcting power in a central region. The second power distribution can vary linearly with visual field angle. The second power distribution can linearly decrease from a first peripheral region oriented temporally to a second peripheral region oriented nasally for left eyes and increase from a first peripheral region oriented temporally to a second peripheral region oriented nasally in right eyes. The third power distribution can be configured to provide myopic correction power in the peripheral regions for a patient with emmetropia, hyperopia or low myopia. The third power distribution can be configured such that an absolute magnitude of spherical optical power for visual field angles having an absolute value greater than or equal to 10 degrees is greater than the absolute magnitude of spherical optical power for visual field angles having an absolute value less than 10 degrees for a patient with emmetropia, hyperopia or low myopia. The third power distribution can be configured such that an absolute magnitude of spherical optical power for visual field angles having an absolute value greater than or equal to 10 degrees is smaller than the absolute magnitude of spherical optical power for visual field angles having an absolute value less than or equal to 10 degrees for a patient with moderate or high myopia.

An innovative aspect of the subject matter disclosed herein can be implemented in a method of compensating for peripheral aberrations. The method comprises determining a first optical power distribution that compensates for peripheral aberrations resulting from oblique incidence of light; and determining a second optical power distribution that compensates for peripheral aberrations based on the patient's ocular characteristics. In various implementations, the second optical power distribution can be determined based on at least one of foveal refractive power, an axial length of the eye or a curvature of the cornea. The second power distribution can be configured to provide myopic correction power in the peripheral regions for a patient with emmetropia, hyperopia or low myopia. The second optical power distribution can be determined based on the required IOL power to achieve foveal emmetropia. The second power distribution can be configured such that an absolute magnitude of spherical optical power for visual field angles having an absolute value greater than or equal to 10 degrees is greater than the absolute magnitude of spherical optical power for visual field angles having an absolute value less than 10 degrees for a patient with emmetropia, hyperopia or low myopia. The second power distribution can be configured to provide hyperopic correction in the peripheral regions for a patient with moderate or high myopia. The second power distribution can be configured such that an absolute magnitude of spherical optical power for visual field angles having an absolute value greater than or equal to 10 degrees is smaller than the absolute magnitude of spherical optical power for visual field angles having an absolute value less than 10 degrees for a patient with moderate or high myopia.

Various implementations disclosed herein include an IOL configured to compensate for peripheral astigmatism in a patient. The IOL can be configured to provide a cylinder power with an absolute magnitude of at least 0.5 Diopter for at least one visual field angle having an absolute value greater than or equal to 10 degrees. The IOL can be configured to have a horizontal coma coefficient of at least 0.01 microns for at least one visual field angle greater than or equal to 10 degrees in the nasal visual field for right eyes and temporal visual field for left eyes. Alternately, the IOL can be configured to have a horizontal coma coefficient of at least −0.01 microns for at least one visual field angle greater than or equal to +10 degrees in the temporal visual field for right eyes and nasal visual field for left eyes. Such implementations of an IOL can be configured to compensate for horizontal coma.

Various implementations of an IOL described herein can be configured to compensate for peripheral defocus. Implementations of an IOL configured to compensate for peripheral defocus can provide defocus between about −0.1 Diopter and about +1.0 Diopter for a patient with spherical equivalent power between about −0.5 Diopter and about +0.5 Diopter for at least one visual field angle having an absolute value greater than or equal to 10 degrees is. Implementations of an IOL configured to compensate for peripheral defocus can provide defocus between about −0.1 Diopter and about +2.0 Diopter for a patient with spherical equivalent power between about −0.5 Diopter and about −1.5 Diopter for at least one visual field angle having an absolute value greater than or equal to 10 degrees. Implementations of an IOL configured to compensate for peripheral defocus can provide defocus between about +1.0 Diopter and about +3.0 Diopter for a patient with spherical equivalent power between about −1.5 Diopter and about −2.5 Diopter for at least one visual field angle having an absolute value greater than or equal to 10 degrees. Various implementations of an IOL configured to compensate for peripheral defocus can provide defocus between about +2.5 Diopter and about +6.0 Diopter for a patient with spherical equivalent power between about −2.5 Diopter and about −6.0 Diopter for at least one visual field angle having an absolute value greater than or equal to 10 degrees.

Various implementations of an IOL described herein can include a plurality of optical features that have an overall optical power distribution that compensates for peripheral rotationally and non-rotationally symmetric aberrations. The non-rotationally symmetric aberrations can include peripheral astigmatism and horizontal coma. The rotationally symmetric aberration can include defocus. An arrangement of some of the plurality of optical features that compensate for non-rotationally symmetric aberrations can be independent of the spherical power of the IOL. The arrangement of some of the plurality of optical features that compensate for non-rotationally symmetric aberrations can depends on whether the eye to be implanted is right or left. An arrangement of some of the plurality of optical features that compensates for rotationally symmetric aberrations can depend on the spherical power of the IOL. An arrangement of some of the plurality of optical features that compensates for rotationally symmetric aberrations can be different for optical powers between 0.0 D and 10.0 D, 10.0 D and 25.0 D and 25.0 D and 34.0 D.

Various implementations of IOLs described herein can include markings showing the orientation of the IOL and the eye to be implanted.

Various embodiments of an IOL include a first surface that receives incident light entering through the cornea and the natural pupil and a second surface opposite the first surface through which incident light exits the IOL and propagates towards the retina. In some such embodiments, an extra aperture can be provided after (e.g., at the second surface or posterior to) the second surface of the IOL. This extra aperture can reduce the peripheral aberrations arising from the cornea. The shape of the cornea and the distance between the cornea and the posterior surface of the IOL, which can be large in some embodiments, can enhance the extra aperture's capability of reducing peripheral aberrations arising from the cornea. The natural pupil can reduce the peripheral aberrations from the IOL itself An innovative aspect of the subject matter disclosed herein can be implemented in an intraocular lens configured to improve vision for a patient's eye. The intraocular lens comprises an optic comprising a first surface and a second surface opposite the first surface. The first surface and the second surface are intersected by an optical axis. The optic is symmetric about the optical axis. The first or the second surface of the optic can be aspheric. The optic is configured to focus light incident along a direction parallel to the optical axis at the fovea to produce a functional foveal image. The optic is further configured to focus light incident on the patient's eye at an oblique angle with respect to the optical axis at a peripheral retinal location disposed at a distance from the fovea. Light can be incident at one or more oblique angles between about 1 degree and about 30 degrees. In various implementations, light can be incident at an oblique angle greater than 30 degrees from example, at oblique angle up to 45 degrees, up to 60 degrees, up to 75 degrees or greater. The peripheral retinal location can have an eccentricity between 1 and 30 degrees with respect to the optical axis. In various implementations, the peripheral retinal location can have an eccentricity greater than 30 degrees. For example, the peripheral retinal location can have an eccentricity up to 45-50 degrees with respect to the optical axis of the eye.

The optic is configured to improve image quality at the peripheral retinal location by reducing at least one optical aberration at the peripheral retinal location. The at least one optical aberration can be selected from the group consisting of defocus, peripheral astigmatism and coma. The foveal image can have a modulation transfer function (MTF) of at least 0.5 at a spatial frequency of 100 cycles/mm for both the tangential and the sagittal foci in green light for a pupil size between 3-5 mm. An image formed at the peripheral retinal location can have a figure of merit of at least 0.5. In various implementations, the figure of merit can be an average MTF for a range of spatial frequencies between 0 cycles/mm and 30 cycles/mm obtained at different eccentricities between 1 and 30 degrees. The first or the second surface of the optic can comprise a plurality of optical features that are configured to reduce the at least one optical aberration.

In various implementations, the optic can be a meniscus lens with a vertex curving inwards from edges of the optic. The optic can have a maximum thickness between about 0.3 mm and about 2.0 mm. In various implementations, the lens can be a dual-optic IOL further comprising a second optic separated from the optic by a fixed or a variable distance. In implementations of the dual-optic IOL, wherein the distance between the two optics is variable, the distance can be varied by application of ocular forces. A first optic of the dual-optic IOL can be disposed in the capsular bag of the patient's eye, and the second optic can be disposed between the iris and the patient's eye. Alternately, both the optics of the dual-optic IOL can be disposed in the capsular bag of the patient's eye.

The optic can be configured to improve image quality at the peripheral retinal location by adjusting a shape factor of the optic such that the at least one peripheral optical aberration is reduced. The shape factor of the optic can be adjusted by adjusting a parameter of the optic. The parameter can be selected from the group consisting of a curvature of the first or the second surface, an axial position of the optic with respect to the retina and a thickness of the optic.

Another innovative aspect of the subject matter disclosed herein can be implemented in a method of selecting an intraocular lens (IOL) configured to be implanted in a patient's eye. The method comprises obtaining at least one physical or optical characteristic of the patient's eye using a diagnostic instrument; and selecting an IOL having a shape factor that is configured to focus light incident along a direction parallel to the optical axis at the fovea to produce a functional foveal image and is further configured to improve image quality at a peripheral retinal location disposed at a distance from the fovea by reducing at least one optical aberration at the peripheral retinal location. The peripheral retinal location can have an eccentricity between 1 and 30 degrees. In various implementations, the peripheral retinal location can have an eccentricity greater than 30 degrees (e.g., up to 45-50 degrees). The shape factor of the IOL can be selected based on the at least one physical or optical characteristic of the patient's eye. The shape factor of the IOL can be adjusted by adjusting a parameter of the optic. The parameter of the optic can include a curvature of the first or the second surface, an axial position of the optic with respect to the retina and/or a thickness of the optic. At least one surface of the IOL can be aspheric. The optic can be configured to provide a foveal image having a modulation transfer function (MTF) of at least 0.5 at a spatial frequency of 100 cycles/mm for both the tangential and the sagittal foci in green light for a pupil size between 3-5 mm. An image formed at the peripheral retinal location by the optic can have a figure of merit of at least 0.5. In various implementation, the figure of merit can be an average MTF for a range of spatial frequencies between 0 cycles/mm and 30 cycles/mm obtained at different eccentricities between 1 and 30 degrees.

BRIEF DESCRIPTION OF THE DRAWINGS

The systems, methods and devices may be better understood from the following detailed description when read in conjunction with the accompanying schematic drawings, which are for illustrative purposes only. The drawings include the following figures.

34C illustrates the through-focus MTF at a spatial frequency of 100 cycles/mm in green light for a 5 mm pupil provided by the standard IOL.

Figure 35A:
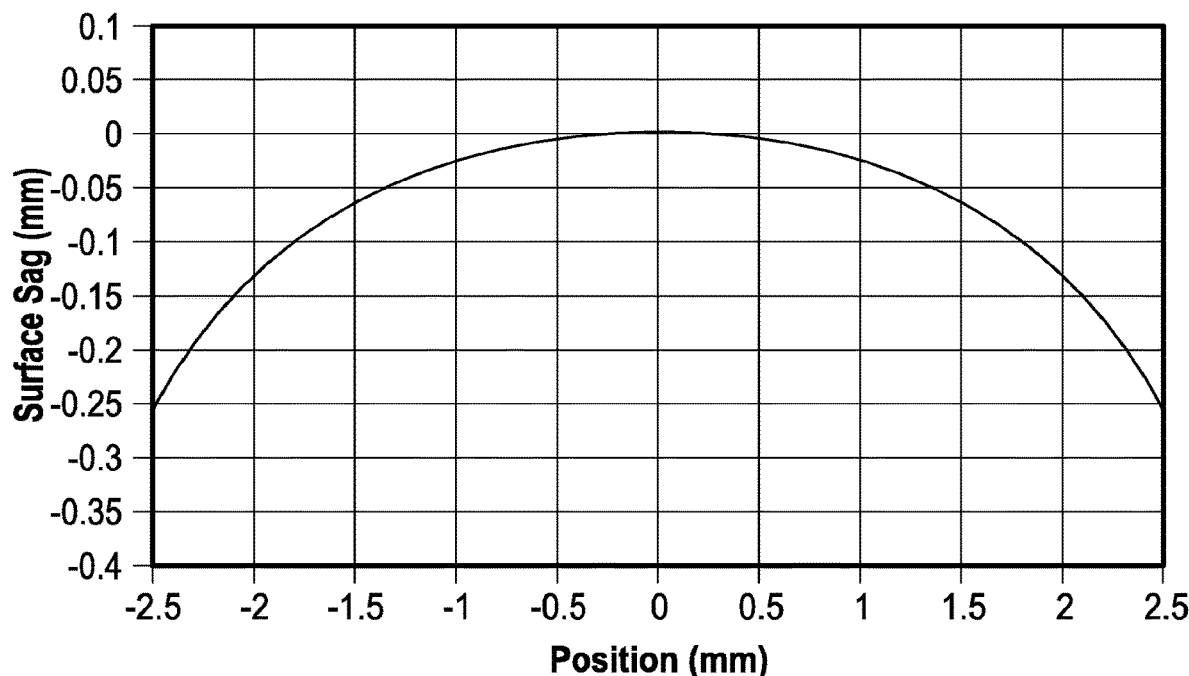
Figure 35B:
Figure 35C:
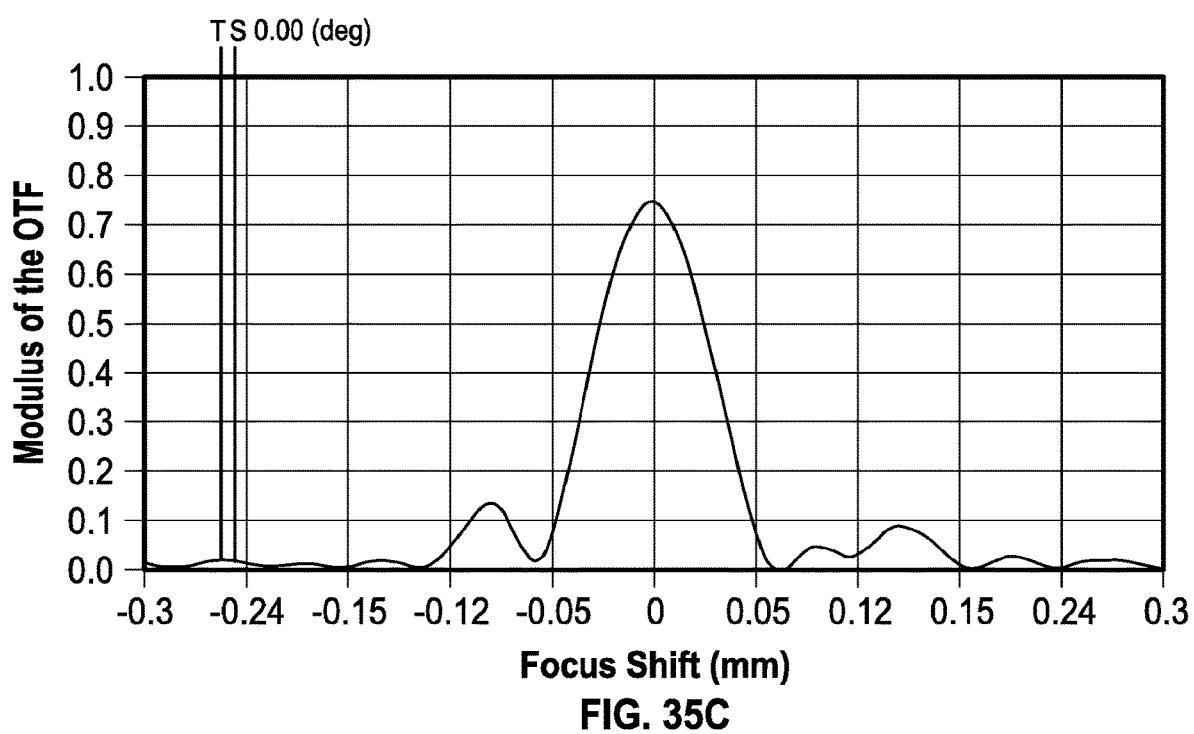

FIG. 35A illustrates the surface sag of a first surface of an implementation of a meniscus IOL and FIG. 35B illustrates the surface sag of a second surface of the meniscus IOL. FIG. 35C illustrates the through-focus MTF at a spatial frequency of 100 cycles/mm in green light for a 5 mm pupil provided by the meniscus IOL.

Figure 36A:
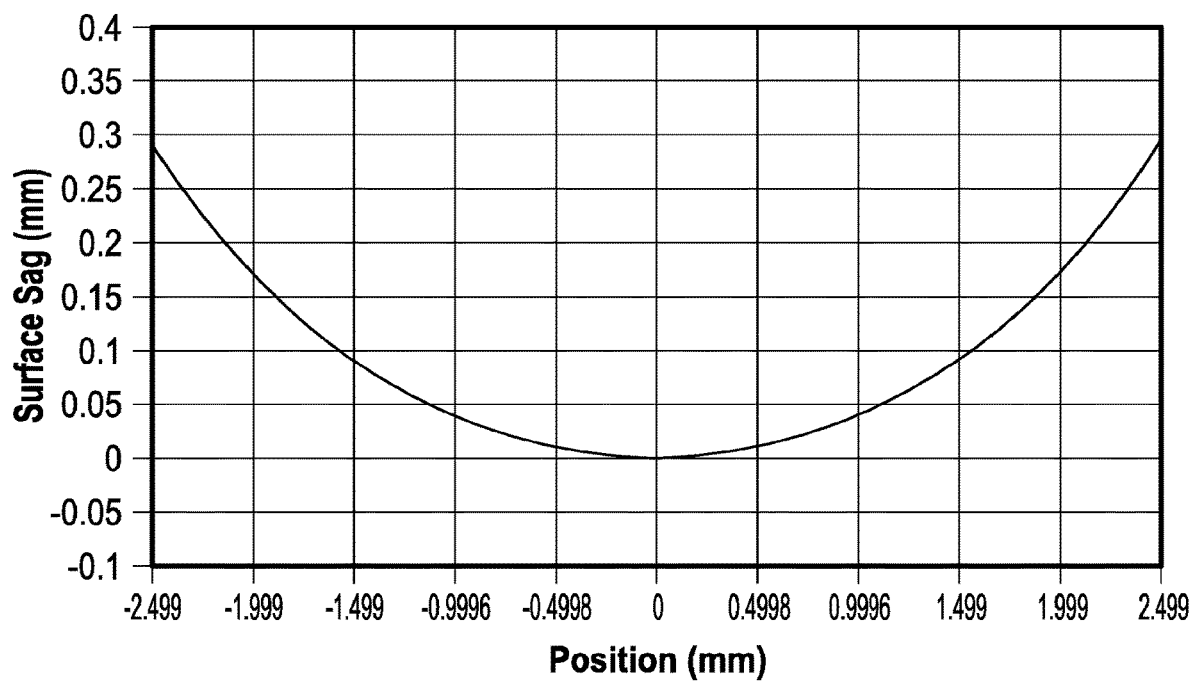
Figure 36B:
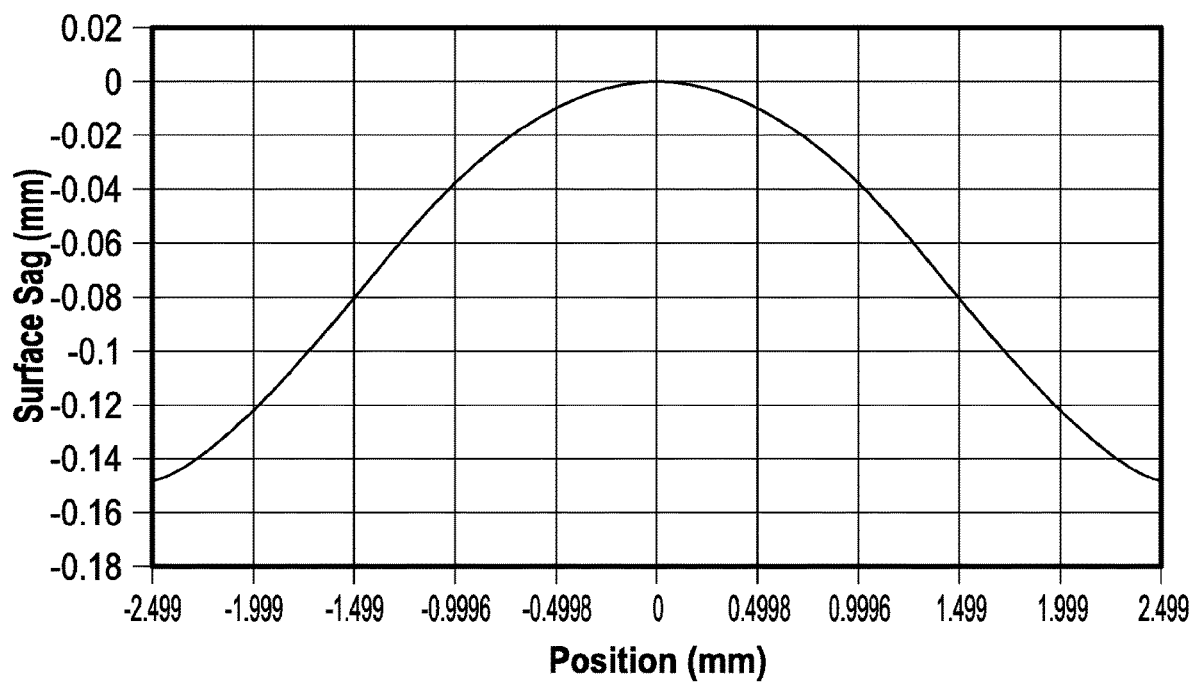
Figure 36C:
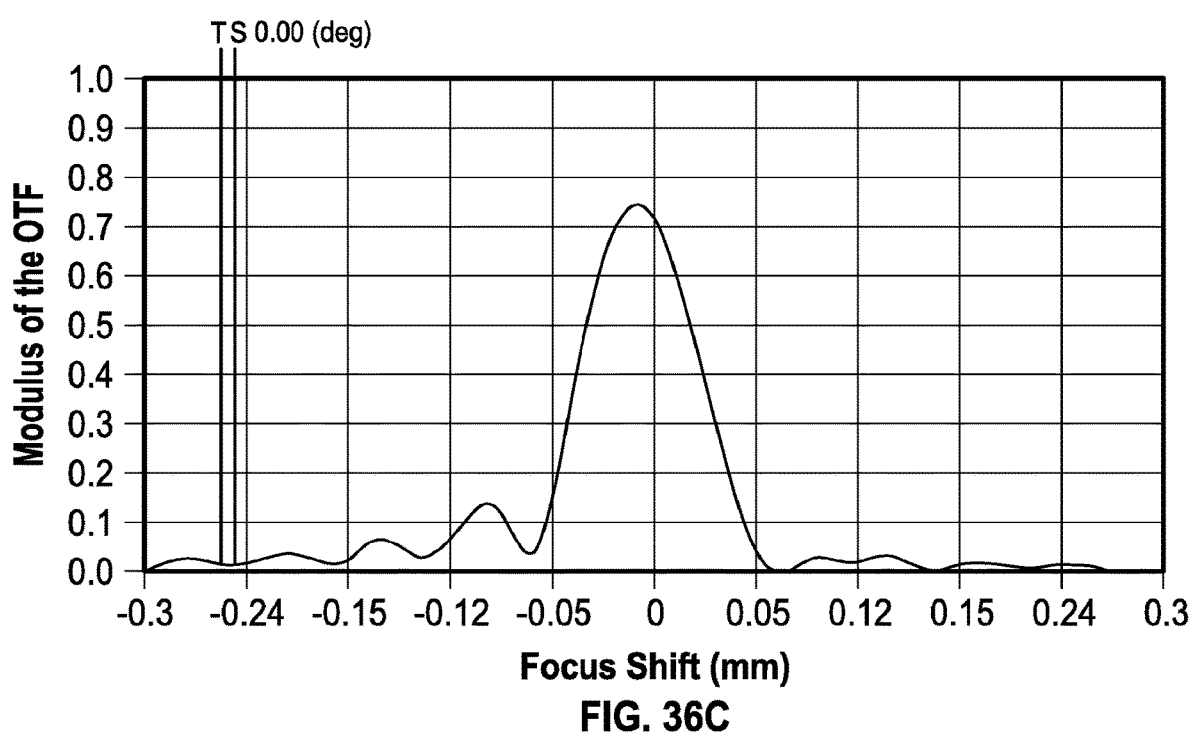

FIG. 36A illustrates the surface sag of a first surface of an implementation of a double aspheric IOL and FIG. 36B illustrates the surface sag of a second surface of the double aspheric IOL. FIG. 36C illustrates the through-focus MTF at a spatial frequency of 100 cycles/mm in green light for a 5 mm pupil provided by the double aspheric IOL.

Figure 37A:
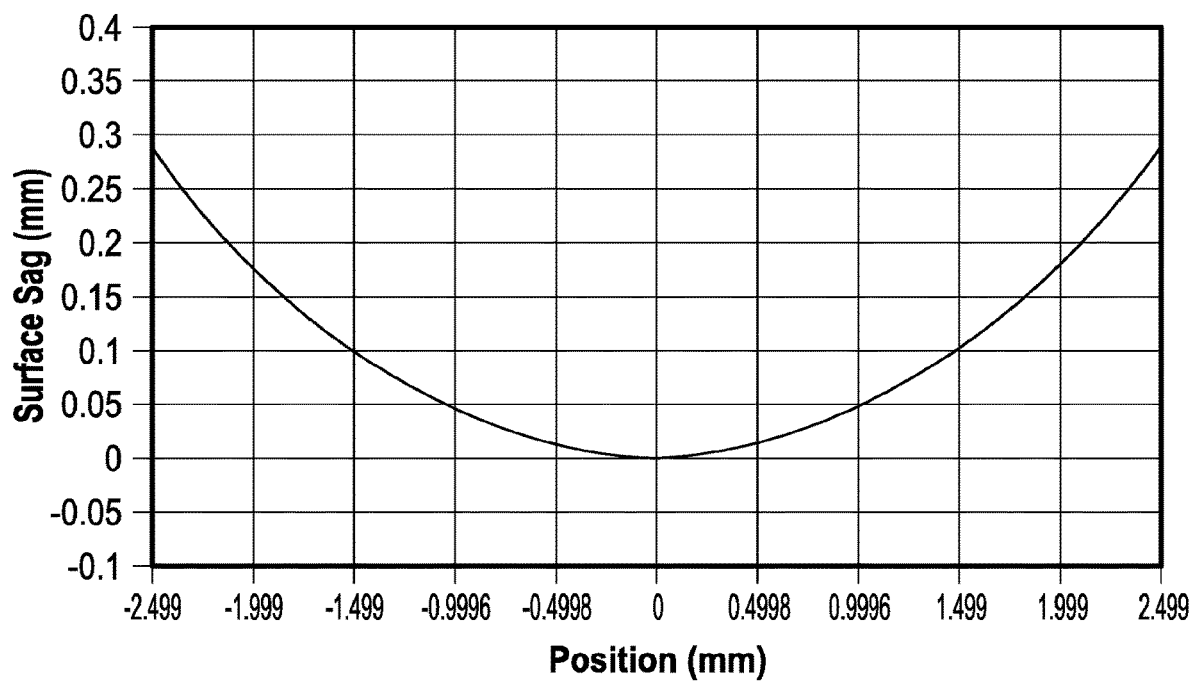
Figure 37B:
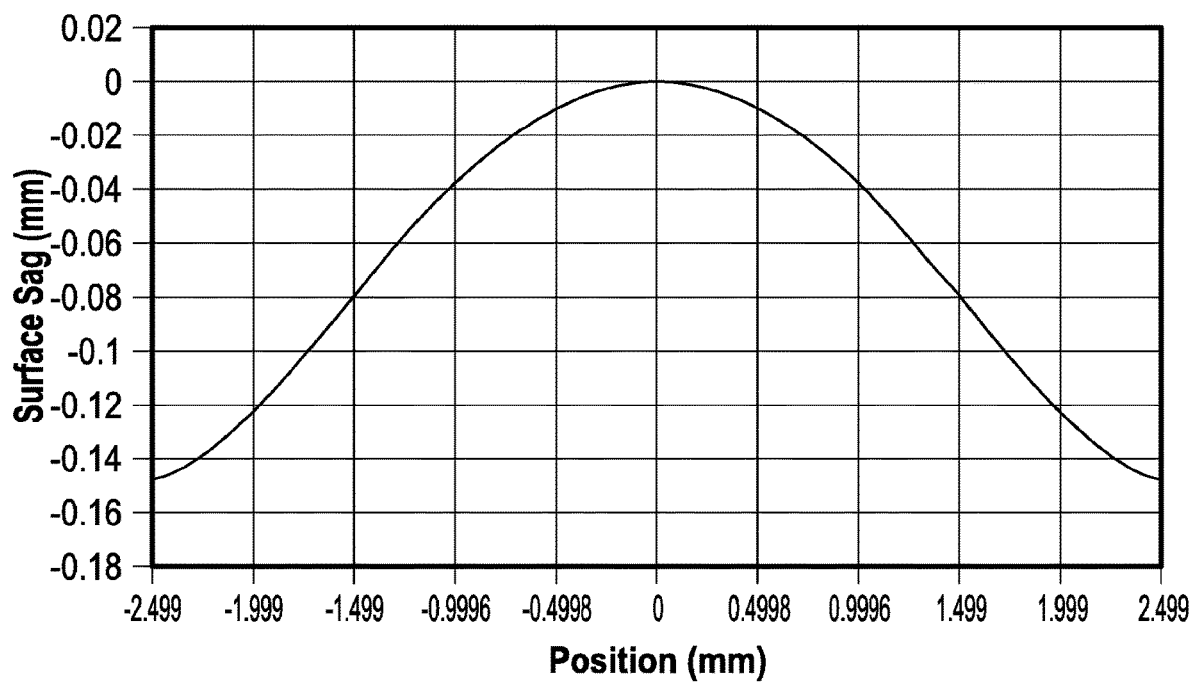
Figure 37C:
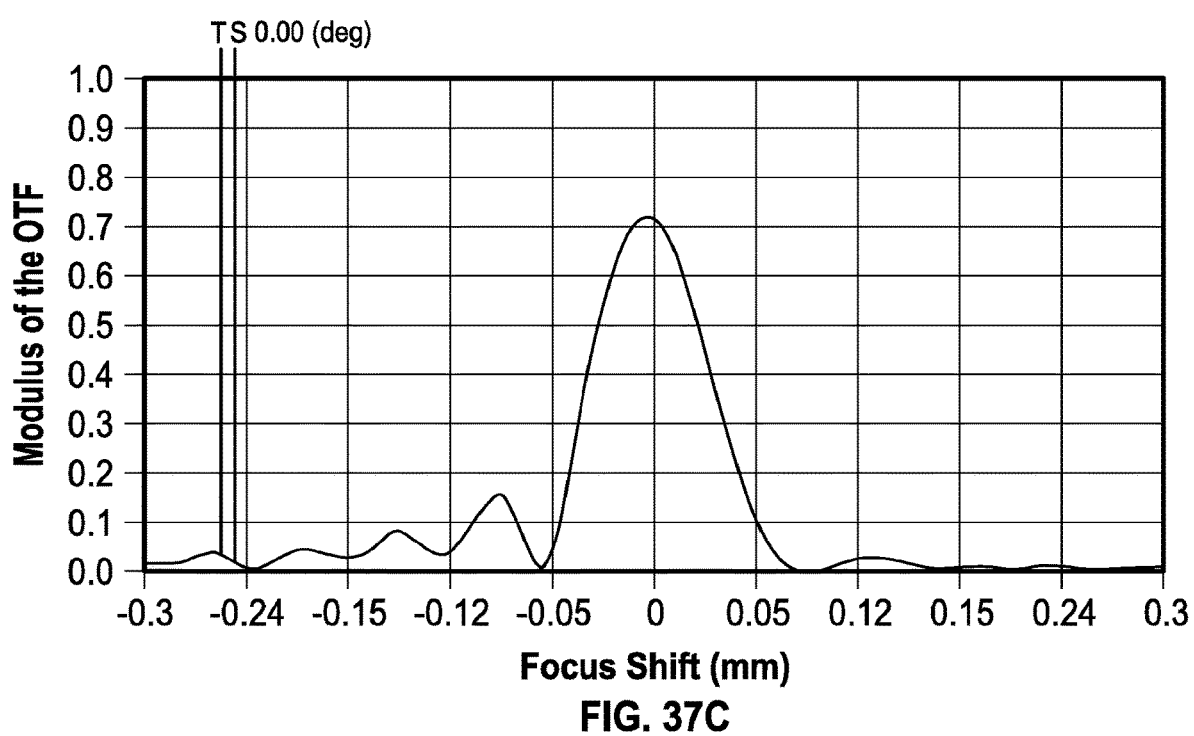

FIG. 37A illustrates the surface sag of a first surface of an implementation of a thick IOL and FIG. 37B illustrates the surface sag of a second surface of the thick IOL. FIG. 37C illustrates the through-focus MTF at a spatial frequency of 100 cycles/mm in green light for a 5 mm pupil provided by the thick IOL.

Figure 38A:
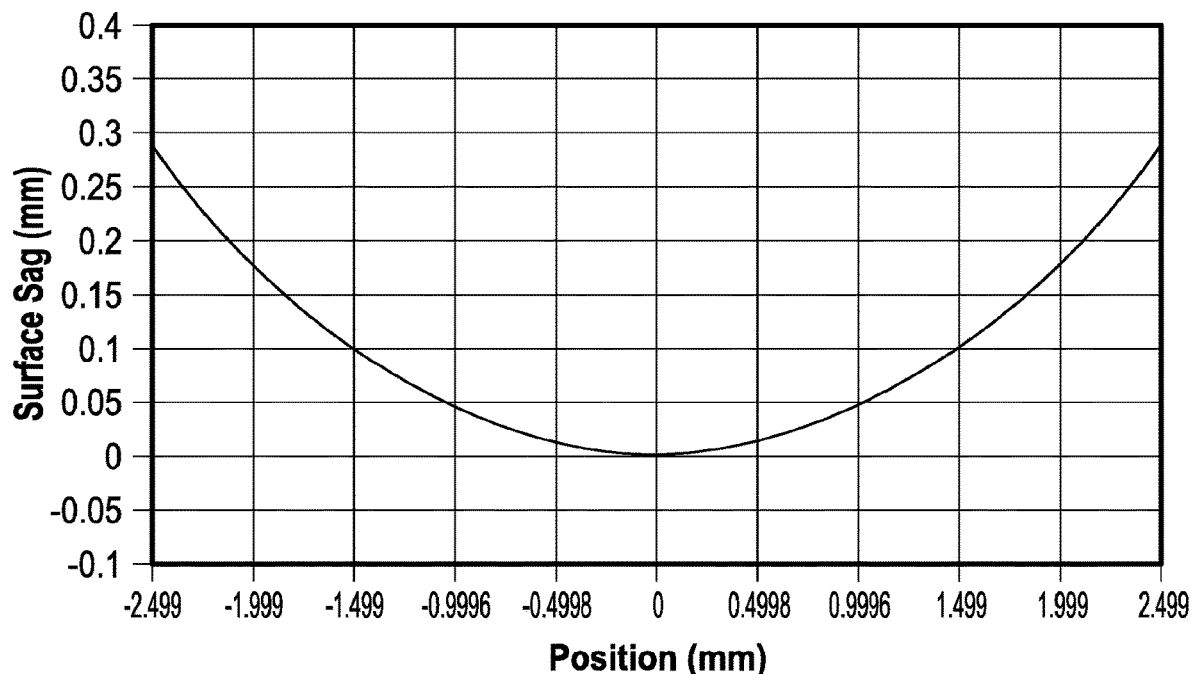
Figure 38B:
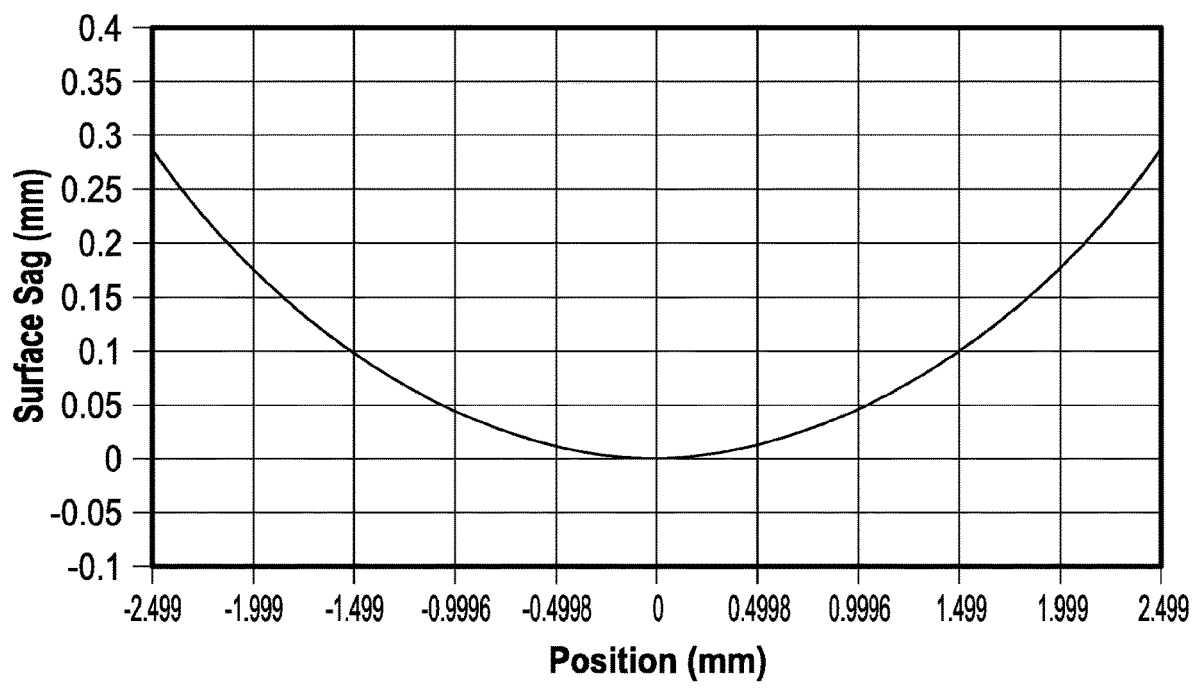
Figure 38C:
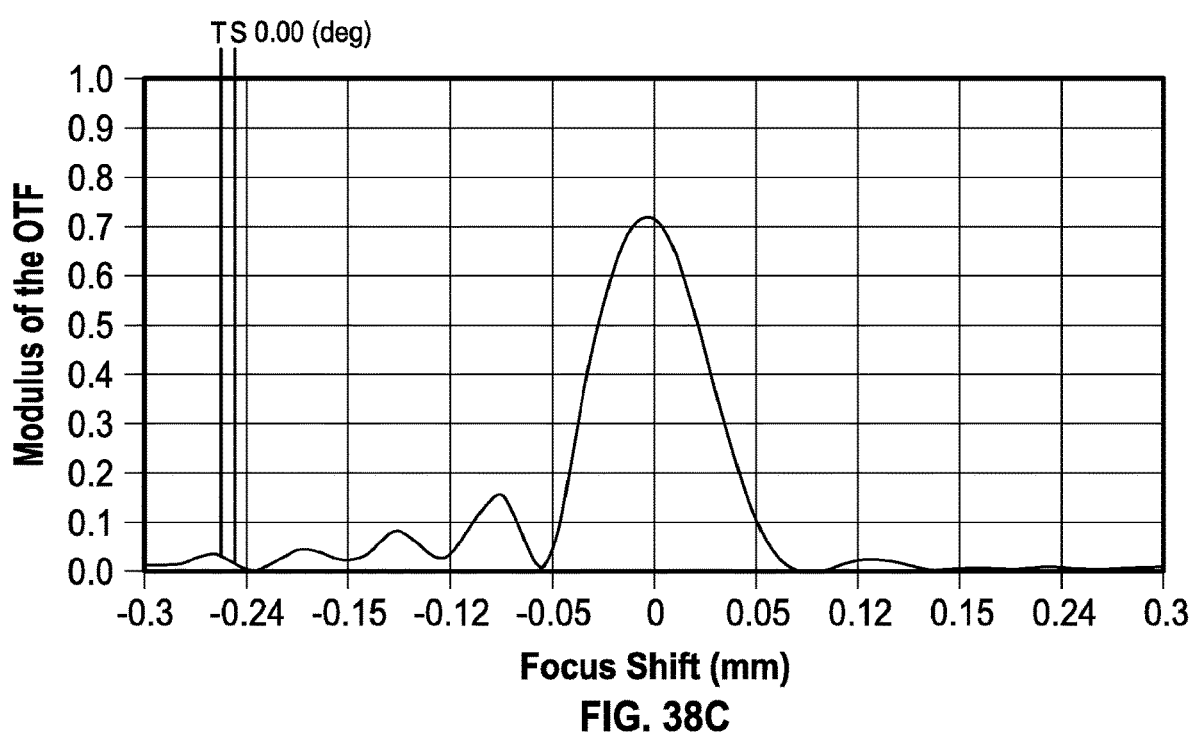

FIG. 38A illustrates the surface sag of a first surface of an implementation of a shifted aspheric IOL and FIG. 38B illustrates the surface sag of a second surface of the shifted aspheric IOL. FIG. 38C illustrates the through-focus MTF at a spatial frequency of 100 cycles/mm in green light for a 5 mm pupil provided by the shifted aspheric IOL.

Figure 39A:
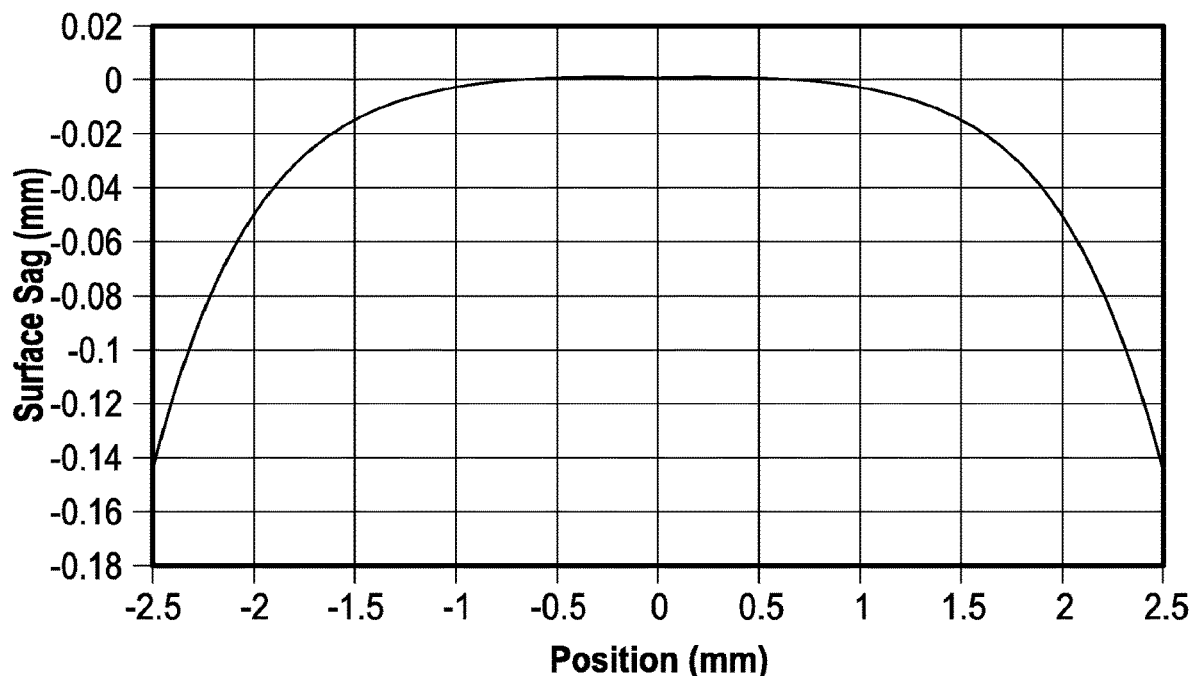
Figure 39B:
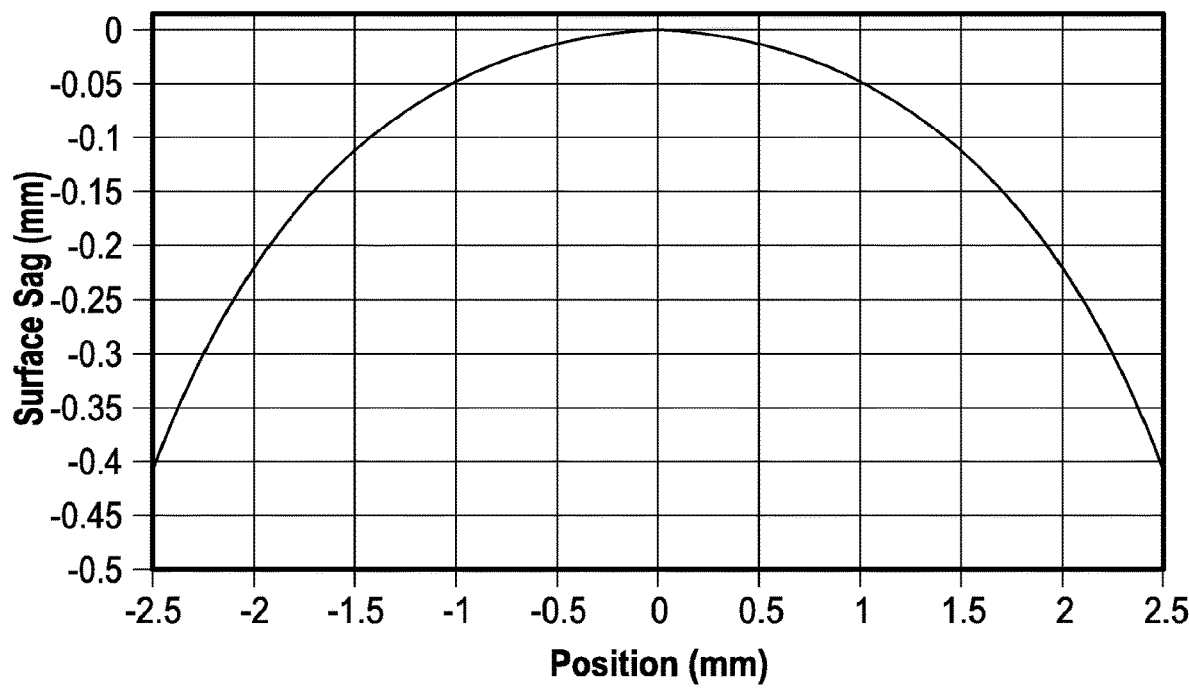
Figure 39C:
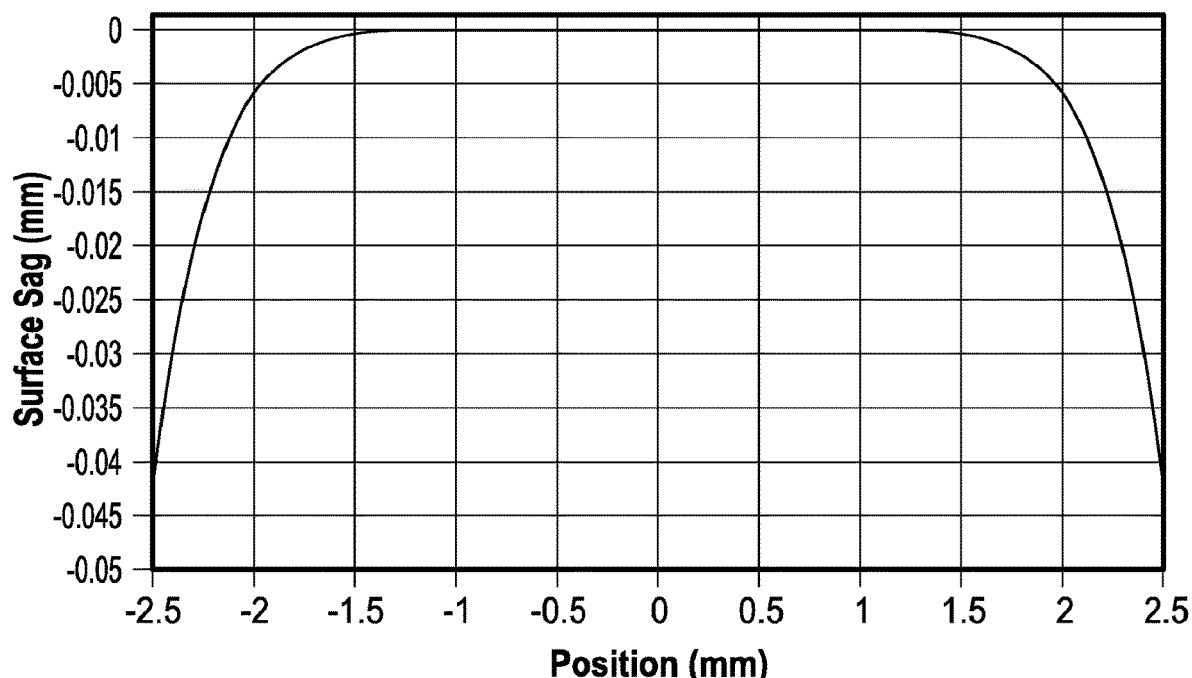
Figure 39D:
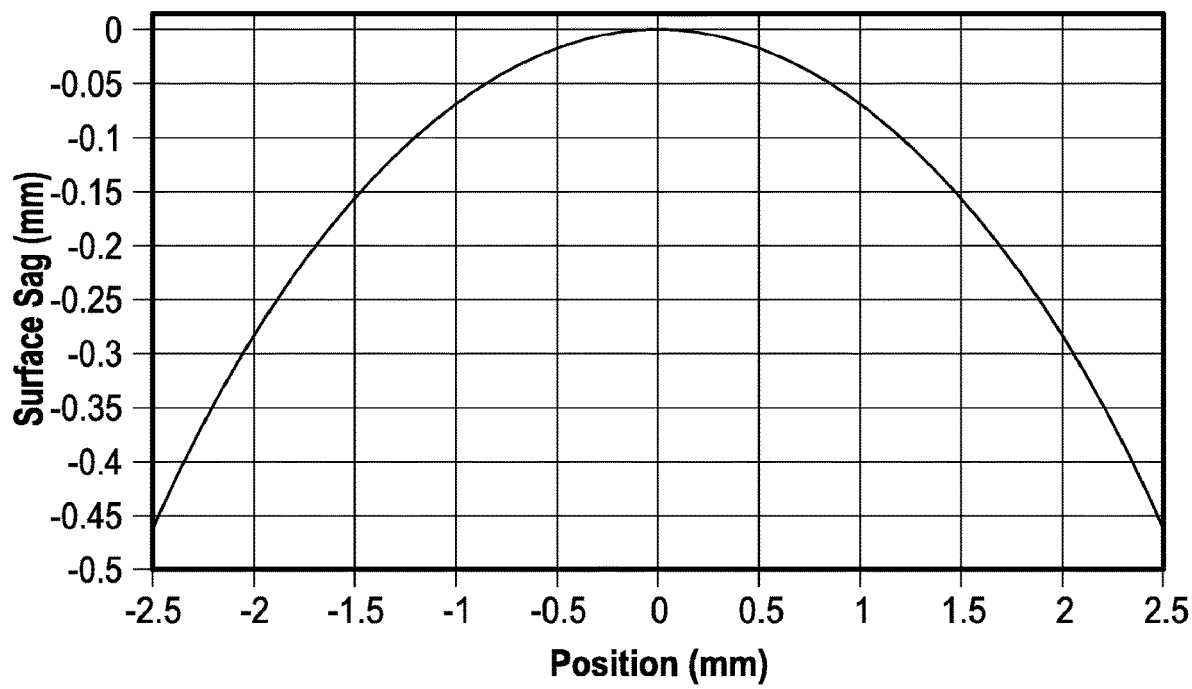
Figure 39E:
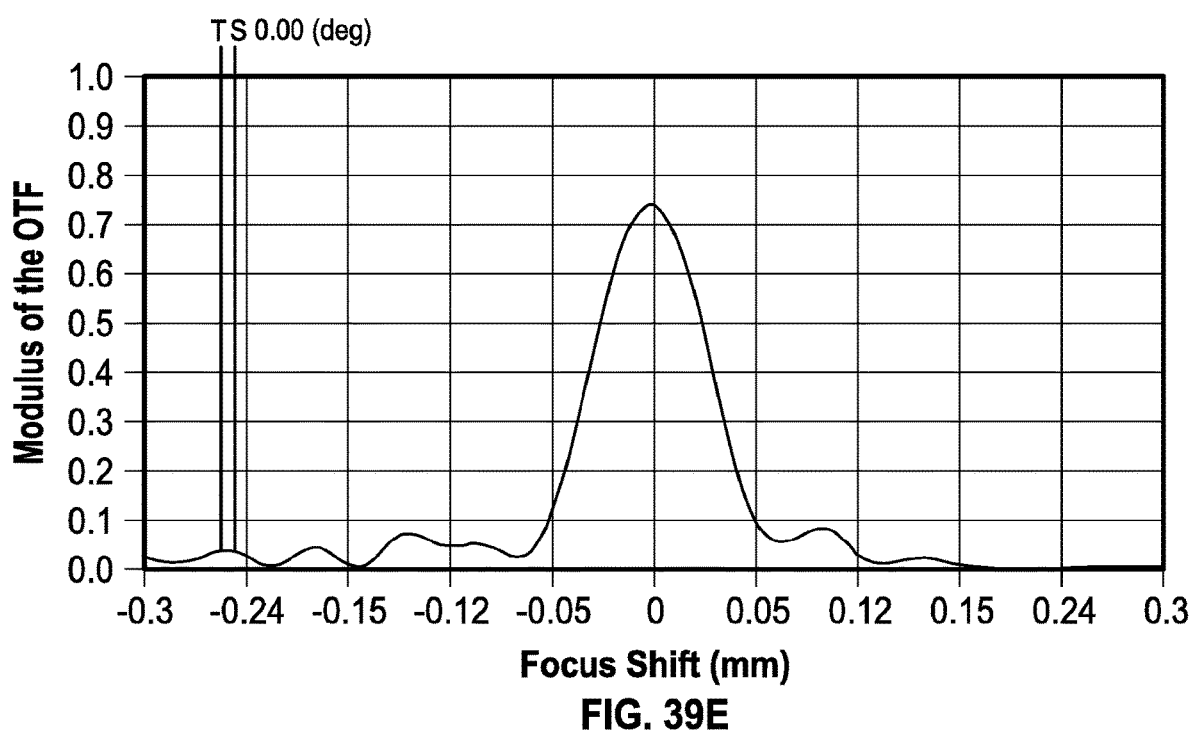

FIG. 39A illustrates the surface sag of a first surface of a first optic of a dual optic IOL and FIG. 39B illustrates the surface sag of a second surface of the first optic. FIG. 39C illustrates the surface sag of a first surface of a second optic of a dual optic IOL and FIG. 39D illustrates the surface sag of a second surface of the second optic. FIG. 39E illustrates the through-focus MTF at a spatial frequency of 100 cycles/mm in green light for a 5 mm pupil provided by the dual optic IOL.

Figure 40A:
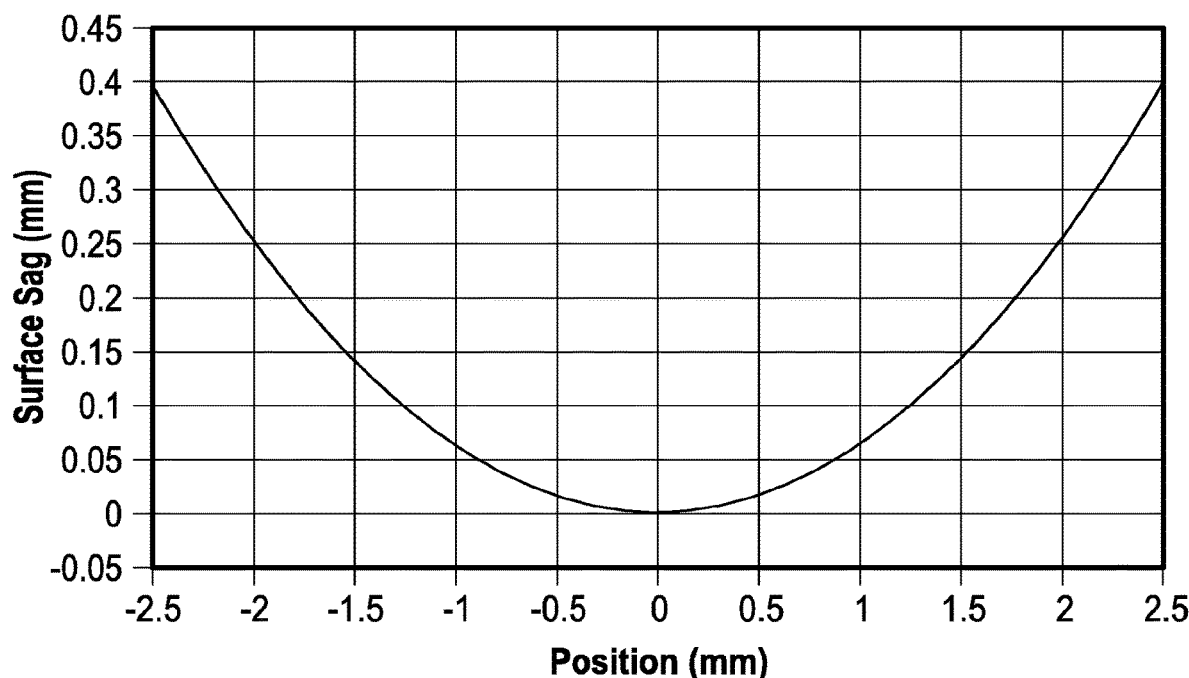
Figure 40B:
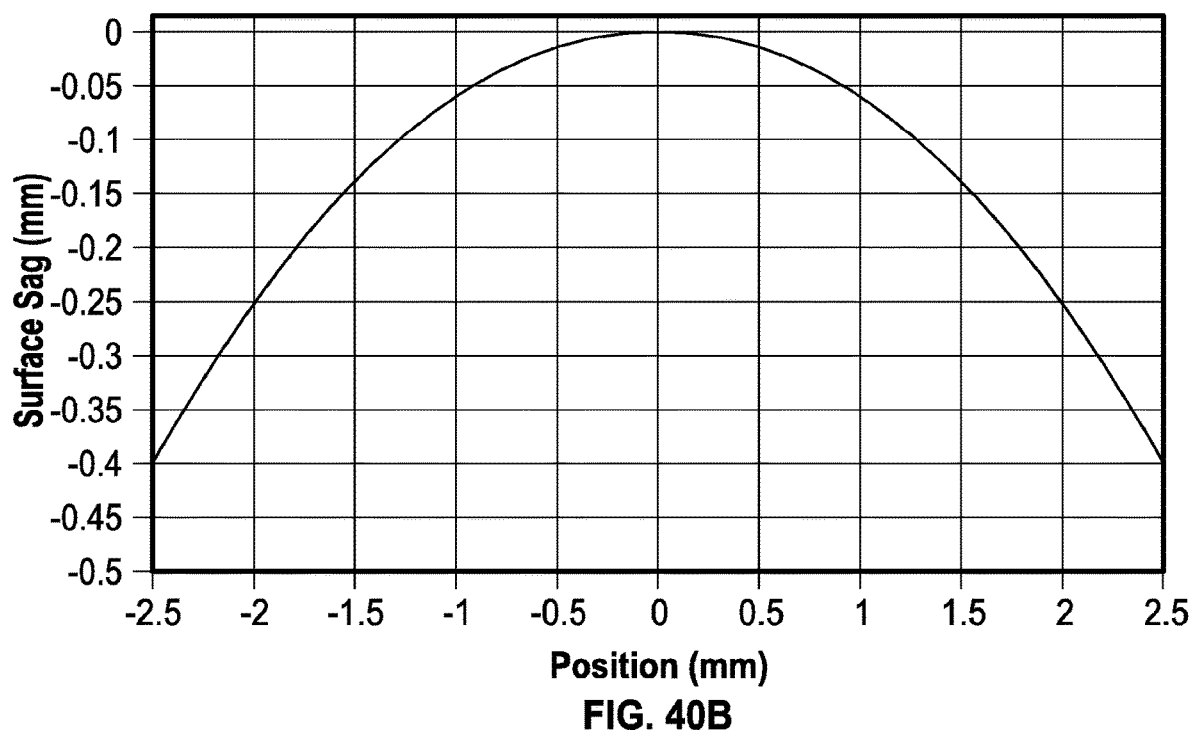
Figure 40C:
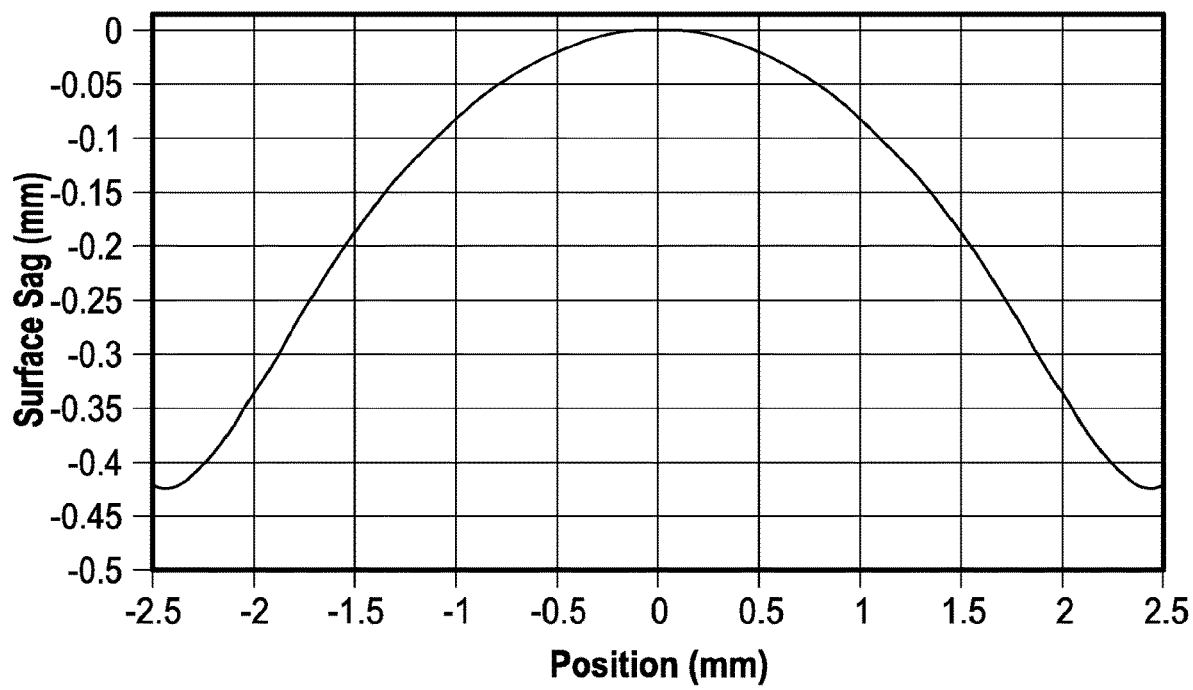
Figure 40D:
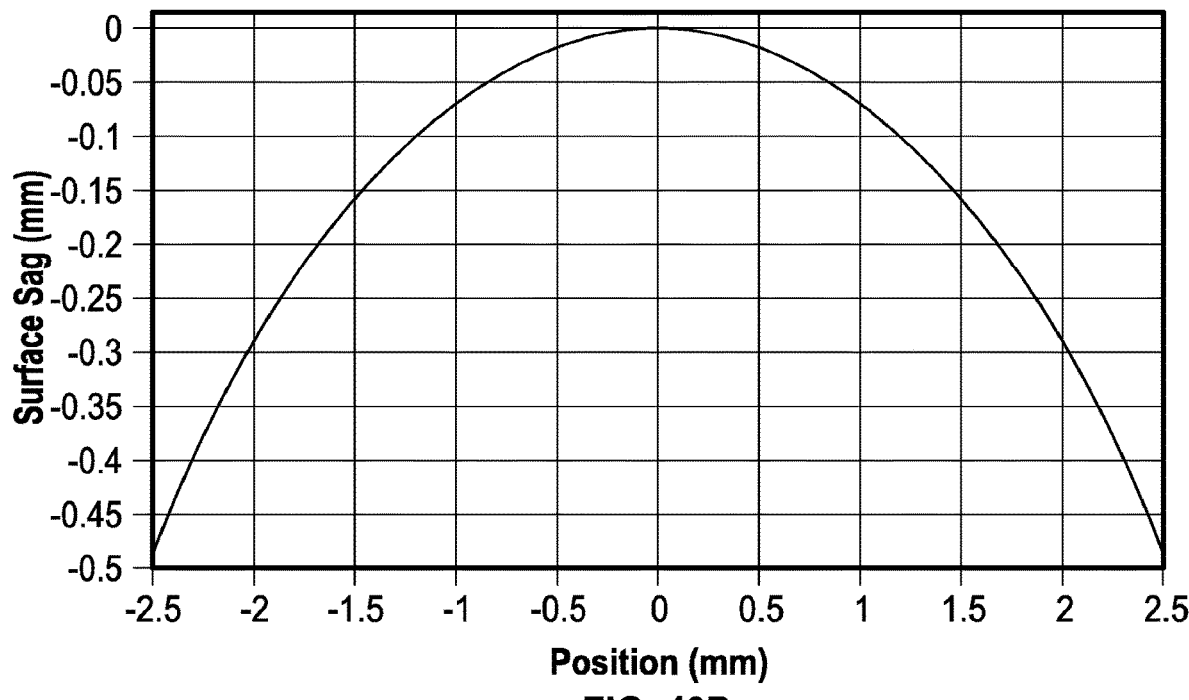
Figure 40E:
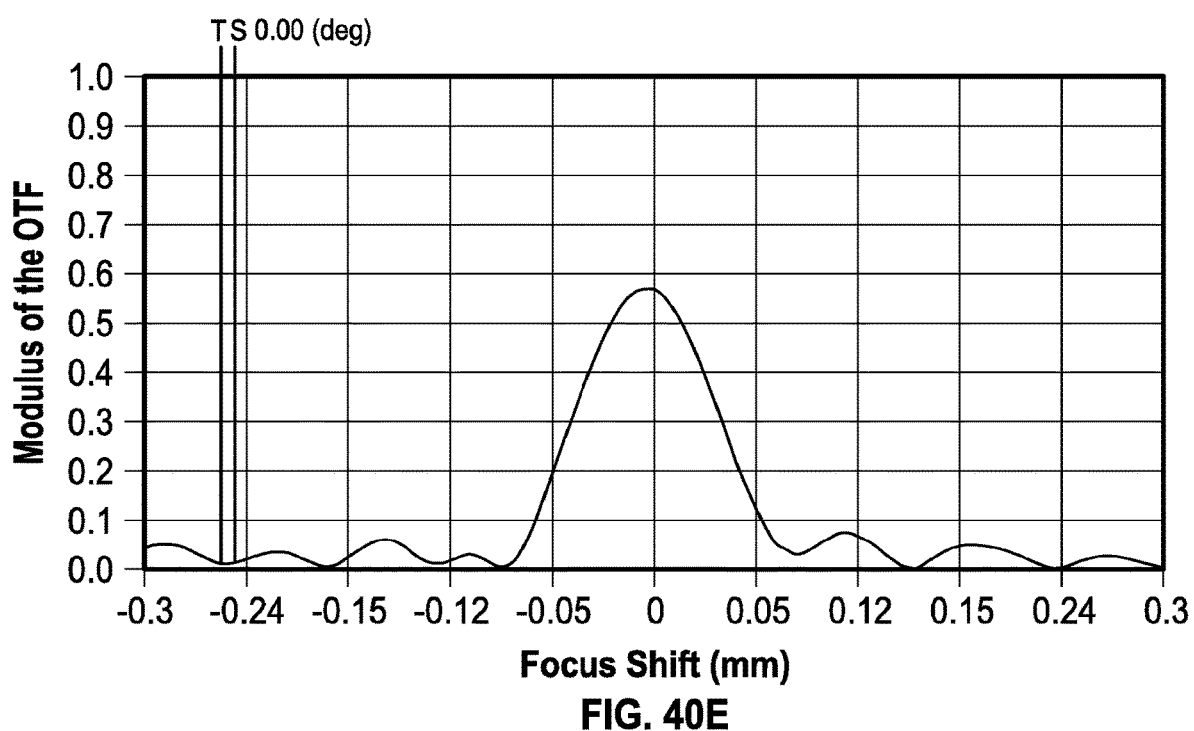

FIG. 40A illustrates the surface sag of a first surface of a first optic of an accommodating dual optic IOL and FIG. 40B illustrates the surface sag of a second surface of the first optic. FIG. 40C illustrates the surface sag of a first surface of a second optic of the accommodating IOL and FIG. 40D illustrates the surface sag of a second surface of the second optic. FIG. 40E illustrates the through-focus MTF at a spatial frequency of 100 cycles/mm in green light for a 5 mm pupil provided by the accommodating dual optic IOL.

Figure 41:
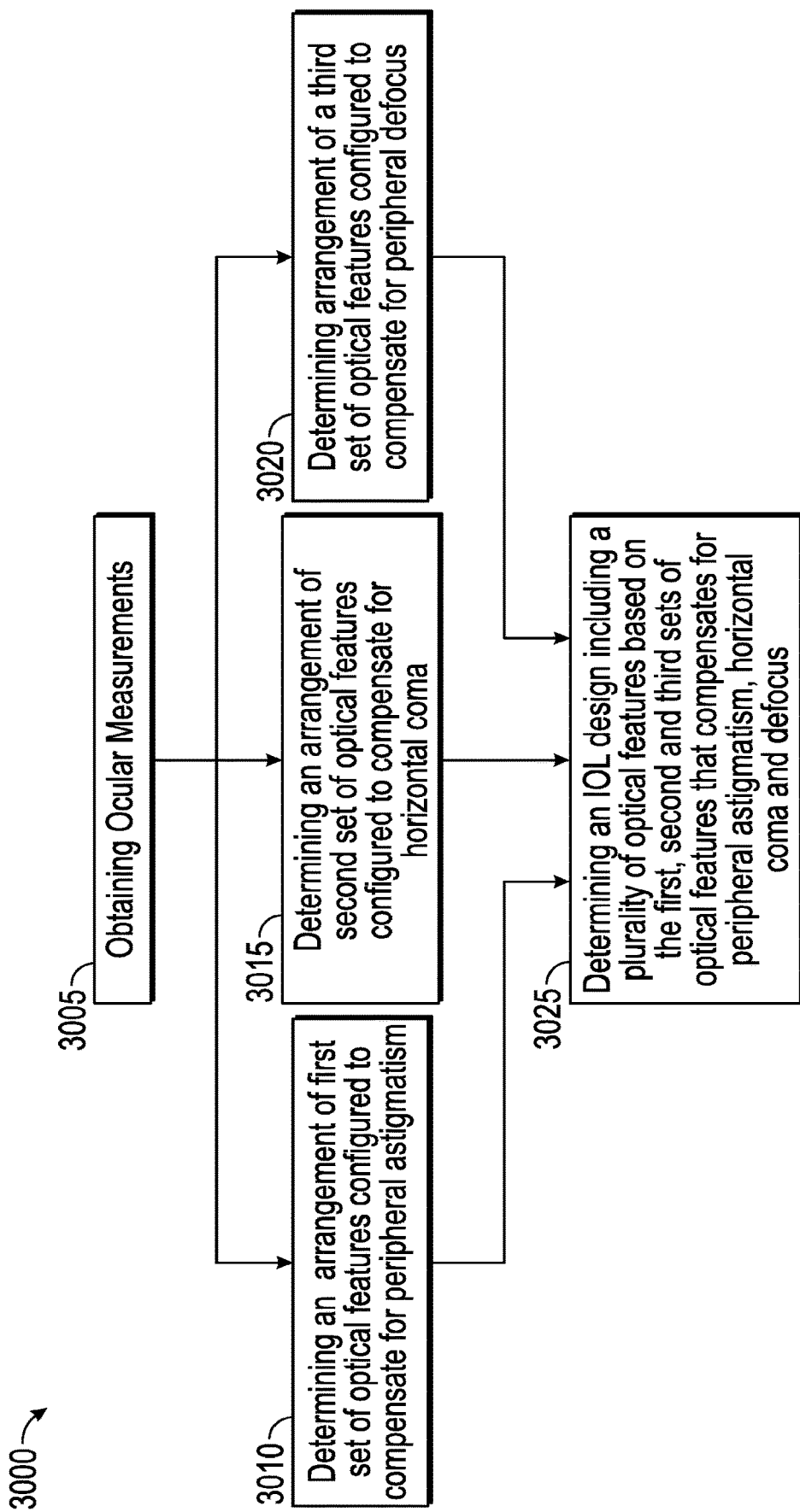

FIG. 41 is a flow chart of a method of designing an IOL to compensate for peripheral aberrations.

Figure 42:
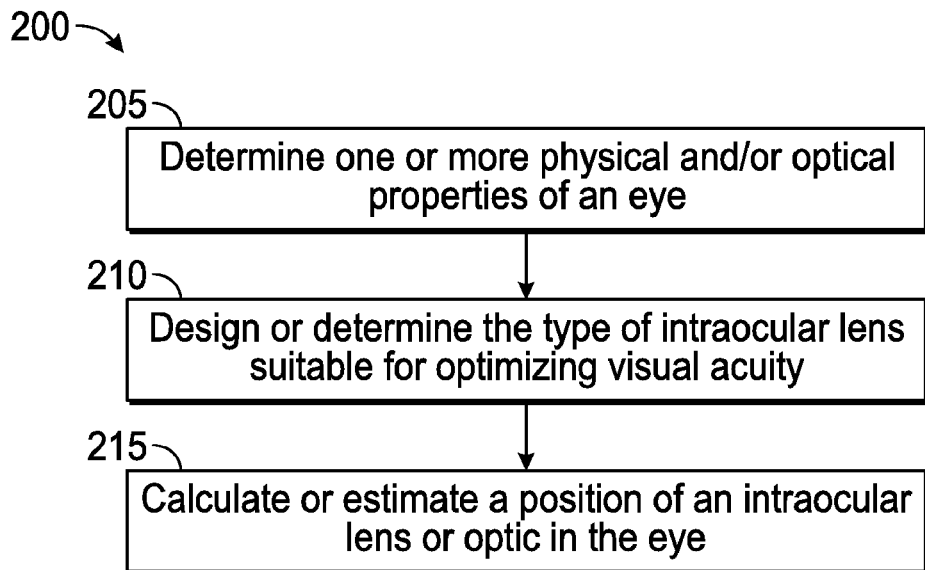

FIG. 42 is a flow chart of an implementation of a method to estimate the position of an IOL or an optic implanted in the eye.

Figure 43:
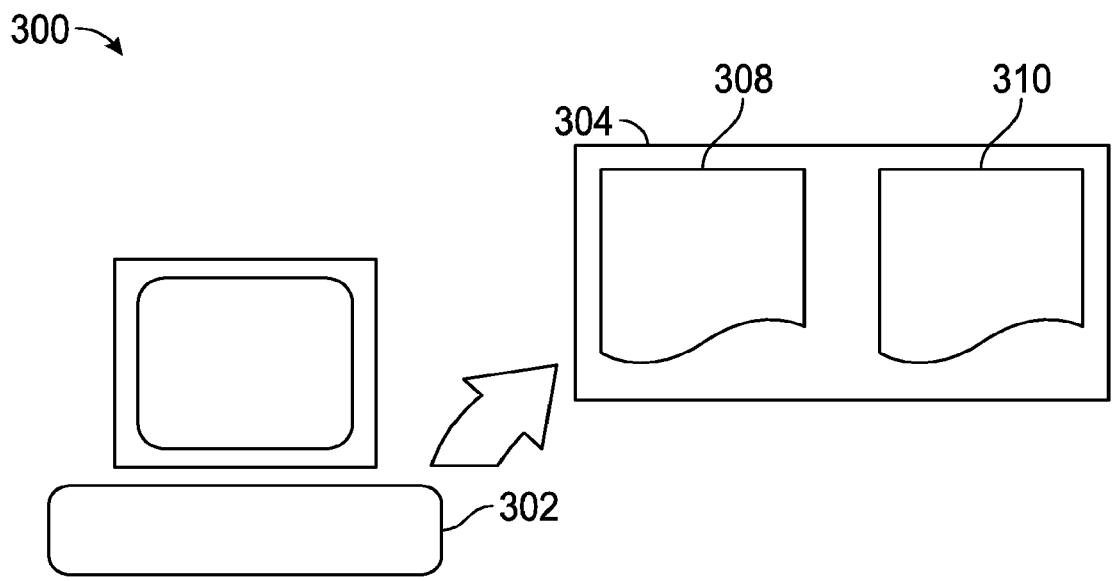

FIG. 43 is a graphical representation of the elements of computing system for selecting an ophthalmic lens.

DETAILED DESCRIPTION

The present disclosure generally provides devices, systems, and methods for improving or optimizing peripheral vision by reducing peripheral aberrations. Peripheral aberrations is a broad term and is intended to have its plain and ordinary meaning, including, for example, aberrations which occur outside of the central visual field, such as from light directed to peripheral or high field angle retinal areas. Peripheral aberrations can include, for example and without limitation, spherical aberrations, astigmatism, coma, field curvature, distortion, defocus, and/or chromatic aberrations. As disclosed herein, improving or optimizing peripheral vision includes reducing peripheral aberrations while maintaining good on-axis visual quality, or good visual quality at or near the central visual field.

Although, the implementations described herein are directed towards implantable intraocular lenses; it is understood that embodiments disclosed herein may be applied directly, or indirectly, to other types of ophthalmic lenses including, but not limited to, corneal implants, corneal surgical procedures such as LASIK or PRK, contact lenses, and other such devices. In some embodiments, various types of ophthalmic devices are combined, for example, an intraocular lens and a LASIK procedure may be used together to provide a predetermined visual outcome. Embodiments disclosed herein may also find particular use with multifocal or accommodating intraocular lenses.

The terms "power" or "optical power" are used herein to indicate the ability of a lens, an optic, an optical surface, or at least a portion of an optical surface, to focus incident light for the purpose of forming a real or virtual focal point. Optical power may result from reflection, refraction, diffraction, or some combination thereof and is generally expressed in units of Diopters. One of ordinary skill in the art will appreciate that the optical power of a surface, lens, or optic is generally equal to the refractive index of the medium (n) of the medium that surrounds the surface, lens, or optic divided by the focal length of the surface, lens, or optic, when the focal length is expressed in units of meters.

The angular ranges that are provided for eccentricity of the peripheral retinal location in this disclosure refer to the visual field angle in object space between an object with a corresponding retinal image on the fovea and an object with a corresponding retinal image on a peripheral retinal location.

Phakic and Pseudophakic Eyes

Figure 1:
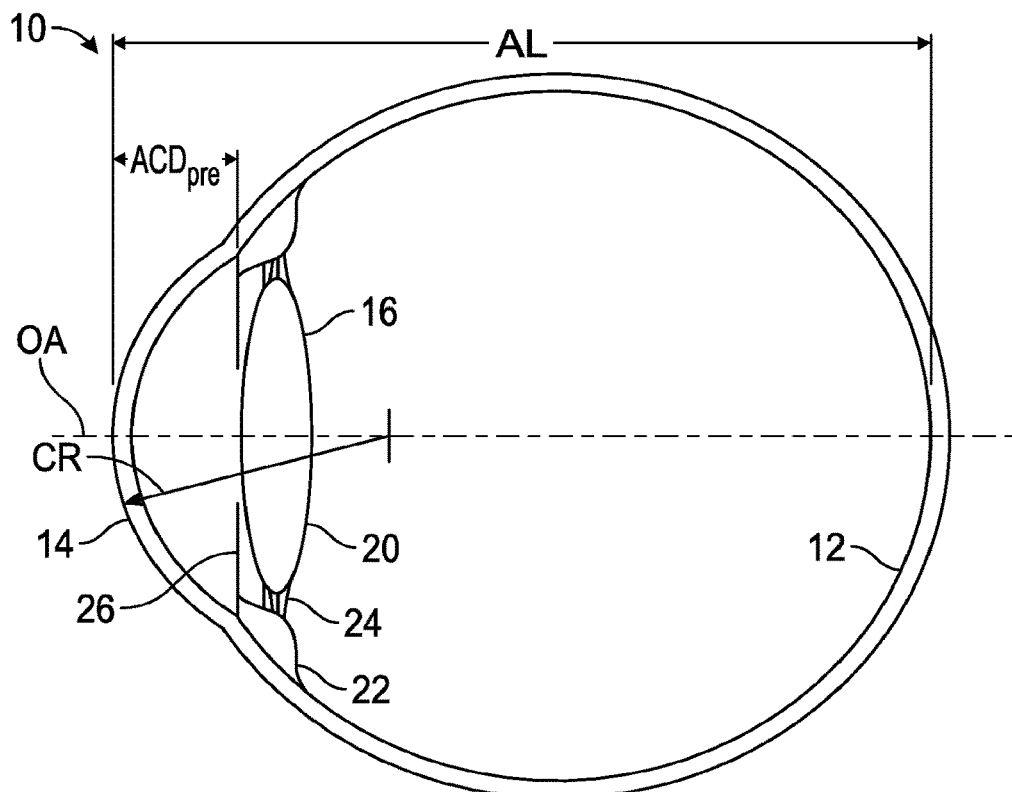
FIG. 1 is a cross-sectional view of a phakic eye containing a natural crystalline lens.

Embodiments disclosed herein may be understood by reference to FIG. 1, which is a cross-sectional view of a phakic eye with the natural crystalline lens, an eye 10 comprises a retina 12 that receives light in the form of an image that is produced by the combination of the optical powers of a cornea 14 and a natural crystalline lens 16, both of which are generally disposed about an optical axis OA. As used herein, an "anterior direction" is in the direction generally toward the cornea 14 relative to the center of the eye, while a "posterior direction" is generally in the direction toward the retina 12 relative to the center of the eye.

The natural lens 16 is contained within a capsular bag 20, which is a thin membrane that completely encloses the natural lens 16 and is attached to a ciliary muscle 22 via zonules 24. An iris 26, disposed between the cornea 14 and the natural lens 16, provides a variable pupil that dilates under lower lighting conditions (mesopic or scotopic vision) and contracts under brighter lighting conditions (photopic vision). The ciliary muscle 22, via the zonules 24, controls the shape and position of the natural lens 16, which allows the eye 10 to focus on both distant and near objects. Distant vision is provided when the ciliary muscle 22 is relaxed, wherein the zonules 24 pull the natural lens 16 so that the capsular bag 20 is generally flatter and has a longer focal length (lower optical power). Near vision is provided as the ciliary muscle contracts, thereby relaxing the zonules 24 and allowing the natural lens 16 to return to a more rounded, unstressed state that produces a shorter focal length (higher optical power).

The optical performance of the eye 10 also depends on the location of the natural lens 16. This may be measured as the spacing between the cornea 14 and the natural lens which is sometimes referred to as the anterior chamber depth prior to an ocular surgical procedure, ACDpre.

Figure 2:
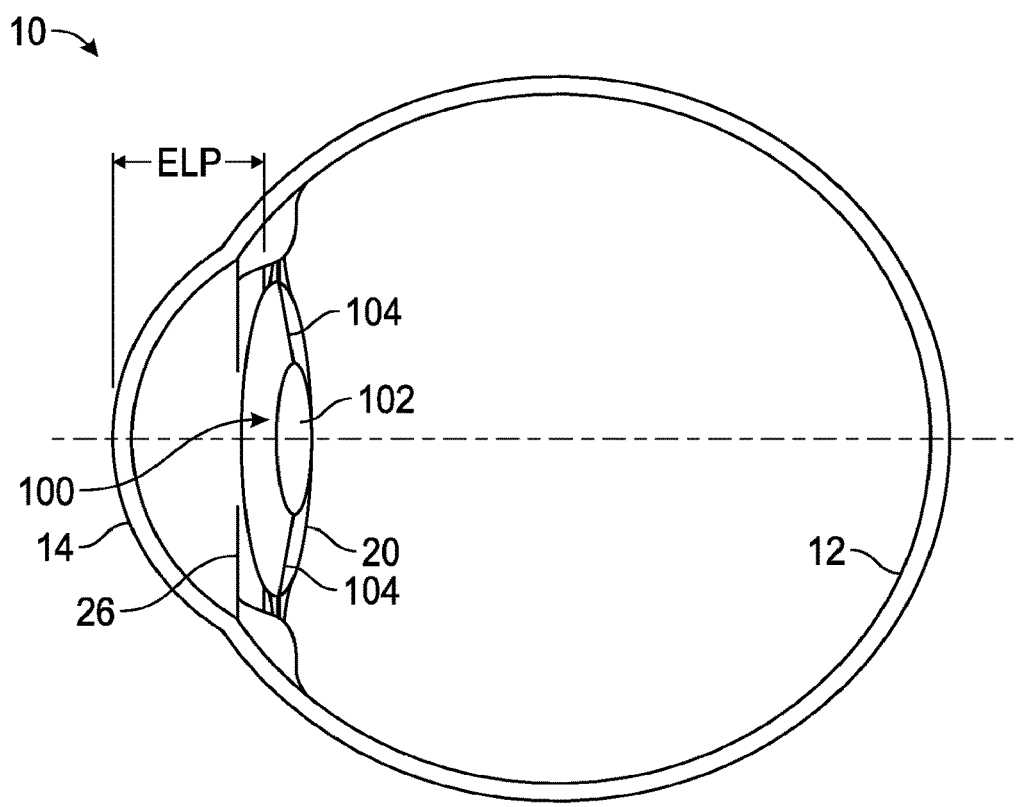
FIG. 2 is a cross-sectional view of a pseudophakic eye containing an intraocular lens.

Referring additionally to FIG. 2, which is a cross-sectional view of a pseudophakic eye 10, the natural crystalline 16 lens has been replaced by an intraocular lens 100. The intraocular lens 100 comprises an optic 102 and haptics 104, the haptics 104 being generally configured to position the optic 102 within the capsular bag 20, where ALP refers to the actual lens position. Numerous configurations of haptics 104 relative to optic 102 are well-known within the art and embodiments disclosed herein may be applied to any of these. For purposes of the embodiments disclosed herein, the location of the intraocular lens is measured as the spacing between the iris and the anterior surface of the lens. For example, a lens can have a principal plane that is posterior to the anterior lens surface, e.g., a distance P. For such an example lens, where the disclosure refers to a distance of the lens of behind the iris, e.g., a distance L, the principal plane of the lens is a distance P+L behind the iris. To provide example values, where the principal plane is about 0.4 mm behind the anterior lens surface and the lens is about 1.5 mm behind the iris, the principal plane of the lens would then be about 1.9 mm behind the iris. As discussed above, the location of the principal plane of the lens can vary depending on the shape factor of the IOL. Accordingly, for embodiments of lenses with different shape factors, the principal plane can be located at a distance different from 0.4 mm from the anterior surface of the lens.

Placement of the Principal Plane of an IOL

Figure 3:
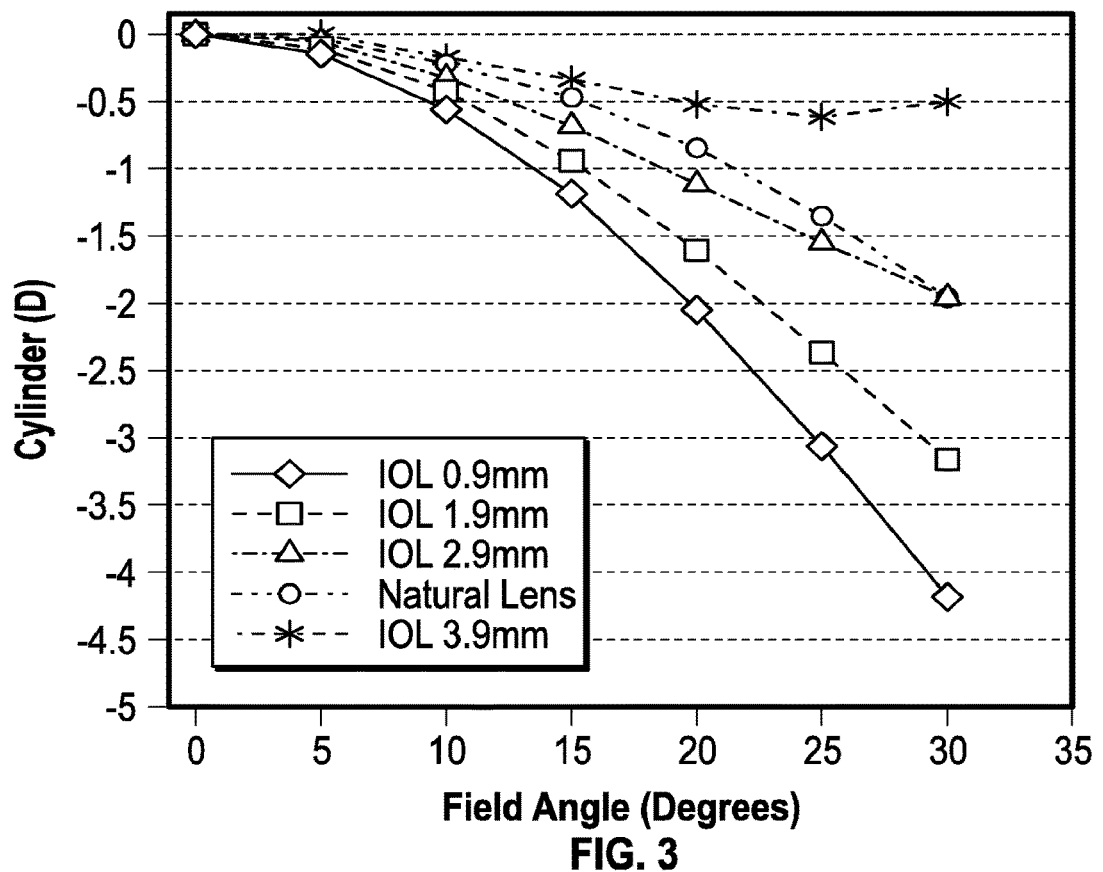
FIG. 3 is a graph illustrating peripheral astigmatism with the field angle in degrees and cylinder in diopters.
Figure 4:
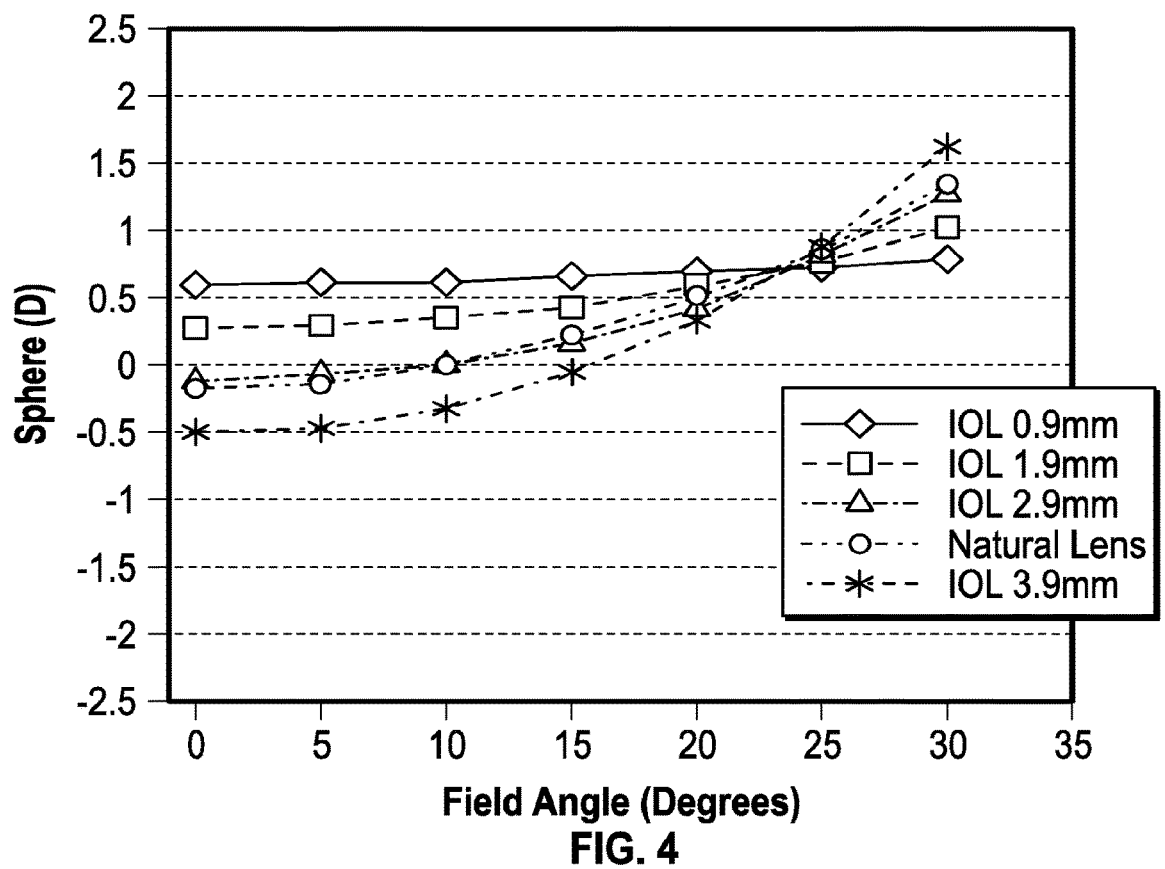
FIG. 4 is a graph illustrating peripheral astigmatism with the field angle in degrees and sphere in diopters.
Figure 5:
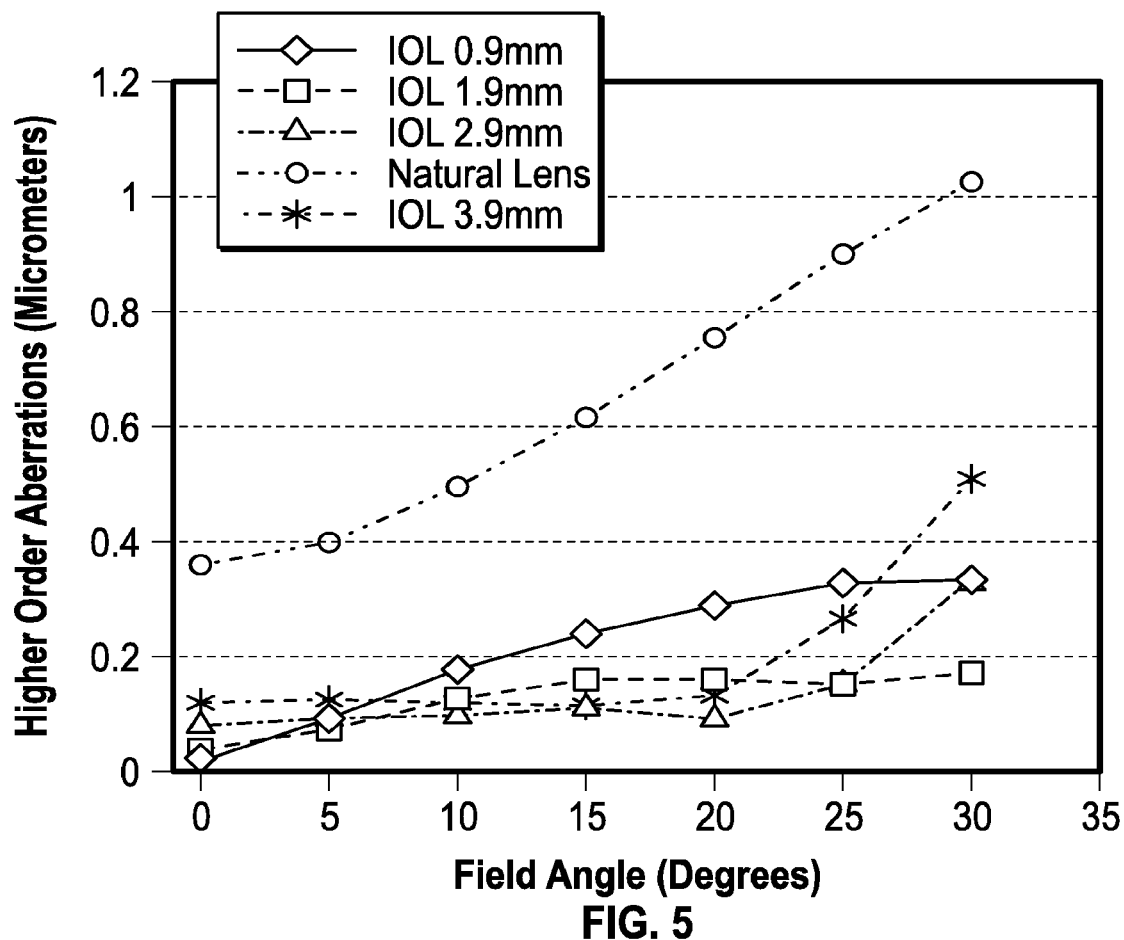
FIG. 5 is a graph illustrating peripheral astigmatism with the field angle in degrees and higher order aberrations in micrometers.

In one embodiment, the principal plane of the lens is moved posteriorly or closer to the nodal point of the eye as compared to standard IOLs. As seen in FIGS. 3-5, placing the IOL posteriorly improves peripheral vision. For purposes of the calculations detailed in FIGS. 3-5 an eye model described in the non-patent literature "Off-axis aberrations of a wide-angle schematic eye model," by Escudero-Sanz, I., & Navarro, R. "Off-axis aberrations of a wide-angle schematic eye model, J. Opt. Soc. Am. A. Opt. Image Sci. Vis., vol. 16 (8), pp. 1881-1891, 1999 was used. The entire contents of the non-patent literature are incorporated herein by reference.

The peripheral aberrations of the natural eye were calculated according to this reference and are disclosed in FIGS. 3-5 as the "natural lens." The natural lens was replaced by a standard monofocal IOL. For an average eye, the axial position of the principal plane of the lens is typically about 0.9 mm behind the iris. The peripheral refraction (sphere and cylinder) were then calculated for different axial positions of the IOL (as measured from the iris). As used herein, the term peripheral refraction includes spherical and cylindrical aberrations or errors.

The graphs show that the peripheral astigmatism is reduced considerably when the lens is placed further posteriorly in the eye (FIG. 3), while having limited impact on peripheral sphere (FIG. 4), and higher order aberrations (FIG. 5). As used herein, the term higher order aberrations is a RMS value of higher order aberrations, such as, for example, coma and trefoil. The graphs also show that when the lens is placed about 2.9 mm behind the iris (which is about 2.0 mm posterior to the current normal position of an IOL), the peripheral refraction (sphere and astigmatism) is about the same as that of the natural eye. As current IOLs are located more or less at the equator of the capsular bag, a position of 2.0 mm more posteriorly means that the lens is positioned about against the vitreous. Since the natural lens is about 4.5 mm thick, there is space to place the IOL further posteriorly.

Various lens haptic/optic configurations may be implemented in order to place the optic further posteriorly. For example the haptics may be anteriorly angled such that when the IOL is placed in the eye, the optic portion is vaulted posteriorly. "Virtual" posterior placement of the IOL may be achieved by changing the shape factor of the IOL such that the distribution power of the lens is such that more power is on the posterior side. For a single optic, for example, this can be done using a meniscus lens, having negative power at the anterior surface and positive power at the posterior surface. For a dual optic design, for example, this can be achieved by having an anterior lens with a negative power, and a posterior lens with a positive power. Increasing the lens thickness is another option disclosed herein. As will be described in greater detail herein, moving the principal plane relative to the pupil, which acts as a stop in the eye's optical system, affects peripheral aberrations based on a framework which can be used to tailor parameters of IOL optics to reduce peripheral aberrations while maintaining good on-axis optical quality.

Yet another option is to provide an optical system making use of 3 lenses. Such lens systems are capable of optimizing field curvature, as well as astigmatism.

In another embodiment, an artificial pupil may be implanted between the lenses of a dual lens system, or posterior to an IOL or lens combination. Such an artificial pupil can advantageously reduce peripheral aberrations arising from the cornea.

In some embodiments, peripheral vision is improved by employing binocular summation. To optimize peripheral vision using binocular summation one eye is implanted with an IOL that improves or optimizes sagittal image quality in the periphery, and the other is implanted with an IOL that improves or optimizes tangential image quality. Various approaches of the sagittal/tangential image quality improvement or optimization are described below. One approach to improve sagittal/tangential image quality includes configuring the IOL such that the modulus of the optical transfer function (MTF) for sagittal rays and tangential rays is above a threshold.

In some embodiments, peripheral vision is improved by implanting an IOL with a toric component. In various embodiments, the toric component can be included even when the patient has good central vision and does not need an astigmatic or toric correction and. The IOL with the toric component has a higher optical power along the vertical axis corresponding to an axis of 90-degrees using the common negative cylinder sign convention than the horizontal axis corresponding to an axis of 180-degrees using the common negative cylinder sign convention. Such a lens can improve image quality in the horizontal field of view. This can be beneficial to patients, as most relevant visual tasks are carried out in the horizontal field of view.

Additionally, the IOL can be configured to provide an astigmatic correction along the vertical and/or the horizontal axis. An astigmatic correction when combined with the correct higher order aberrations can provide a good on-axis depth of focus, which can advantageously reduce the need for glasses to improve near distance vision.

Extended Depth of Focus

In another embodiment, peripheral vision is improved by an IOL design having an extended depth of focus in the periphery. There are several methods to extend the depth of focus that can be applied. Below is a specific example, based on extending the depth of focus with a single ring microstructure.

Figure 6:
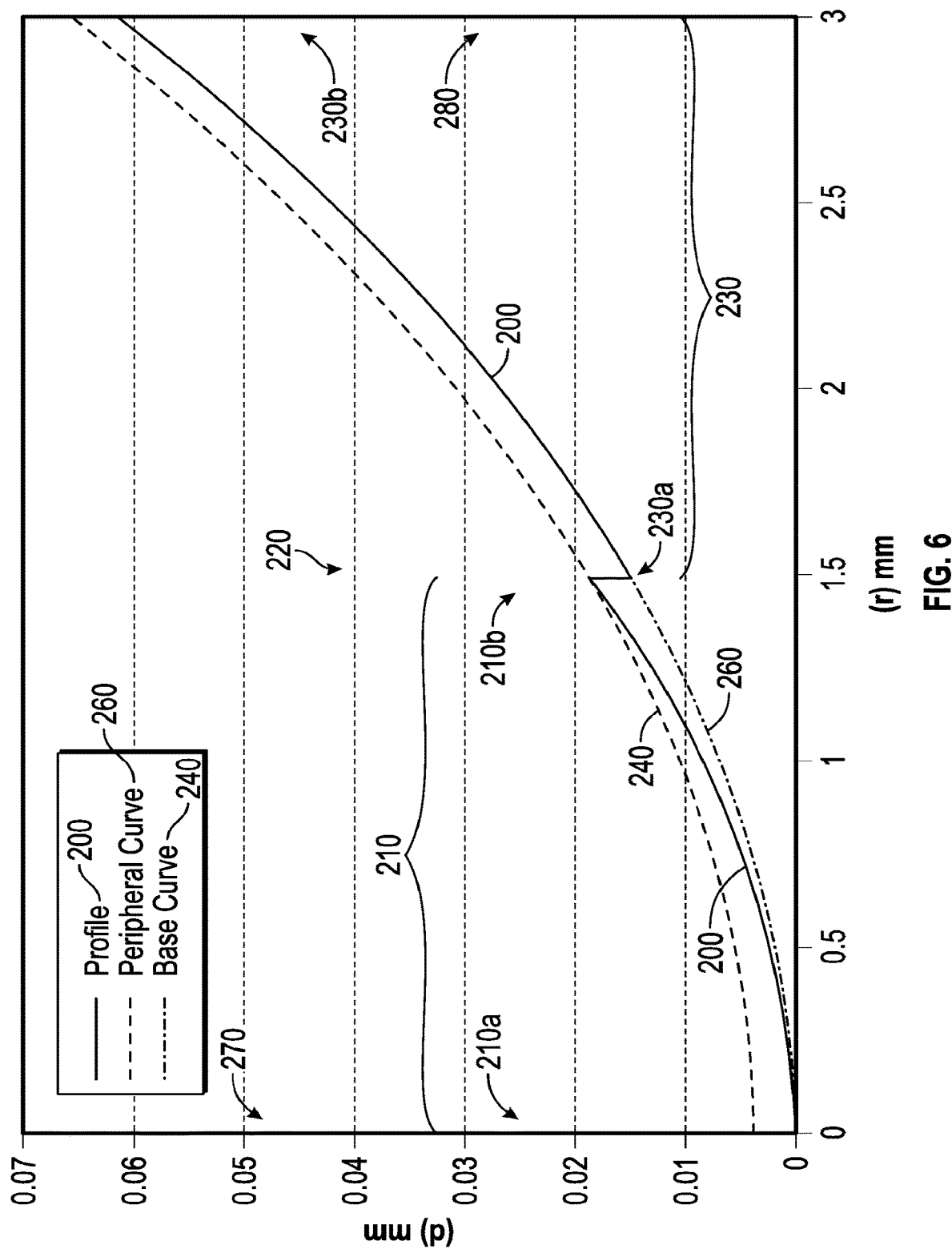
FIG. 6 shows aspects of a lens including a ring microstructure.

FIG. 6 discloses a single ring microstructure for extending depth of focus as detailed in U.S. patent application Ser. No. 12/971,506 (now U.S. Pat. No. 8,430,508), which is incorporated by reference herein in its entirety. Only half of an optical surface profile 200 of the lens is shown in FIG. 6, although since the single ring microstructure is rotationally symmetric, the other half is a mirror image that complements the lens at the left side of FIG. 6. Profile 200 of the single ring surface includes an inner portion or single ring 210, a step or transition 220, and an outer portion 230. Inner portion 210 extends between a central location 270 of profile 200 and transition 220, and outer portion 230 extends between transition 220 and a peripheral location 280 of profile 200. Central location 270 is typically disposed at the optical axis. Transition 220 is disposed at a distance of about 1.5 mm from the optical axis, and peripheral location 280 is disposed at the diameter of the clear aperture of the lens, here at a distance of about 3.0 mm from the optical axis. In some cases, transition 220 can be disposed at a distance from the optical axis that is within a range from about 0.5 mm to about 2.0 mm, and peripheral location 280 can be disposed at a distance from the optical axis that is within a range from about 2.0 to about 3.5 mm, or bigger (for example, for contact lenses, the ranges would be scaled due to the larger sizes of the contact lens compared to an IOL).

As shown in FIG. 6, the surface height or sag (d) from a reference plane perpendicular to the optical axis, of each point on the lens profile is plotted against the radial distance (r) from the optical axis of the lens. As shown here, the value of displacement or total sag (d) can have a value within a range from about 0 mm to about 0.07 mm. The total sag can depend on the refractive shape of the surface and can have a value, for an IOL, of typically between 0 mm and about 2 mm, or to about minus 2 mm, in cases where the surface is concave.

Extended Depth of Focus—Inner Portion

Inner portion or echelette 210 includes a center 210a and a peripheral edge 210b. At center or central section 210a of inner portion 210, the sag (d) of inner portion 210 is substantially equivalent to the displacement or sag (d) of peripheral curve 260. At peripheral edge 210b, the sag (d) of inner portion 210 is substantially equivalent to the sag (d) of diffractive base curve 240. Where radial distance (r) is zero, sag (d) of inner portion 210 is equivalent to the value of the peripheral curve 260. The value of sag (d) between radial distance zero and radial distance at the peripheral edge 210b, for example at 1.5 mm, gradually and smoothly changes from the value of peripheral curve 260 (at r=0) to diffractive base curve 240 (at 1-1.5 mm) in a parabolic fashion. As shown here, inner portion 210 can present a parabolic shape, for example as described in Equation 4a of Cohen, Applied Optics, 31:19, pp. 3750-3754 (1992), incorporated herein by reference herein in its entirety.

Extended Depth of Focus—Transition

At the peripheral edge 210b, where the radial distance (r) is 1.5 mm, the value of sag (d) steps or changes from the value of diffractive base curve 240 to the value of peripheral curve 260. Where radial distance (r) corresponds to transition 220, sag (d) of inner portion 210 is equivalent to the value of the diffractive base curve 240. Relatedly, the displacement of the profile 200 approaches that of the peripheral curve 260 as the radial distance increases from a value of zero to a value of about 1.5 mm. The value of the offset can be determined along the vertical axis. The offset value may be selected depending on the amount of phase delay. According to one embodiment, the inner portion 210 and the outer portion 230 may not end up at the same vertical height at position 210b/230a. One way to connect these two endpoints is by using a straight vertical line. As shown here, the diffractive transition step provides a sharp step in the profile. In some cases the transition is characterized by a step height having a value within a range from about 0.5 microns and about 4 microns.

Extended Depth of Focus—Outer Portion

Outer portion 230 includes an inner or central edge 230a and a peripheral edge 230b. At inner edge 230a, the sag (d) of outer portion 230 is substantially equivalent to the sag (d) of peripheral curve 260. At peripheral edge 230b, the sag (d) of outer portion 230 remains substantially equivalent to the sag (d) of peripheral curve 260. The value of sag (d) for the outer portion 230 of profile 100 between radial distance 1.5 mm and radial distance 3.0 mm is equivalent to the value of peripheral curve 260. The sag of the profile 200 and the peripheral curve 260 are approximately equivalent between radial distance values of 1.5 mm and 3.0 mm.

Extended Depth of Focus—Example Embodiments

In addition to a single ring, limited ring extended depth of focus embodiments, as disclosed in application Ser. No. 12/971,607, can be achieved by adding a limited number of echelettes to the above detailed single ring microstructure. In general such limited ring embodiments comprise a limited number of echelettes that are either adjacent or non-adjacent to the inner central echelette and may or may not be separated by a refractive region. It should be appreciated that any variation of single and limited ring embodiments falls within the scope of embodiments disclosed herein.

Figure 7:
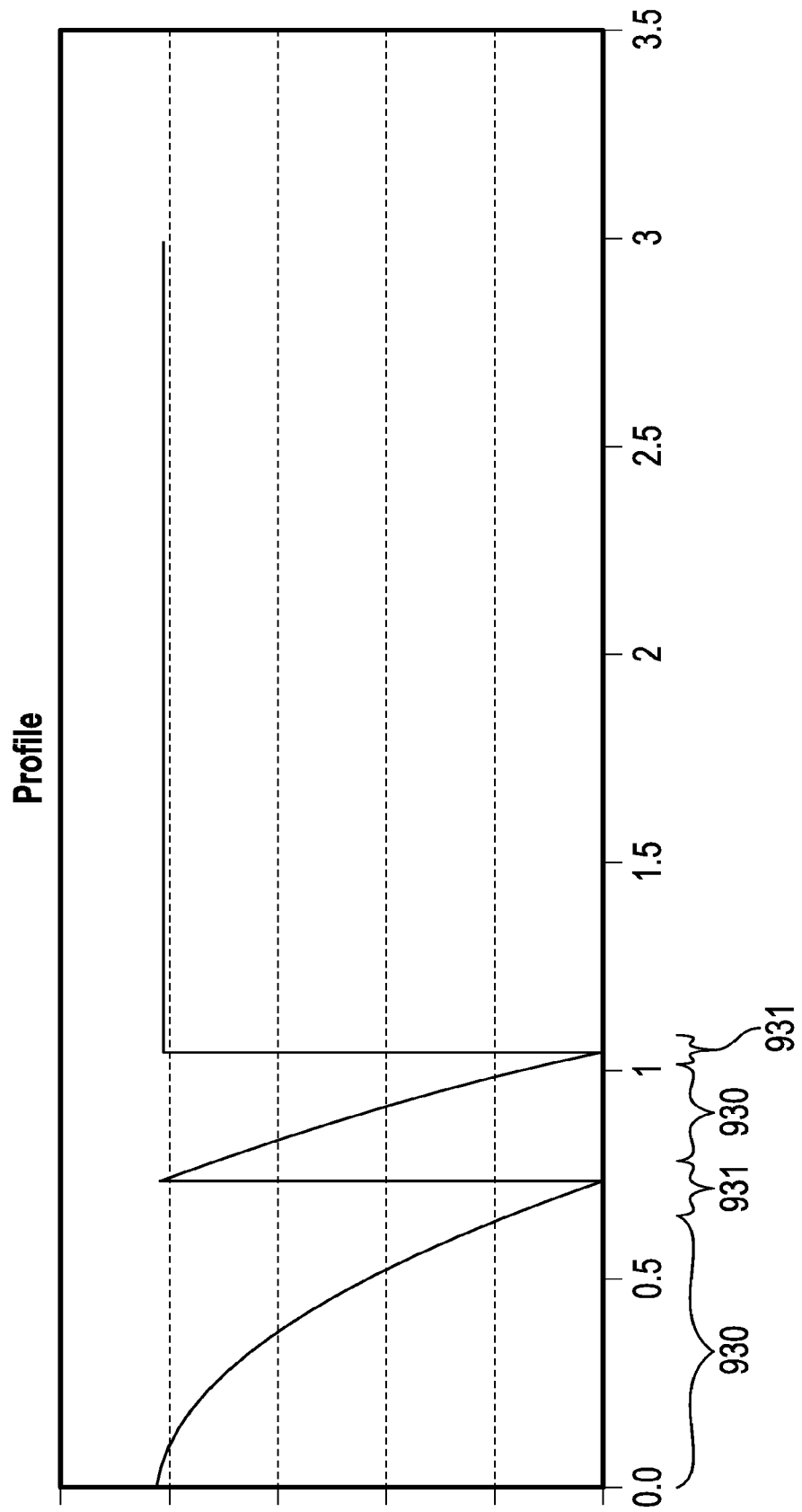
FIG. 7 illustrates aspects of a diffractive lens.

FIG. 7 provides a graphical representation of a portion of a lens diffractive profile with a central echelette and one peripheral adjacent echelette according to some embodiments. In FIG. 7, the height of the surface relief profile (from a plane perpendicular to the light rays) of each point on the echelettes surface is plotted against the distance from the optical axis of the lens. The echelettes can have a characteristic optical zone 930 and transition zone 931. Optical zone 930 can have a shape or downward slope that may be linear when plotted against p as shown in FIG. 7. When plotted against radius r, optical zone 930 can have a shape or downward slope that is parabolic. Central and peripheral echelettes can have a surface area that is between 0.7 and 7 $mm^2$. For example, the echelettes may have a surface area that is 0.85 $mm^2$. An outer (refractive) zone can follow the base radius with a fixed offset. Example embodiments include peripheral echelette(s) that are similar in shape (e.g., elliptical) and variable step height as the central echelette. Of course, this disclosure includes those embodiments where the peripheral echelette(s) differ in shape and/or variable step height as compared to the central echelette.

Extended Depth of Focus—Peripheral Aberrations

Figure 8:
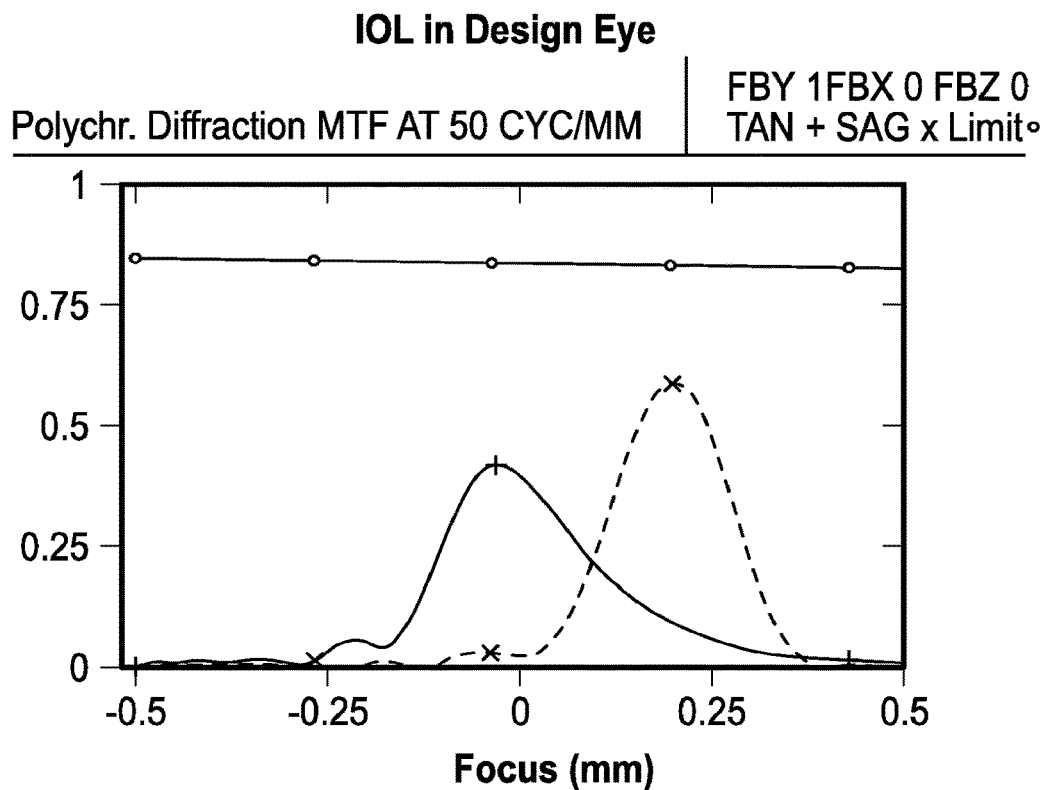
FIG. 8 is a graph illustrating through-focus MTF at different axial focus positions.
Figure 9:
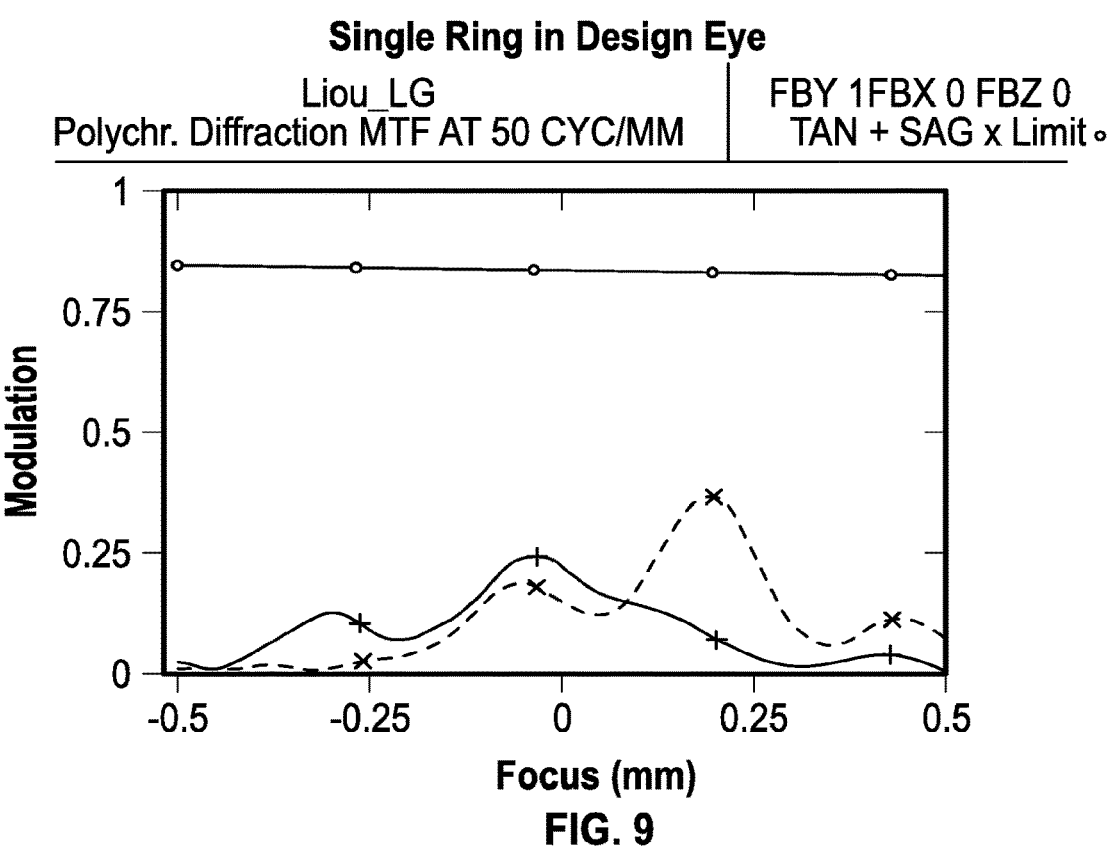
FIG. 9 is a graph illustrating through-focus MTF at different axial focus positions.

The aforementioned structures can extend the depth of focus and reduce aberrations in the peripheral field. As seen in FIGS. 8 and 9, the extended depth of focus IOL has no significant peripheral astigmatism as compared to a standard monofocal IOL. For the purpose of analysis, a standard monofocal chromatic IOL was used in a schematic eye model, based on the following Liou & Brennan publication: Liou, H. L., & Brennan, N. A., "Anatomically accurate, finite model eye for optical modeling," J. Opt. Soc. Am. A, 14 (8), 1684-1695 1997 (which is incorporated herein in its entirety), with a retinal radius of curvature of 12 mm, a pupil diameter of 3 mm. The through focus white light MTF at 50 c/mm was calculated at the periphery and at 15 degrees eccentricity in 2 perpendicular orientations (tangential and sagittal). As seen in FIG. 8, the peak MTF value for tangential rays and the peak MTF value for sagittal rays do not occur at the same axial position. In fact, as observed from FIG. 8, the monofocal IOL has a reduced sagittal MTF at the tangential peak, and vice versa. This can be attributed to peripheral astigmatism. As seen in FIG. 9, the single ring extended depth of focus IOL, at zero defocus, had approximately equal MTF in both orientations, indicating a reduction in astigmatism. Thus, the monofocal IOL has greater astigmatism in the periphery as compared to the extended depth of focus IOL.

While other solutions may have a very specific influence on a particular peripheral wavefront aberration, an extended depth of focus in the periphery is relatively insensitive to specific aberrations and dimensions of the eye of a particular patient. Additionally, such an extended depth of focus solution also has an increased tolerance to possible issues related to surgically induced changes of aberrations, as well as IOL placement issues. Therefore, it can be used as a one-size-fits-all solution.

Analogously, movement of the IOL posteriorly or closer to the nodal point also provides for a more general solution as opposed to an IOL which has a particular design to address particular aberrations.

Multifocal IOLs

In another embodiment, a multifocal IOL is used to induce multiple foci of the same optical power. In other words, unlike traditional multifocal IOLs, the add power for the particular embodiment described herein is about zero. Instead, the multiple foci focus images on different parts of the retina, thus producing optimal optical quality at those regions of the retina that are healthy, or alternatively in a ratio that optimizes vision.

Figure 10:
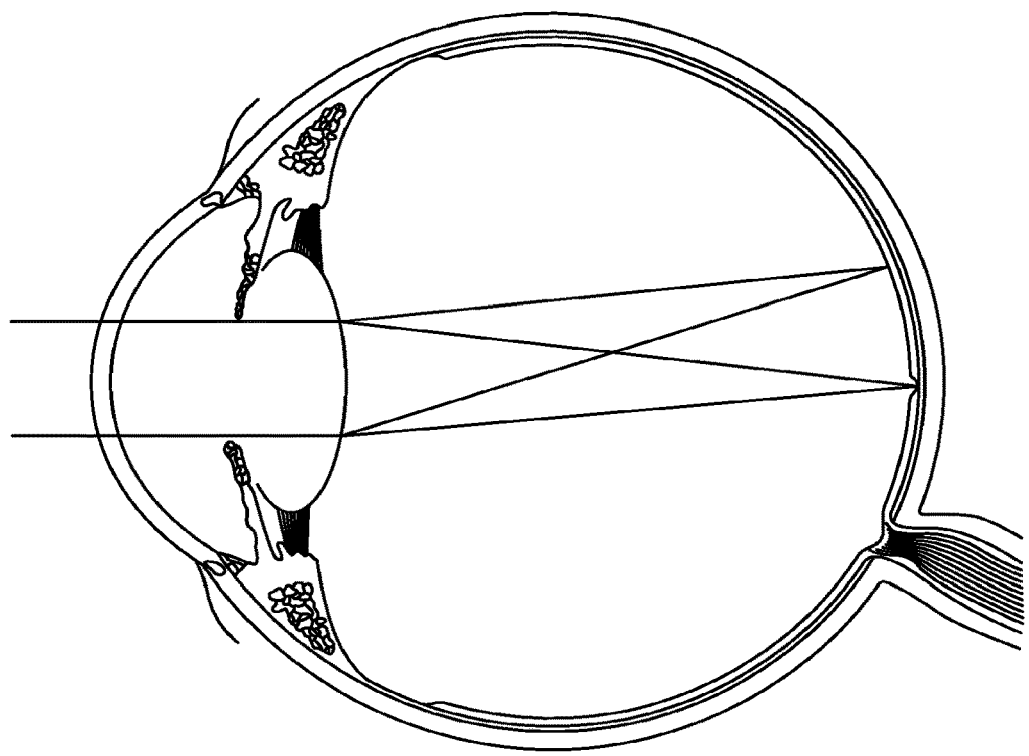
FIG. 10 shows aspects of a multifocal IOL in an eye.

In some embodiments, a multifocal IOL has at least 2 zones, wherein the at least 2 zones have about the same optical power. The inner zone may be a spherical lens producing a good central focus on the central fovea. The outer zone(s) consist of a spherical lens combined with a prism, producing a good focus at a predetermined spot in the periphery as seen in FIG. 10. One skilled in the art will appreciate that many zone variations are possible including, but not limited to concentric or non-concentric variations. Additionally more than two images may be formed, and the light distribution may be varied in order to optimize visual acuity. The multifocal lens has a small add power, typically smaller than about 6 diopters. Preferably, the multifocal lens has an add power of less than about 4 diopters. In another preferred embodiment, the multifocal lens has an add power of less than about 2 diopters. Preferably the add power is about equal to zero.

Similar effects may be achieved through the use of outer zone(s) which are aspheric. Alternatively, diffractive optics may be used to induce multiple foci on different parts of the retina with the same optical power. This disclosure also contemplates implementations of IOLs including a bag-filling lens with a gradient refractive index to achieve results similar to the results discussed above.

Consideration of Retina Characteristics

In another embodiment, characteristics of the retina are considered for the IOL design. In particular, a geographical map of retinal functionality and/or the retinal shape are combined with other ocular geometry, such as pupil size and location, axial positions of the pupil, lens, and retina, anterior and/or posterior corneal aberrations, tilts and decentrations within the eye, and angle kappa. The shape of the retina may be measured using MRI, tomography, or other techniques apparent to those skilled in the art. A metric function can be used to improve or optimize the IOL design, where the metric function includes both central and peripheral optical quality. Optical quality is measured taking into account any particular damage to the fovea or other region of the retina. For example, the size and location of a possible retinal scotoma may be determined. If the patient has a central scotoma which covers the entire fovea, then maximizing visual acuity in the peripheral region would be included into the optical design.

Such maximization of peripheral vision would be dependent on the peripheral threshold MTF, which depends ganglion cell size and spacing. For example, the large ganglion cell size seen in the periphery limits the spatial resolution. Thus, improving the optical quality at spatial frequencies beyond the sampling limit cutoff imposed by the ganglion cells would not improve resolution acuity. Therefore, any optimization procedure for resolution can be limited to be below that cutoff frequency.

However, if detection acuity is considered, optimization beyond the retinal cutoff frequency is beneficial for peripheral vision.

Additionally, recent data suggests that peripheral optics in myopes differs from that in emmetropes. For example, myopes can have relative peripheral hyperopia, whereas emmetropes can have relative peripheral emmetropia or relative peripheral myopia. Thus, customizing an IOL to account for particular peripheral aberrations while balancing peripheral MTF may lead to improved overall vision.

Improving Peripheral Vision Provided by IOLs

Figure 11:
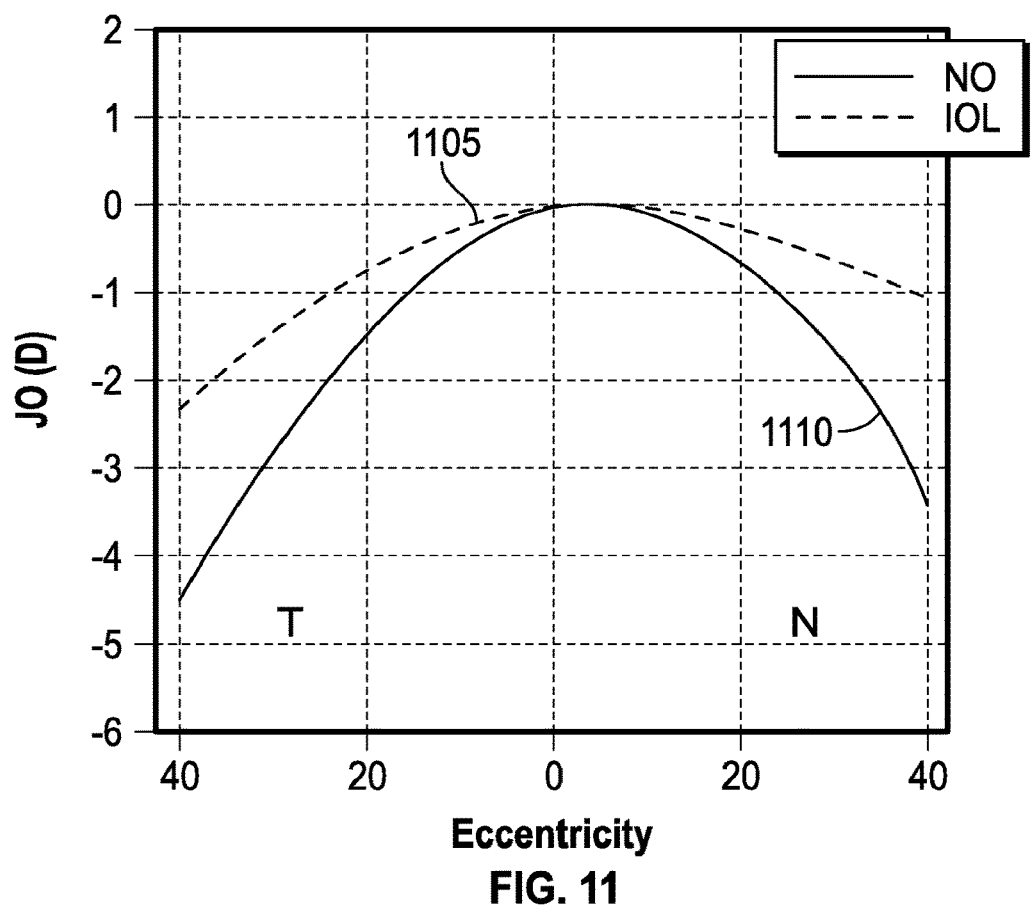
FIG. 11 depicts the astigmatism in the natural lens and an implementation of an artificial IOL as a function of eccentricity in degrees.

As discussed above, a human eye can suffer from many impairments, such as, for example presbyopia, myopia, hypermetropia, degraded peripheral vision, etc. A patient suffering from presbyopia has reduced ability to focus on objects at near distance. Patients implanted with IOLs to correct for various impairments can have degraded peripheral vision (relative to a natural eye) caused by the IOL due to off-axis astigmatism, peripheral defocus, and higher order aberrations such as coma. As used herein, on- and off-axis refer respectively to being on (e.g., along or near) or off (e.g., away from) the optical axis of the eye or the center of vision (e.g., the fovea). FIG. 11 depicts the astigmatism in the natural lens and an implementation of a typical IOL as a function of eccentricity in degrees. As used herein, eccentricity refers to the angular distance from the center of the visual field, such as for example, the central fovea. The curve represented by the reference numeral 1105 depicts the astigmatism in the natural lens as a function of eccentricity and the curve represented by the reference numeral 1110 depicts the astigmatism in an implementation of a typical IOL as a function of eccentricity. As observed from FIG. 11, the curve 1110 has lower optical power at higher values of eccentricity as compared to the curve 1105 indicating that implementing a typical IOL degrades peripheral vision of the recipient as compared to the natural lens. Degraded peripheral vision can result in optical errors on detection acuity, low contrast resolution acuity, and contrast sensitivity function in the periphery. Degraded peripheral vision may adversely affect daily tasks where good peripheral vision is needed, such as scene gist recognition, car driving and locomotion. Accordingly, there is a need for improving the peripheral vision provided by typical IOLs.

Several methods of improving peripheral vision provided by IOLs are discussed herein. For example, peripheral vision can be improved by an IOL design having an extended depth of focus in the periphery as discussed above. As another example, peripheral vision can be improved by tailoring parameters of the IOL based on calculations of peripheral aberrations using stop-shift equations (discussed below) which can be used to calculate aberrations resulting from lens modifications which alter the relative displacement of an aperture (e.g., the pupil) and the principal plane of the lens. As another example, peripheral vision can be improved by modifying a shape factor and/or asphericity of a dual-optic lens IOL to reduce peripheral aberrations while maintaining substantially constant the total optical power of the IOL. As another example, peripheral vision can be improved through the use of binocular summation by implanting an IOL that optimizes sagittal image quality in the periphery in one eye and implanting another IOL that optimizes tangential image quality in the other eye. Peripheral vision can also be improved by configuring the implanted IOL to be at least partially toric so as to provide an astigmatic correction in the horizontal visual field. These approaches are discussed in further detail below.

Using Stop-Shift Equations to Tailor IOLs

Image quality produced by artificial IOLs, and particularly off-axis image quality, can be improved or optimized by varying different parameters of the IOL. The variation of such parameters can improve off-axis image quality by reducing peripheral aberrations while maintaining good on-axis image quality. Examples of parameters that can be tailored to improve peripheral vision after implantation of an IOL include, for example, a shape factor of the lens, through geometrical radius and material refractive index or indexes, axial displacement of the lens or the lens' principal plane, additional apertures, or any combination of these. Modifying one or more of these parameters can consequently modify a position of the principal plane of the lens with respect to the aperture. Displacement of the principal plane of the lens relative to an aperture affects aberrations in the optical system. These effects on the aberrations can be modeled and predicted using a set of equations called stop-shift equations which provide a theoretical framework for predicting changes to aberrations when distances change between apertures (e.g., the pupil) and refractive surfaces (e.g., IOL lens elements, cornea, etc.). Accordingly, modifications can be tailored to improve or optimize one or more peripheral aberrations to improve peripheral vision relative to a typical IOL while accounting for other visual tradeoffs such as on-axis image quality.

The stop-shift equations provide a framework for calculating aberrations caused by relative movements of apertures and refractive surfaces (which includes movement of a principal plane of a lens). Without subscribing to any particular theory, the Seidel aberrations provided in Table 1 describe aberrations for a single thin lens placed in air.

TABLE 1

| Wave Aberration Coefficient | Seidel Aberrations | Name |
| --- | --- | --- |
| $W_{040}$ | $\frac{1}{8} S'_I$ | Spherical Aberration |
| $W_{131}$ | $\frac{1}{2} S'_{II}$ | Coma |
| $W_{222}$ | $\frac{1}{2} S'_{III}$ | Astigmatism |
| $W_{220}$ | $\frac{1}{4}(S'_{III} + S'_{IV})$ | Field Curvature |
| $W_{311}$ | $\frac{1}{2} S'_V$ | Distortion |
| $\delta_\lambda W_{020}$ | $\frac{1}{2} C'_L$ | Long. Chromatic Aberration |
| $\delta_\lambda W_{111}$ | $C'_T$ | Lat. Chromatic Aberration |

Table 2 expresses the Seidel aberrations as a function of structural coefficients of a lens ($\sigma_i'$). The structural coefficients change when a lens is displaced with respect to an aperture. This change is described by the stop-shift equations, listed in Table 3.

TABLE 2

| Seidel Aberration | Structural Coefficient |
| --- | --- |
| $S'_I$ | $\frac{1}{4} h^4 K^3 \sigma'_I$ |
| $S'_{II}$ | $\frac{1}{2} L h^2 K^2 \sigma'_{II}$ |
| $S'_{III}$ | $L^2 K \sigma'_{III}$ |

TABLE 2-continued

| Seidel Aberration | Structural Coefficient |
| --- | --- |
| $S'_{IV}$ | $L^2 K \sigma'_{IV}$ |
| $S'_V$ | $(2/h^2) L^3 \sigma'_V$ |
| $C'_L$ | $h^2 K \sigma'_L$ |
| $C'_T$ | $2 L \sigma'_T$ |

TABLE 3

| Remote Stop | Stop at Lens |
| --- | --- |
| $\sigma'_I$ | $\sigma_I$ |
| $\sigma'_{II}$ | $\sigma_{II} + \chi \sigma_I$ |
| $\sigma'_{III}$ | $\sigma_{III} + 2\chi \sigma_{II} + \chi^2 \sigma_I$ |
| $\sigma'_{IV}$ | $\sigma_{IV}$ |
| $\sigma'_V$ | $\sigma_V + \chi(\sigma_{IV} + 3\sigma_{III}) + 3\chi^2 \sigma_{II} + \chi^3 \sigma_I$ |
| $\sigma'_L$ | $\sigma_L$ |
| $\sigma'_T$ | $\sigma_T + \chi \sigma_L$ |

Table 4 includes structural coefficients for a thin lens in air when the stop is at the lens. In Table 4, X is the shape factor of the lens (generally calculated as $(R_p + R_a)/(R_p - R_a)$ where $R_a$ is the radius of curvature of the anterior surface of the lens and $R_p$ is the radius of curvature of the posterior surface of the lens), Y is the conjugate factor (generally calculated as $(1/L1 - 1/L2)/(1/L1 + 1/L2)$, where L1 is the distance to the object and L2 is the distance to the image. In most cases considered, the object is assumed to be at infinity, which simplifies the equation so that Y=−1, n is the index of refraction of the lens. Table 5 expresses certain material coefficients in terms of the index of refraction of the lens.

TABLE 4

| Structural Coefficient | Value |
| --- | --- |
| $\sigma_I$ | $AX^2 + BXY + CY^2 + D$ |
| $\sigma_{II}$ | $EX + FY$ |
| $\sigma_{III}$ | 1 |
| $\sigma_{IV}$ | $1/n$ |
| $\sigma_V$ | 0 |
| $\sigma_L$ | $1/V$ |
| $\sigma_T$ | 0 |

TABLE 5

| Material Coefficient | Value |
| --- | --- |
| A | $(n + 2)/[n(n - 1)^2]$ |
| B | $[4(n + 1)]/[n(n - 1)]$ |
| C | $(3n + 2)/n$ |
| D | $n^2/(n - 1)^2$ |
| E | $(n + 1)/[n(n - 1)]$ |
| F | $(2n + 1)/n$ |

The stop shift factor, $\chi$, is given by the equations below, where s is the distance between the surface and the aperture stop, which can be shifted. Ks is the power of the surface, cornea or IOL under consideration. It is noted that s>0 refers to the case of the aperture being placed behind the refracting surface or lens.

$$\chi = -K_S/[(1+Y)K_S + 2] \text{ for } s<0$$

$$\chi = K_S/[(1-Y)K_S - 2] \text{ for } s>0$$

These equations can be adapted for use in mediums other than air. For example, optical properties of a system with multiple refracting surfaces can be tailored or optimized when it is immersed in another medium other than air. For the change of medium, the following substitution can be made: $n=n_{lens}-n_{aqueous}+1$. For the multiple surfaces, the cornea can also be taken into account.

As shown by Tables 1-3, spherical aberration is unaffected by shifts in the stop position. As shown in Tables 4 and 5, spherical aberration depends on the relevant structural parameters. Coma is affected by movement when the lens has spherical aberration in the non-displaced state. Astigmatism is affected, provided there is coma or spherical aberration in the non-displaced state. Accordingly, there can be coma present which is eliminated by a shift in the relative stop position, which still supports a reduction in peripheral astigmatism. As such, both coma and astigmatism can potentially be removed by tailoring the structural parameters and/or relative stop position of an IOL.

As can be seen from the tables and the stop-shift equations, the shape factor, X, is a parameter which affects many aberrations. As a reference, the shape factor for a symmetrical lens is 0, a plano-convex lens has a shape factor of −1 or 1 (depending on its orientation), and a meniscus lens has a shape factor that is less than −1 or greater than 1. Accordingly, it can be advantageous to determine which shape factors provide greater reductions in peripheral aberrations.

Figure 12:
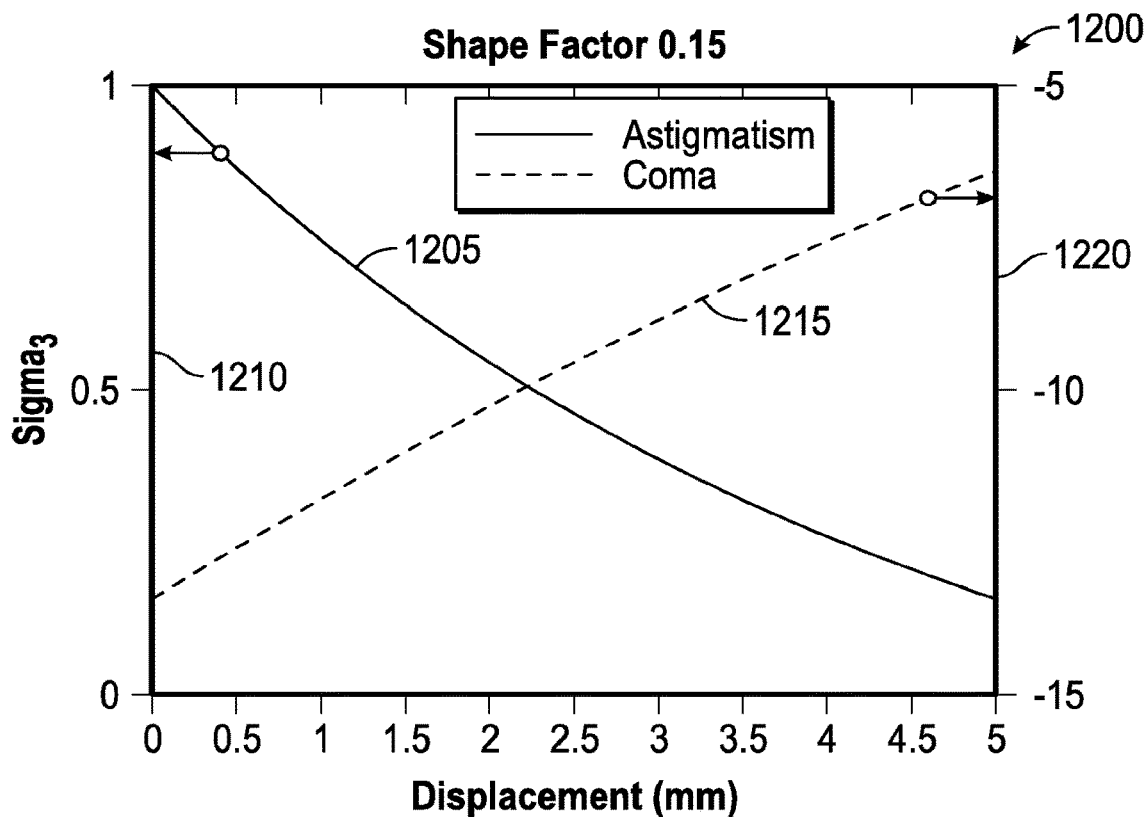
FIG. 12 is a graph illustrating astigmatism and coma as a function of displacement of an IOL with a shape factor of 0.15.
Figure 13:
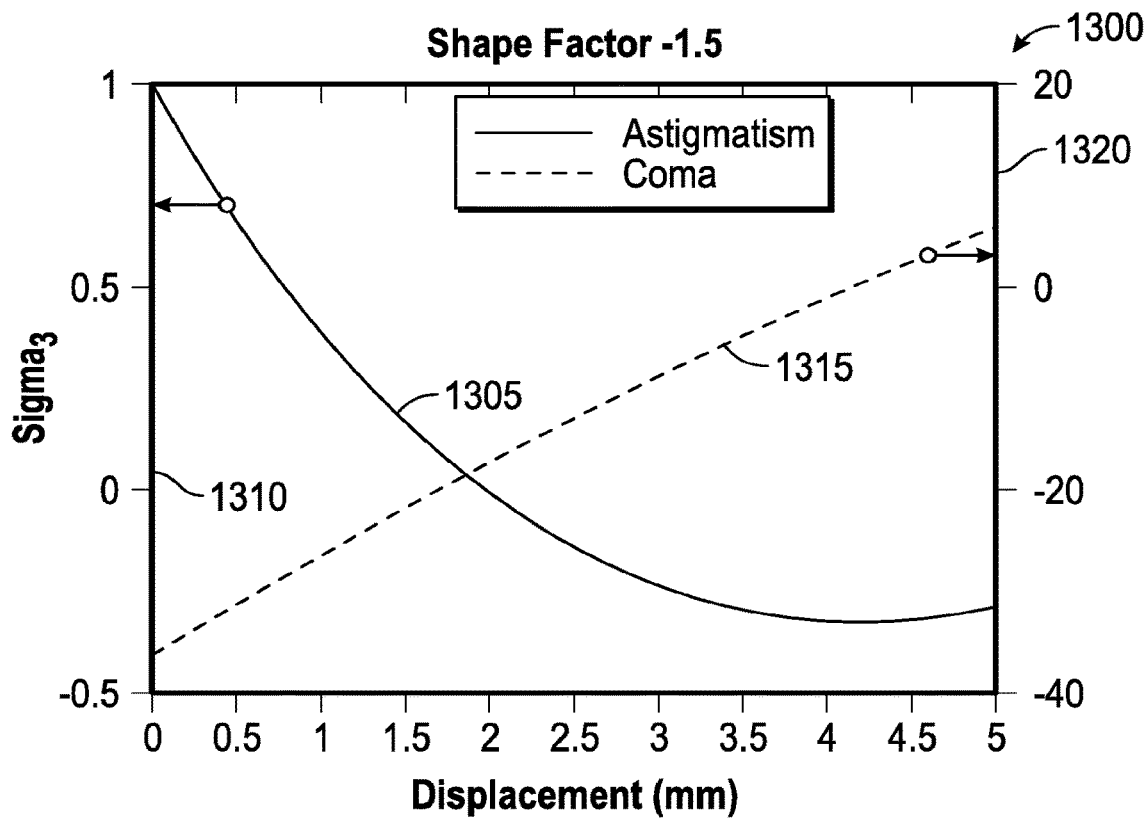
FIG. 13 is a graph illustrating astigmatism and coma as a function of displacement of an IOL with a shape factor of −1.5.

Referring now to FIGS. 12 and 13, the effects of the displacement of IOLs with different shape factors are illustrated. The graphs were produced using computer simulations based on the stop-shift concepts described herein. The graphs 1200 and 1300 show astigmatism and coma as a function of displacement of an IOL for an IOL having a shape factor of 0.15 (graph 1200) and a shape factor of −1.5 (graph 1300).

A typical IOL has a shape factor of about 0.15, so FIG. 12 illustrates the behavior of a typical IOL when it is displaced from an aperture. Astigmatism, line 1205, is plotted against the left-hand axis 1210, and coma, line 1215, is plotted against the right-hand axis 1220. As displacement increases, both astigmatism and coma approaches zero. As stated herein, the lens cannot be displaced much more than 5 mm with respect to the iris in a typical patient.

An IOL with a meniscus shape (e.g., shape factor of −1.5) improves performance with respect to astigmatism and coma relative to the typical IOL, as shown in FIG. 13, when requiring a smaller displacement for reducing astigmatism and coma. Astigmatism, line 1305, and coma, line 1315, both pass zero at particular values of displacement. By reaching negative astigmatism, the IOL can be configured to reduce or remove astigmatism caused by the cornea.

An improved or optimal displacement would be one where peripheral aberrations, such as astigmatism and coma, are reduced the most or eliminated, or where a combined aberration factor is reduced or minimized. The combined aberration factor can be a weighted sum or average of the various aberrations that are discussed herein. In some embodiments, finding an improved or optimized displacement includes accounting for both off- and on-axis image quality. The considerations for finding or calculating an improved or optimal displacement presented in this paragraph apply for finding improved or optimal shape factors or any other parameters of the IOL discussed herein.

Figure 14:
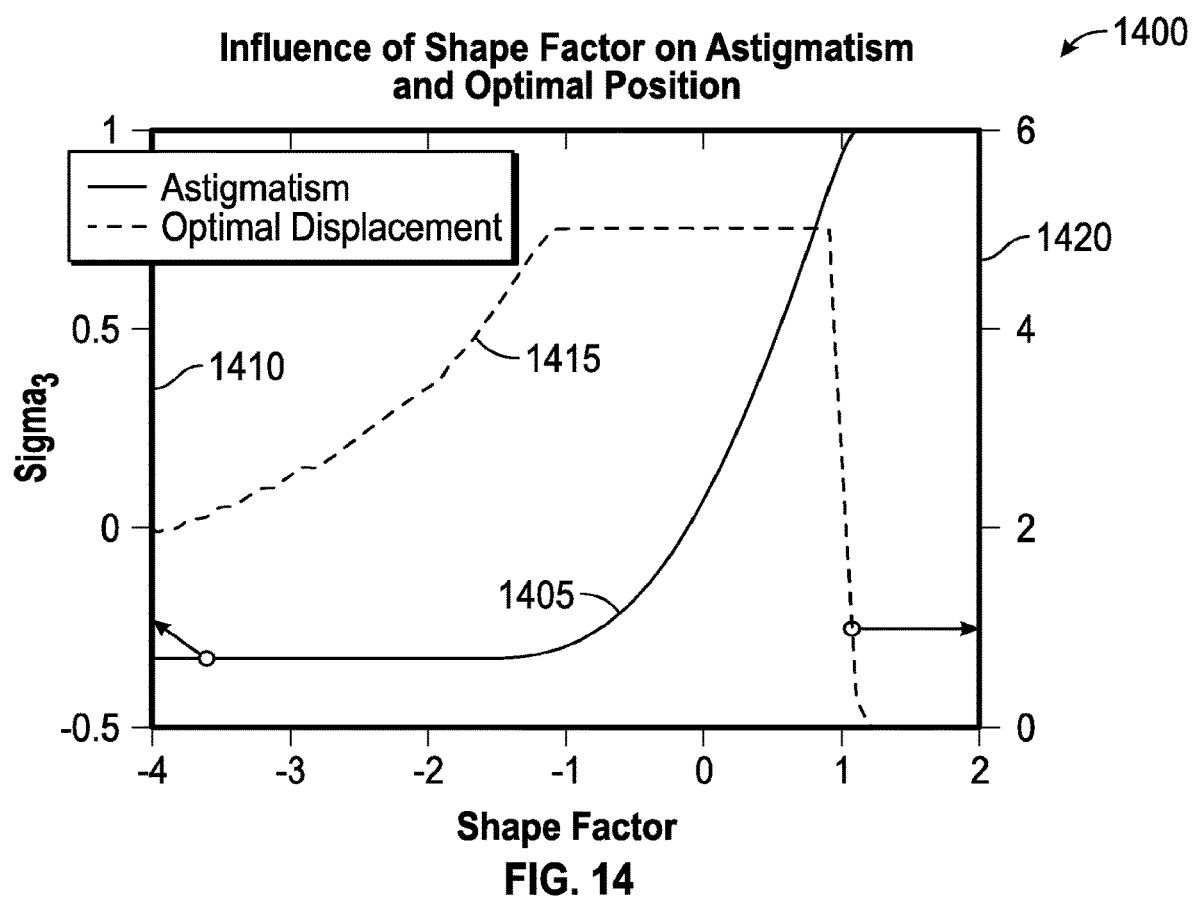
FIG. 14 is a graph illustrating the influence of shape factor on astigmatism and position of an IOL with respect to the pupil.
Figure 15A:
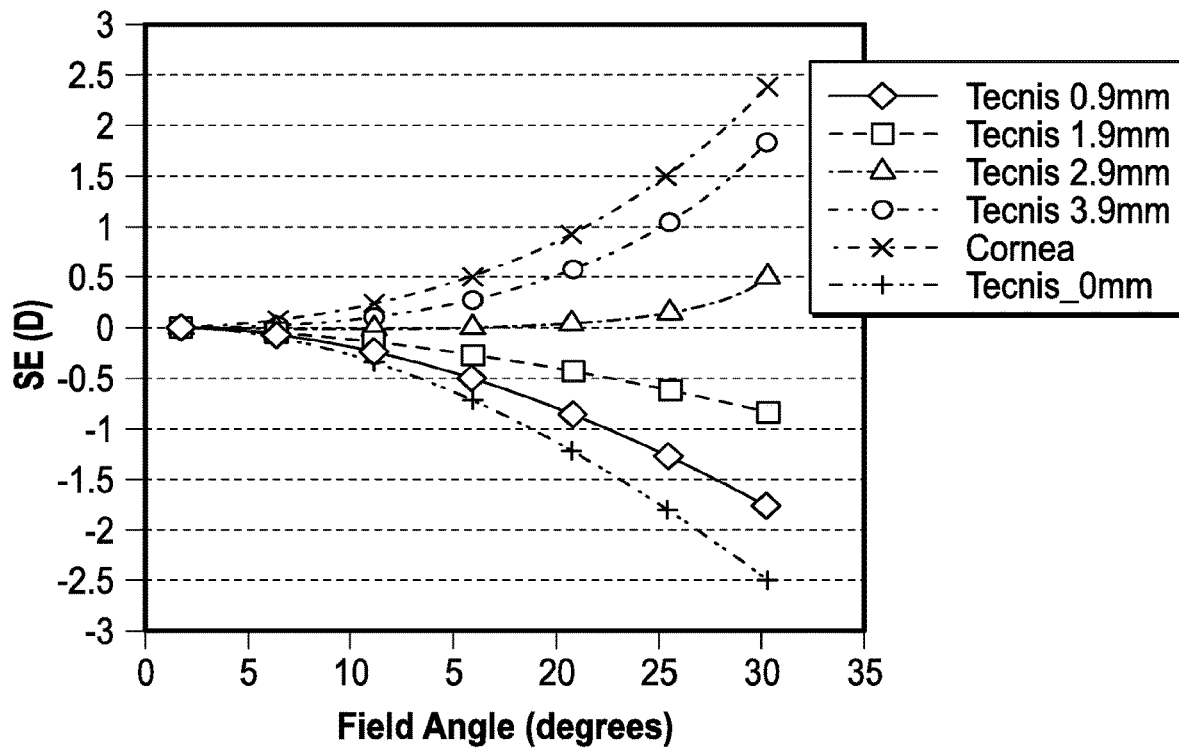
FIGS. 15A-D are graphs illustrating spherical equivalent, cylinder, spherical aberration, and coma as a function of field angle for a variety of IOL displacements.
Figure 15B:
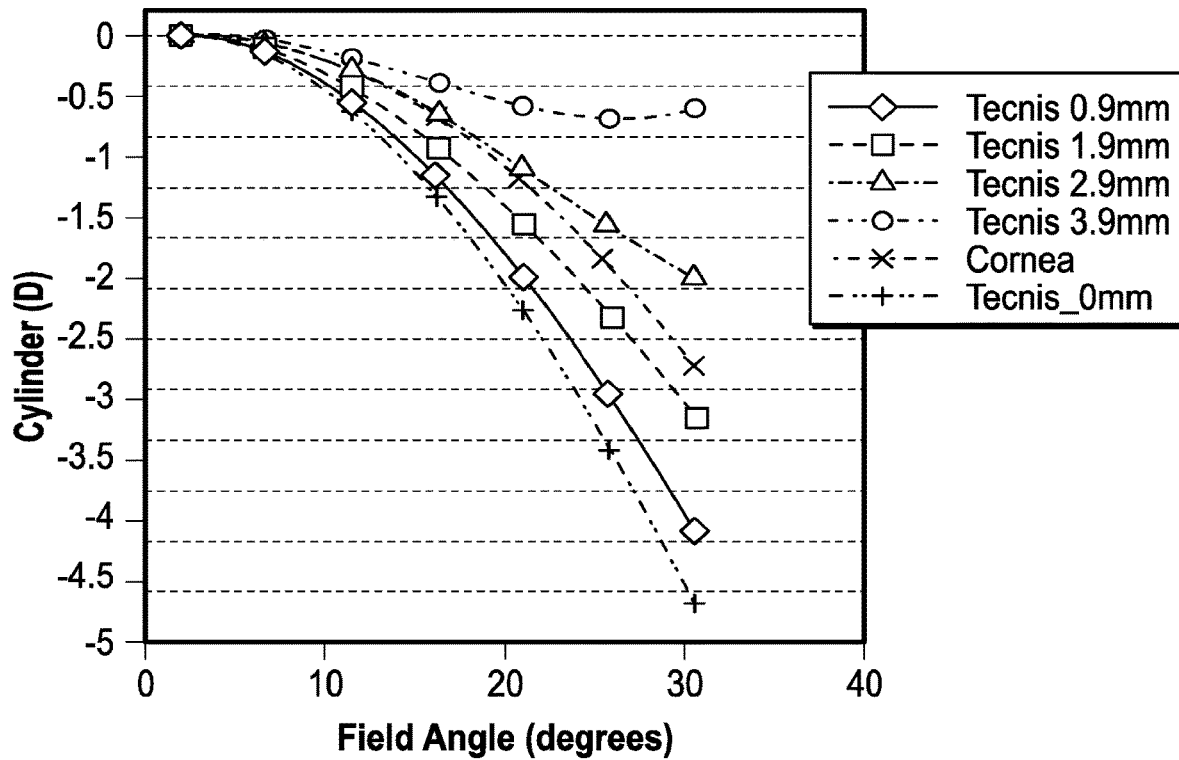
Figure 15C:
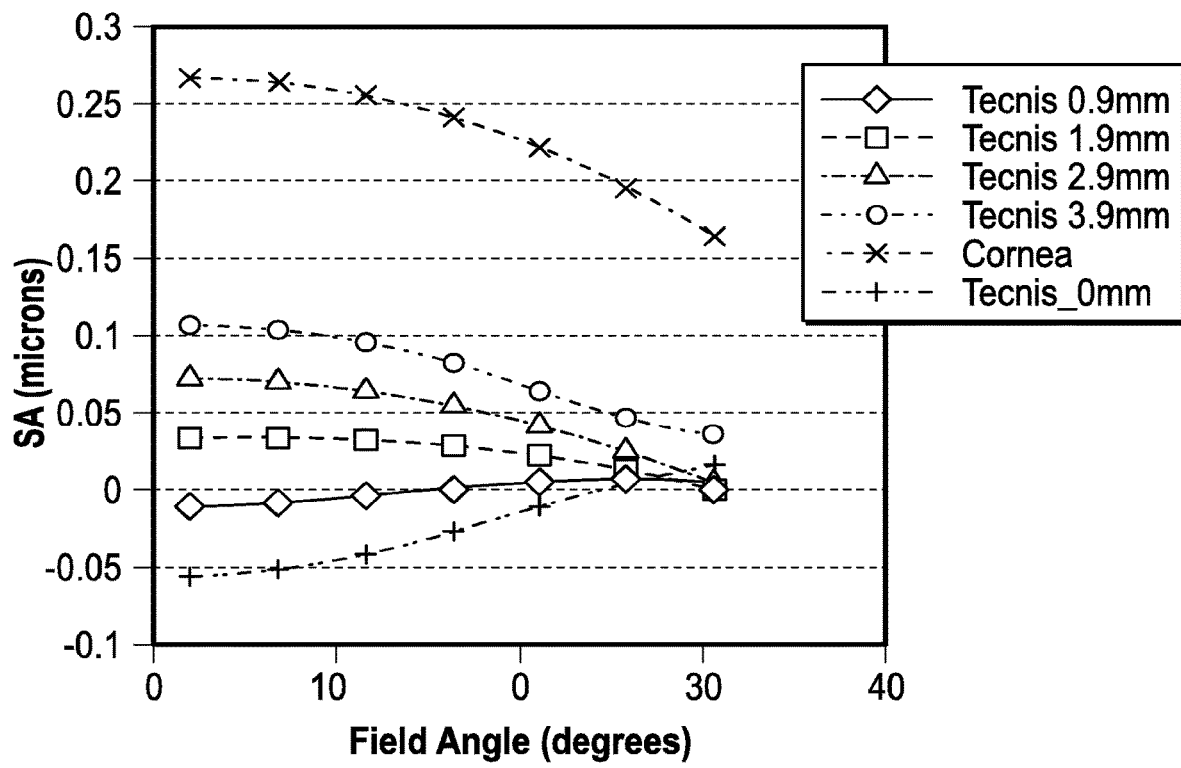
Figure 15D:
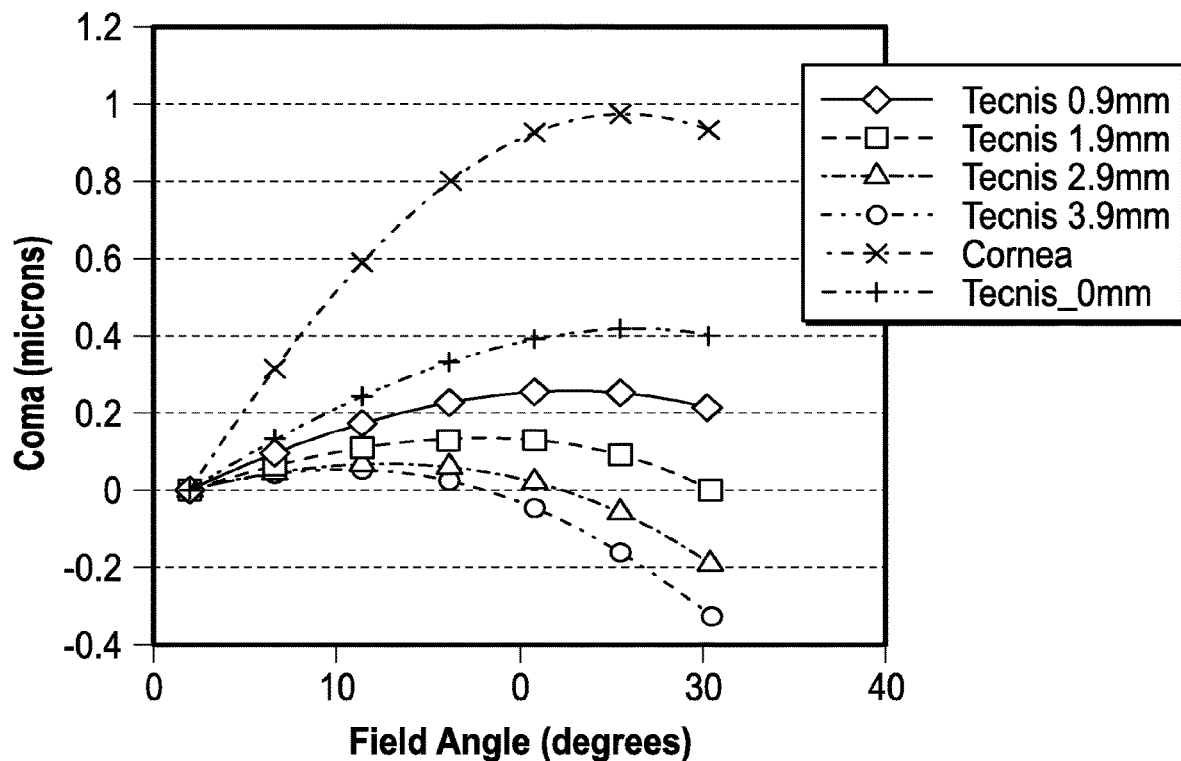

As evidenced by FIGS. 12 and 13, the shape factor affects the optimal displacement which reduces or eliminates one or more peripheral aberrations. To investigate the effect the shape factor has on optimal displacement, FIG. 14 shows a graph 1400 of the influence of shape factor on astigmatism and an optimal position of an IOL. The optimal displacement of the IOL can be defined, in the graph 1400, as the displacement which maximizes astigmatism correction (or minimizes astigmatism induction) for a given shape factor. In some embodiments, the optimal displacement can be defined as the displacement which most reduces the induction of coma, spherical aberration, field curvature, distortion, chromatic aberration, or any combination of these. There are constraints on the amount of improvement or optimization based on constraints of the system, such as a maximal displacement due to the geometry of the eye. For example, an IOL can have a maximum displacement of about 5 mm in a typical eye, as described herein. With that constraint imposed, there is a limit on the amount of astigmatism correction that can be achieved. However, making the shape factor more negative reduces the need for displacement from the iris to maintain astigmatism correction. Accordingly, FIG. 14 illustrates that as the shape factor increases from −4 to zero, the optimal displacement, shown as curve 1415 plotted against axis 1420, increases from 0 mm to 5 mm. When the shape factor becomes greater than −1, the astigmatism, shown as curve 1405 plotted against axis 1410, begins to increase. This indicates that a meniscus lens with a negative shape factor (e.g., a shape factor of less than −1) can provide astigmatism correction while being displaced less than 5 mm from the iris.

Ray tracing simulations were performed using eye models implanted with either lenses representing a typical IOL (e.g., a shape factor of about 0.15) and with a reverse meniscus IOL (e.g., a shape factor of 1.5). Table 6 shows the spherical equivalent (SE), cylinder (CYL), coma, and spherical aberration (SA) calculated for the complete eye model at 20 degrees eccentricity for different IOL displacements with respect to the pupil. The first distance was set to represent a typical IOL position with respect to the pupil (e.g., about 0.9 mm), while an additional 2 mm displacement with respect to the pupil was also considered. For both shape factors, a displacement of 2 mm reduced ocular cylinder (CYL) and coma with respect to the original IOL position.

TABLE 6

| 20 degrees | 0.9 mm (displacement) | 2.9 mm (displacement) |
|---|---|---|
| X = 0.15 | SE = −1D | SE~0 |
|  | CYL = −2D | CYL = −1D |
|  | coma = 0.25 um | coma = 0 um |
|  | SA~0 | SA = 0.07 um |
| X = −1.5 | SE = 0D | SE = 2D |
|  | CYL = −1.2D | CYL = −0.4D |
|  | coma = −0.7 um | coma = −0.66 um |
|  | SA = 0.08 um | SA = 0.02 um |

Simulations were performed on the impact of the physical displacement of a typical IOL when implanted in a model eye. The ocular aberrations for different field angles and IOL positions with respect to the pupil are shown in FIGS. 15A-D. With a displacement of about 2 mm with respect to a typical IOL position (e.g., about 0.9 mm with respect to the pupil), the IOL design with a shape factor of 0.15 provides a similar peripheral cylinder as the typical crystalline lens, but without inducing sphere or coma. This illustrates that, even for a non-meniscus IOL (e.g., an IOL with a shape factor close to 0), physical displacement of the lens from the iris or pupil can be tailored to reduce or eliminate peripheral aberrations relative to the typical placement.

A range of lens characteristics can be varied to improve or optimize the resulting image quality for both on- and off-axis images. For example, to reduce astigmatism and coma, lens displacement, lens shape factor, spherical aberration or asphericity of the lens, index of refraction of the lens, lens thickness, or any combination of these can be configured to improve or optimize peripheral vision. Generally, lens displacement improves astigmatism and coma as it increases (e.g., away from the iris). Similarly, some specific lens shape factors improve astigmatism and coma as it decreases (e.g., a more negative shape factor is better). Likewise, having either a high positive spherical aberration (e.g., to provide an increase in the stop-shift effect) or a high negative spherical aberration (e.g., to compensate corneal spherical aberration) is preferable. For the index of refraction, generally a lower value reduces the need for increased lens displacement. In addition, a gradient index-type lens with several indices of refraction improves peripheral aberrations. Finally, a thicker lens generally gives a better peripheral effect. Implementations of different lens designs that can reduce at least one peripheral optical aberration are discussed in detail below.

In some embodiments, a customized procedure for each patient can be implemented which changes one or more lens characteristics (e.g., peripheral power, peripheral astigmatism), to suit the shape of the patient's retina. Such a procedure is described with greater detail herein with reference to FIG. 42.

Figure 16:
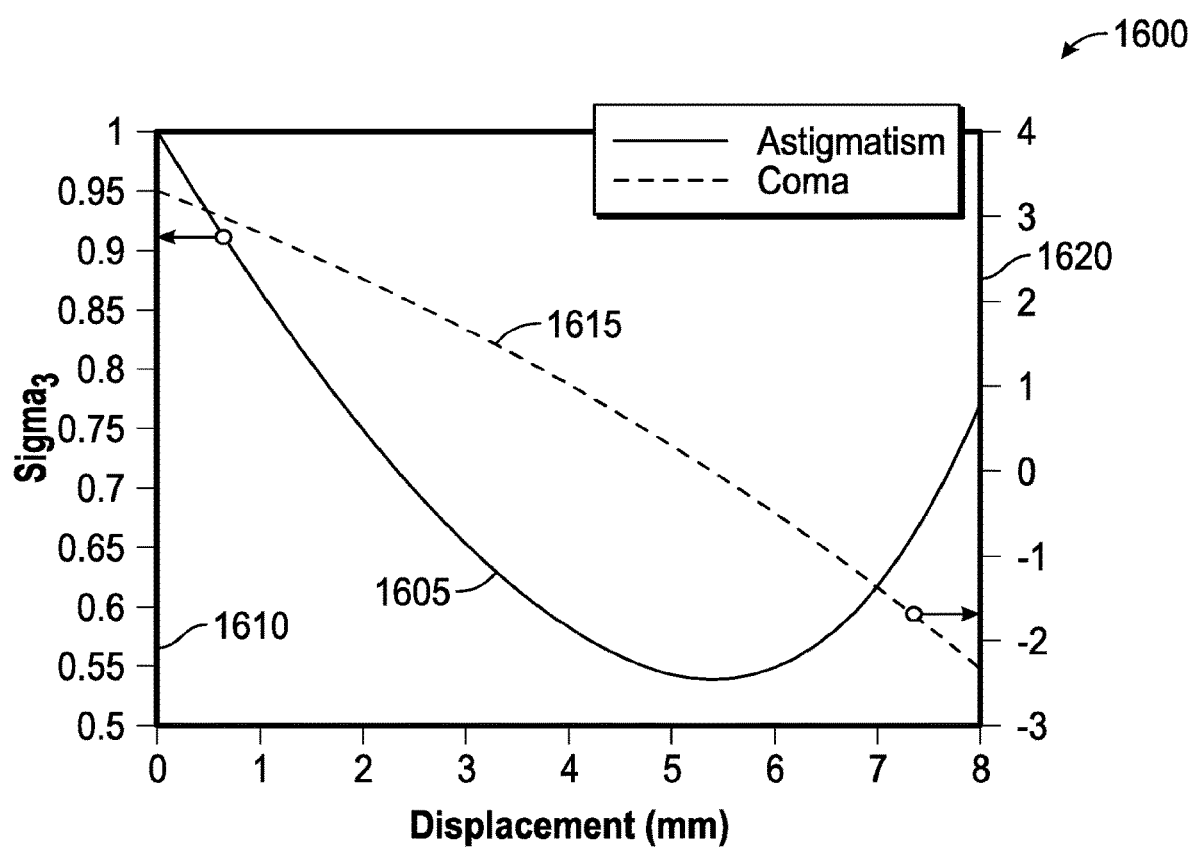
FIG. 16 is a graph illustrating astigmatism and coma as a function of displacement from the cornea of an additional aperture.

In some embodiments, an additional aperture is inserted at the plane of the IOL. The introduction of the additional aperture does not necessarily reduce the astigmatism and coma of the IOL itself. However, it can decrease the astigmatism and coma that arises by oblique incidence on the cornea itself. This effect increases with distance between the cornea and the additional aperture. In certain embodiments, a maximum or optimal effect is achieved when the additional aperture is between about 5 mm and 6 mm from the cornea. This value for optimal displacement depends on the optical power of the cornea. This is illustrated in FIG. 16 which shows a graph 1600 of astigmatism, curve 1605 plotted against axis 1610, and coma, curve 1615 plotted against axis 1620, as a function of displacement of the additional aperture where the IOL has a shape factor of 1.3. As illustrated by the graph 1600, astigmatism is at a minimum and coma is closest to 0 at a displacement of about 5 mm to 6 mm. This demonstrates that it may be beneficial to introduce an additional aperture after the IOL because the pupil position which provides increased performance in reducing astigmatism and/or coma is about 5-6 mm behind the cornea, different from the position of the natural pupil.

The stop-shift equations, placement of additional apertures, and related concepts described herein can be applied to other IOL types, including, for example and without limitation, bi- or multi-focal IOLs, accommodative IOLs, or IOLs with filters.

In some embodiments, an additional aperture can be introduced in the middle of a dual optical system comprising two lenses with the same absolute value of shape factor but with opposite signs (i.e., one positive and one negative, or both 0). For such a configuration, coma, distortion, and transversal chromatic aberration are zero based at least in part on the symmetry of the optical system. Accordingly, in certain embodiments elements behind an aperture stop can be configured to be mirror images of those ahead of the stop, where the optical system functions in unit magnification. In some embodiments, the IOL optical system can be designed to be symmetrical when placed in a patient's eye, e.g., being symmetric with the cornea, the shape factor (e.g., about −1.3), and the position with respect to the pupil.

Figure 17:
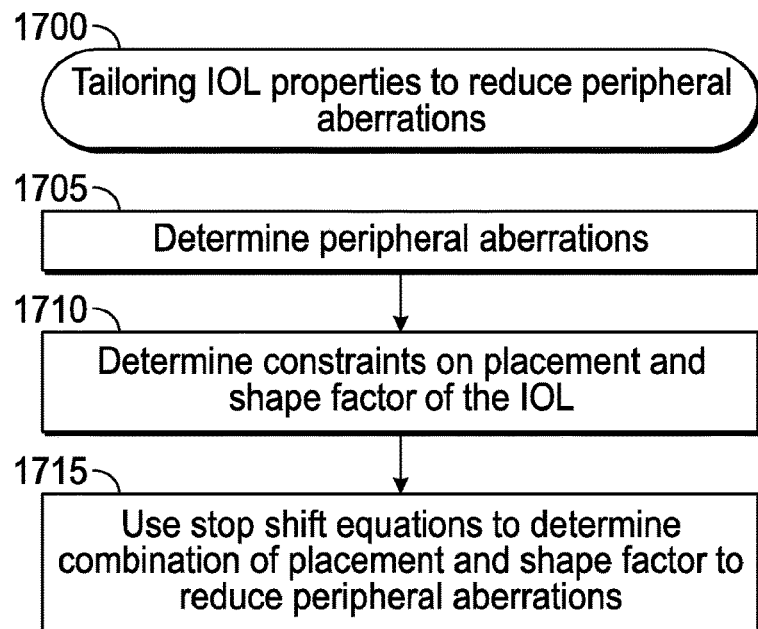
FIG. 17 illustrates a flow chart of an example method for tailoring IOL properties to reduce peripheral aberrations using stop-shift equations.

FIG. 17 illustrates a flow chart of an example method 1700 for tailoring IOL properties to reduce peripheral aberrations using the stop-shift equations. The method 1700 can be performed using a computer configured to execute instructions, as described herein with reference to FIG. 43. A patient's peripheral contrast sensitivity can be improved or optimized when the patient receives an IOL tailored according to the method 1700, where the improvement is relative to a typical IOL (e.g., a shape factor of about 0.15) implanted at a typical distance from the iris (e.g., about 0.9 mm).

In block 1705, a computer model can be used to simulate or determine peripheral aberrations at a retina of a patient with the IOL. The peripheral aberrations can be considered for different eccentricities, field angles, and the like. The peripheral aberrations can be one or more of the aberrations chose from the group consisting of spherical aberrations, coma, astigmatism, defocus, field curvature, distortion, longitudinal chromatic aberration, or lateral chromatic aberration. In some embodiments, a combination of peripheral aberrations can be computed which comprises a weighted sum or weighted average of aberrations. The weighting of the aberrations can be done based at least in part on its contribution to loss of peripheral contrast sensitivity.

Various parameters of the IOL such as the shape factor and/or the placement of the principal plane can be varied to reduce the determined peripheral aberrations. This can be accomplished in several ways. For example, in the illustrated method 1700, various constraints on the placement and shape factor of the IOL are determined as shown in block 1710 and the stop-shift equations described herein are used to determine a combination of placement and shape factor that reduces peripheral aberrations as shown in block 1715.

Another example of determining parameters of the IOL that reduce peripheral aberrations can include starting with an initial shape factor of the IOL and an initial position of the principal plane. Keeping the position of the principal plane fixed, the initial shape factor of the IOL given by the stop-shift equations can be changed to a new shape factor that reduces the peripheral aberrations. Various parameters of the lens such as radius of curvature of the lens, thickness of the lens, refractive indices of the material of the lens can be varied to obtain the final shape factor for the IOL. The principal plane can be shifted to a new position and the shape factor of the IOL can be varied until a new combination of the position of the principal plane and shape factor of the IOL is obtained that further reduces the peripheral aberrations. This process can be repeated iteratively until a combination of position of the principal plane and shape factor of the IOL is obtained that reduces the peripheral aberrations to a threshold or acceptable value or range (e.g., minimizes the peripheral aberrations).

Yet another example of determining parameters of the IOL that reduce peripheral aberrations can include starting with an initial shape factor of the IOL given by the stop-shift equations and an initial position of the principal plane. Keeping the initial shape factor of the IOL fixed, the initial position of the principal plane can be changed to a new position of the principal plane that reduces the peripheral aberrations. The position of the principal plane can be varied in a range around the initial position of the principal plane. The principal plane can be shifted to the new position and the shape factor of the IOL can be varied until a new combination of the position of the principal plane and shape factor of the IOL is obtained that further reduces the peripheral aberrations. This process can be repeated iteratively until a combination of position of the principal plane and shape factor of the IOL is obtained that reduces the peripheral aberrations to a threshold or acceptable value or range (e.g., minimizes the peripheral aberrations).

If image quality improves based at least in part on a reduction of peripheral aberrations, then the modified IOL can be used in place of the previous IOL. This process can be iterated any number of times and/or until an optimal or acceptable IOL is produced. An optimal IOL can be an IOL which minimizes one or more peripheral aberrations (or a weighted combination of aberrations). An acceptable IOL can be an IOL which improves visual acuity based on a determined, selected, or desired threshold of performance, where the threshold of performance can be based at least in part on one or more peripheral aberrations (or a weighted combination of aberrations).

Dual-Optics IOL and Asphericity

In some embodiments, a dual-optics IOL design can be configured to reduce astigmatism and spherical equivalent in a periphery while maintaining good on-axis optical quality. The dual-optics IOL comprises an anterior lens and a posterior lens, where anterior and posterior are relative to the position of the iris. The anterior lens includes an anterior surface and a posterior surface and the posterior lens includes an anterior surface and a posterior surface. In some embodiments, one or more of the surfaces of the anterior and/or posterior lens can be modified to be aspherical, which may also reduce peripheral refraction. Accommodating and non-accommodating implementations of dual-optic IOLs including one or more aspheric surfaces are described below.

In the dual-optics IOL design, the global shape factor of the IOL can be modified to reduce peripheral refraction. Analogous to a single lens where the shape factor is equal to $(R_p+R_a)/(R_p-R_a)$ (described herein above), the global shape factor of a dual-optics IOL can be defined as $(P_p+P_a)/(P_p-P_a)$ where $P_p$ is the power of the posterior lens and $P_a$ is the power of the anterior lens. The shape factor for each individual lens can be modified while keeping the total optical power constant. The shape factor for each lens can be modified by adjusting the anterior and/or posterior surface of the respective lens.

Figure 18:
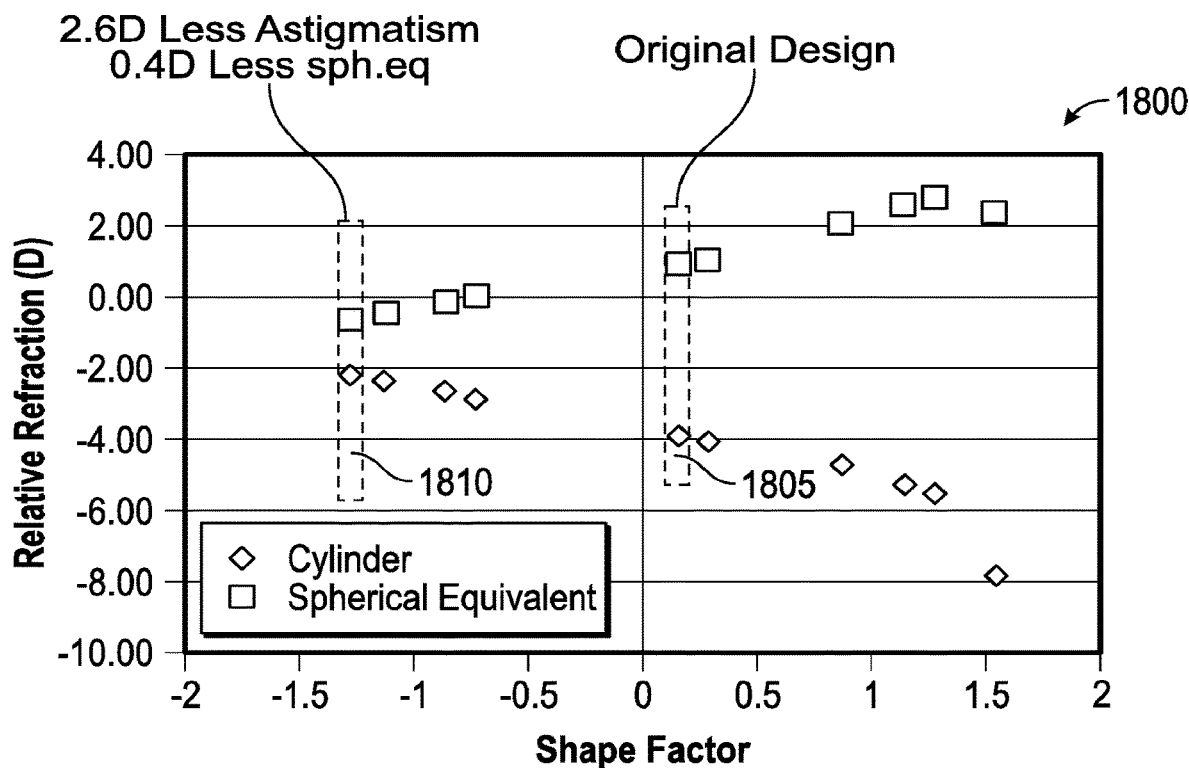
FIG. 18 is a graph illustrating relative refraction at 30 degrees eccentricity as a function of shape factor for a dual optic configuration.

Computer simulations utilizing eye models and ray tracing, as described herein, can be used to determine the effects of the shape factor on both astigmatism and spherical equivalent in periphery. With reference to FIG. 18, graph 1800 illustrates relative refraction at 30 degrees eccentricity as a function of shape factor. The box 1805 labeled "original design" includes a single lens design with a typical shape factor. The box 1810 on the left is for an IOL with a modified shape factor of −1.268 and with the same optical power as the "original design" which results in a reduction of astigmatism of 2.6 D and spherical equivalent of 0.4 D. The astigmatism and spherical equivalent calculations are based on a maximum of a modulation transfer function utilizing a focusing frequency of 50 c/mm. Each point on the graph 1800 is for an IOL with the same optical power as the "original design." This illustrates that modifying the shape factor while maintaining the same optical power provides an improvement in peripheral refraction.

Figure 19:
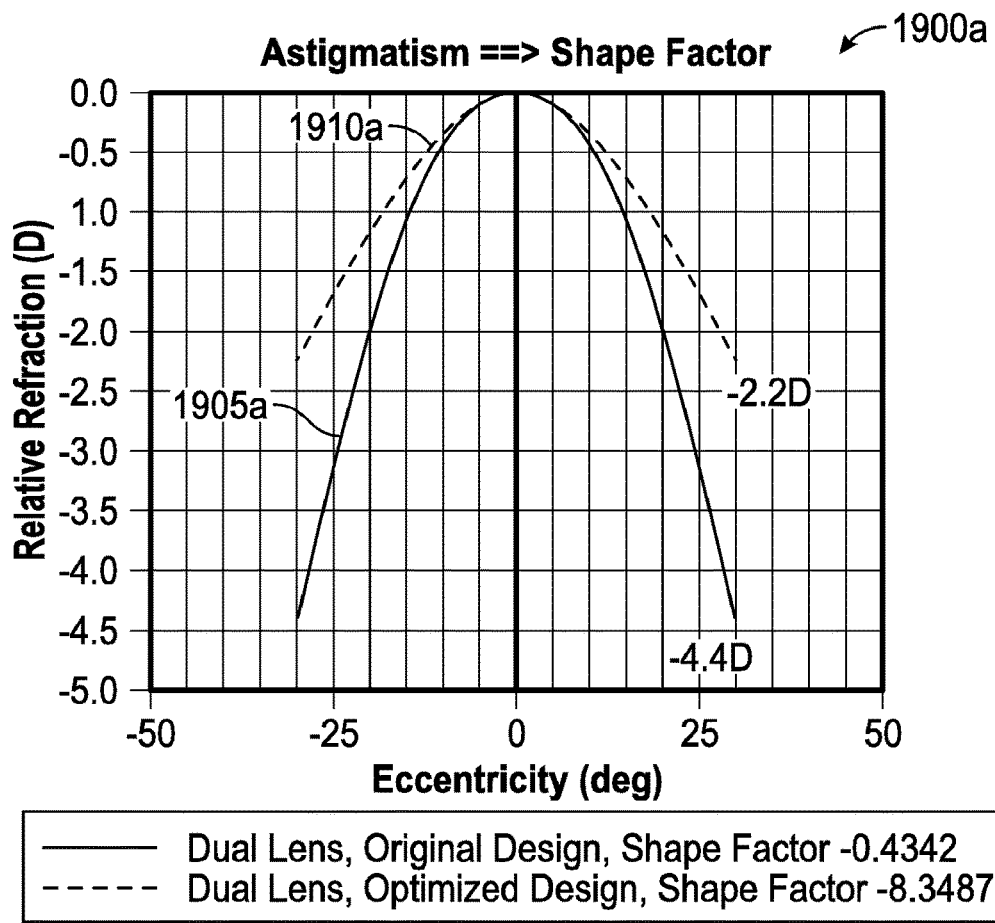
FIG. 19 is a graph illustrating relative refraction as a function of eccentricity for a dual optic configuration.
Figure 19:
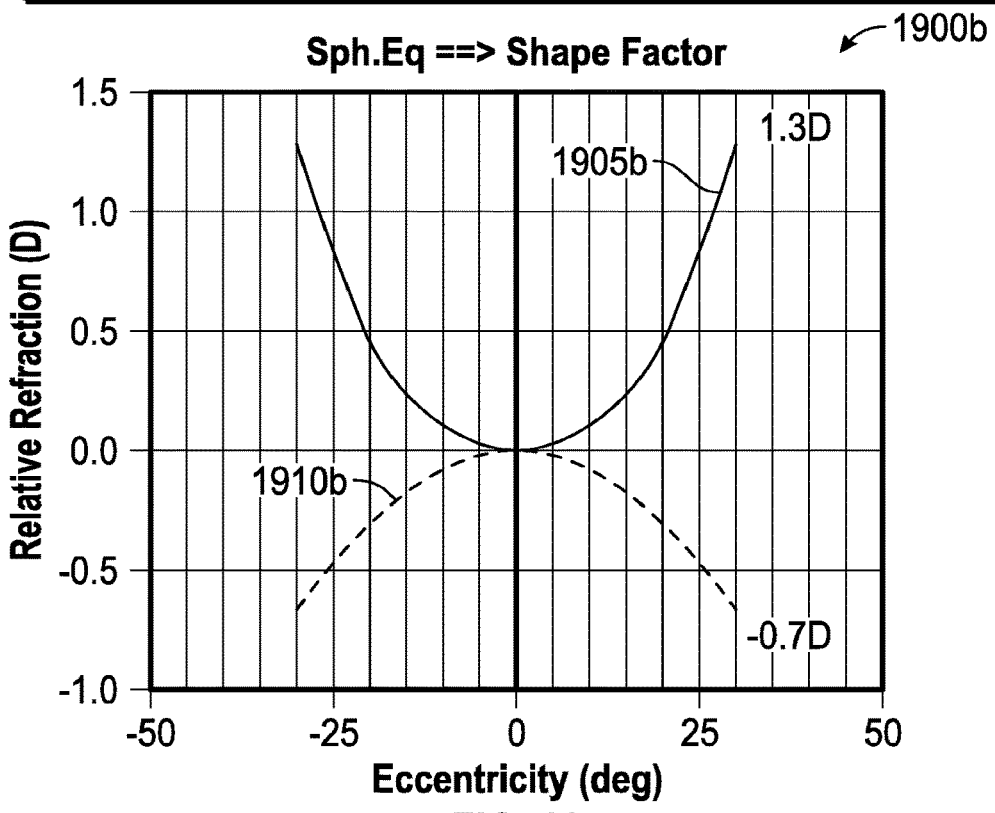

For a dual-optics IOL design, the results are similar to those for the single lens design in graph 1800. For example, FIG. 19 shows graphs 1900a and 1900b of the relative refraction as a function of eccentricity for a dual-optics design. Graph 1900a illustrates the effect on astigmatism for two shape factors, the first shape factor is −0.4342 represented by curve 1905a, and the second shape factor is −8.3487 represented by curve 1910a. As the eccentricity moves away from 0 degrees, the dual lens design with the second shape factor demonstrates an improved astigmatism because the absolute value of the relative refraction is less than that of the IOL with the first shape factor. Similar behavior is observed for spherical equivalent where the first shape factor represented by curve 1905b has a spherical equivalent that is further from 0 when compared to the IOL with the second shape factor represented by curve 1910b as the eccentricity moves away from 0 degrees. As seen in the graphs 1900a and 1900b, the modified shape factor for the dual lens design reduces astigmatism by 2.2 D and spherical equivalent by 0.6 D at 30 degrees eccentricity (e.g., when taking the difference of the absolute values of the relative refraction values). As with the single lens, the total optical power of the dual lens designs is configured to remain the same with the modification of the shape factor. Maintaining the total optical power to be substantially same for one or more configurations of the dual lens design provides good on-axis visual quality.

Figure 20A:
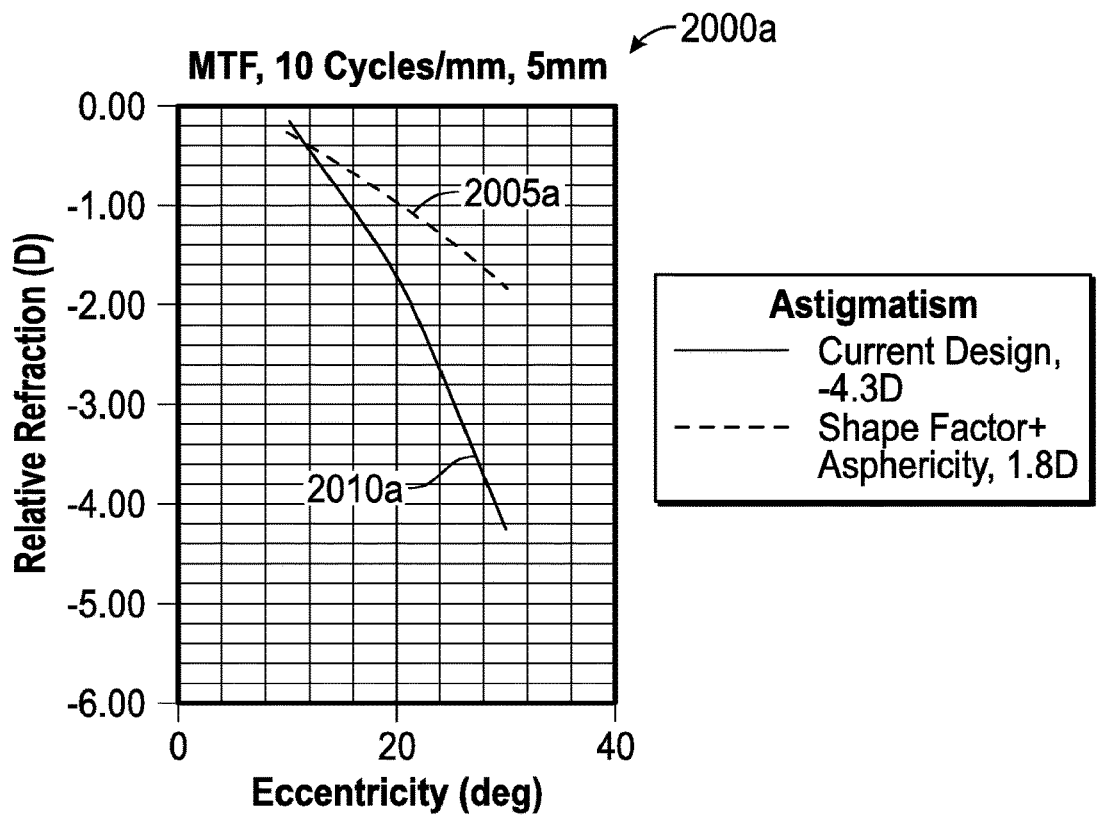
FIG. 20A-B are graphs illustrating the impact of a global shape factor and asphericity on relative refraction for astigmatism and spherical equivalent.
Figure 20B:
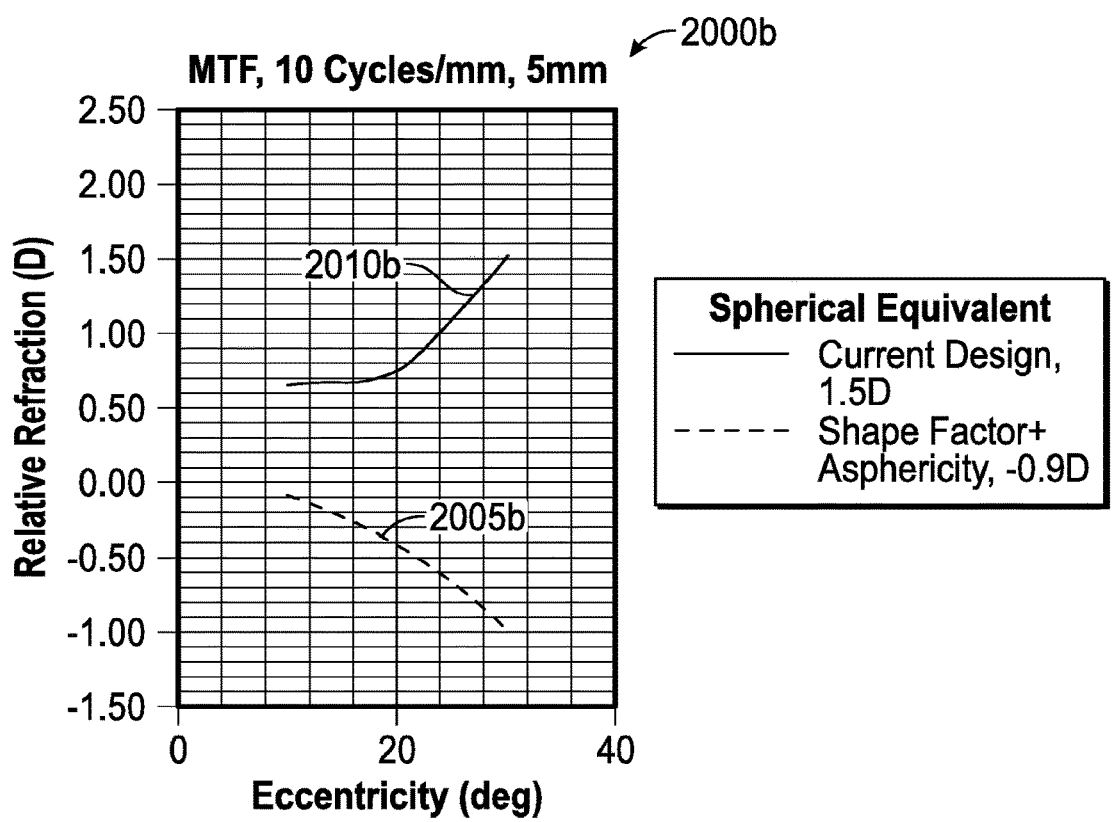

In addition to modifying the shape factor to reduce or minimize peripheral aberrations, either surface of each of the anterior and/or posterior lens can be aspherical with asphericity terms tailored to improve the contrast off-axis. FIGS. 20A-B demonstrate comparative results when asphericity terms are assigned to the anterior surface of each lens (anterior and posterior lenses, each with similar asphericity in this example). FIG. 20A contains a graph 2000a of astigmatism and FIG. 20B contains a graph 2000b of spherical equivalent, both of which demonstrate the effect of shape factor and asphericity on relative refraction. The astigmatism is reduced by 2.5 D and the spherical equivalent is reduced by 0.6 D at 30 degrees eccentricity compared to the original design. The respective lines 2010a and 2010b represent the "original design," having a shape factor of −0.4342 and no asphericity. The respective lines 2005a and 2005b represent a modified design with a modified shape factor of −8.3487 and asphericity where the aspheric surfaces of each individual lens is given by the equation:

$$Z(r) = \frac{\frac{r^2}{R}}{1+\sqrt{1-\frac{r^2(cc+1)}{R^2}}} + AD \cdot r^4 + AE \cdot r^6$$

where R is the anterior radius of curvature, Z is the direction of the optical axis, r is perpendicular to the Z-axis, cc is the conical constant, and AD and AE are coefficients for higher order terms. For the modified design, cc is −1.0228, AD is −7.26e-4, and AE is −9.26e-6.

Figure 21A:
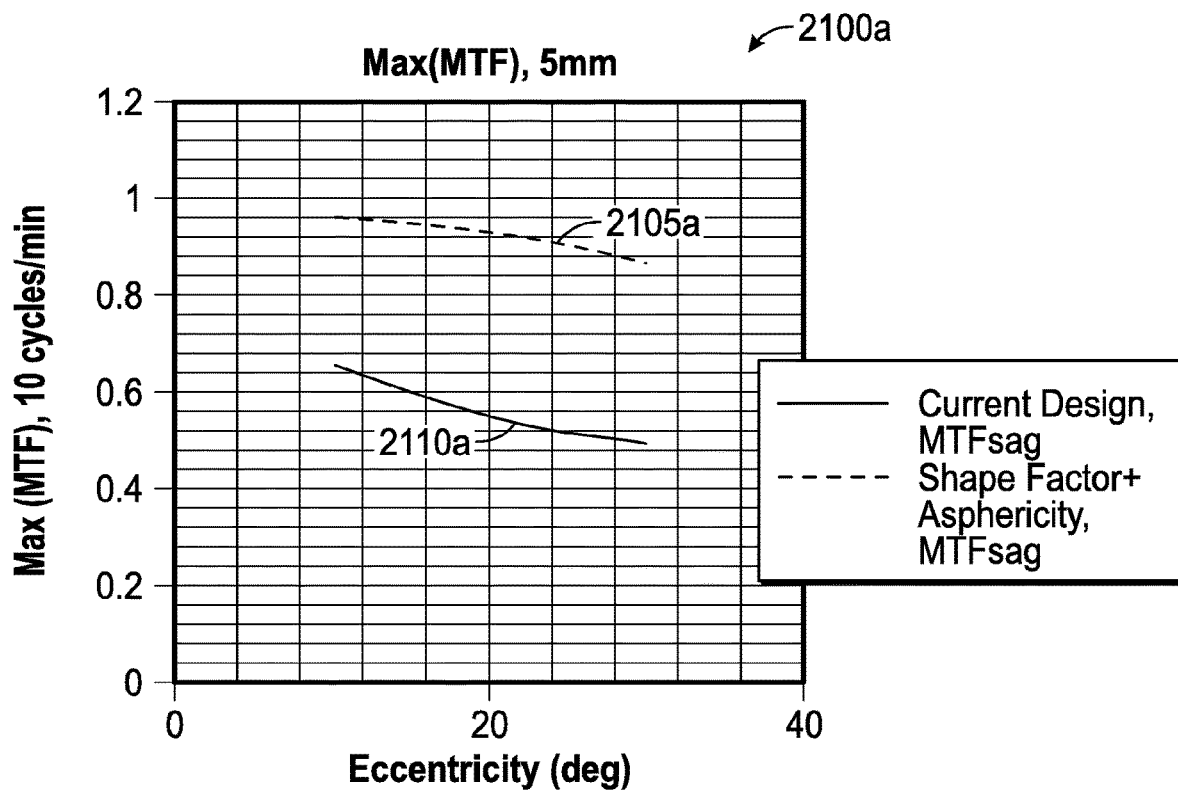
FIG. 21A-B are graphs illustrating the impact of a global shape factor and asphericity on contrast as a function of eccentricity for tangential and sagittal directions.
Figure 21B:
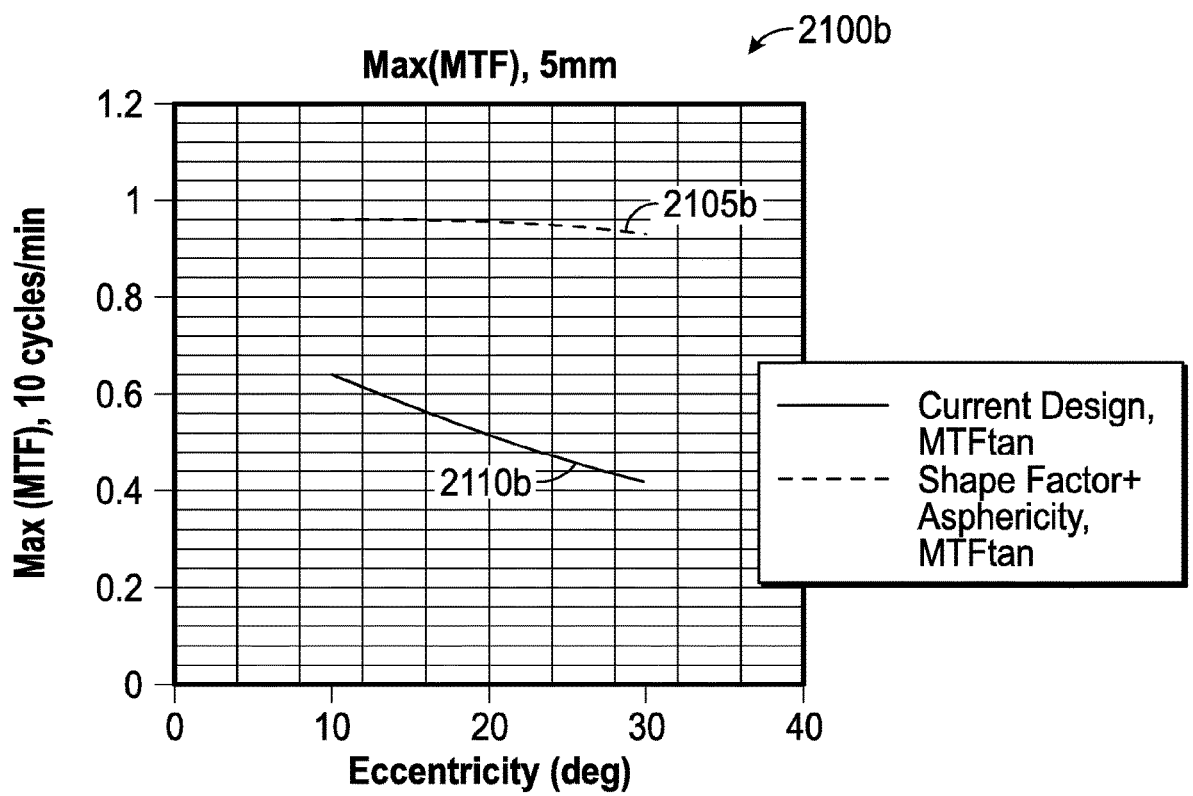

Similarly, FIGS. 21A-B demonstrate the impact of shape factor and asphericity on contrast, where contrast is expressed as the maximum of a modulation transfer function. Whereas the modulation transfer function is similar for on-axis values, the maximal off-axis values are higher in both tangential (graph 2100a) and sagittal (graph 2100b) directions when the shape factor is tailored to improve contrast and the asphericity terms are added on both lenses of the dual-optics IOL, as described herein. The respective lines 2110a and 2110b represent the "original design," having a shape factor of −0.4342 and no asphericity. The respective lines 2105a and 2105b represent a modified design with a modified shape factor of −8.3487 and asphericity where the aspheric surfaces of each individual lens is given by the equation and coefficients above. For the graphs in FIGS. 2000A-B and 2100A-B, the focusing frequency used in the modulation transfer function calculations is 10 c/mm using a 5 mm aperture.

Figure 22:
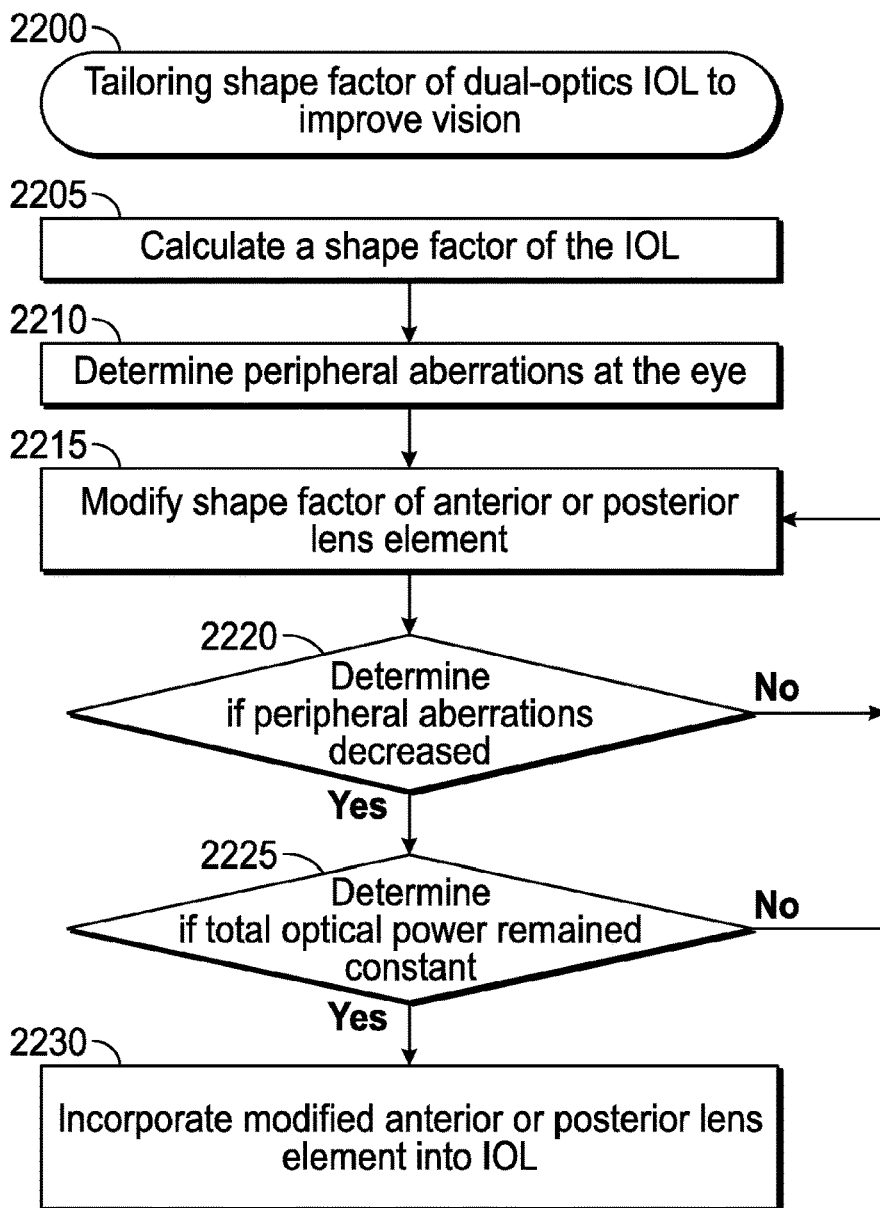
FIG. 22 illustrates a flow chart of an example method for tailoring a global shape factor of a dual-optics IOL to reduce peripheral aberrations.

FIG. 22 illustrates a flow chart of an example method 2200 for tailoring a shape factor of a dual-optics IOL to reduce peripheral aberrations. The method 2200 can be performed using a computer configured to execute instructions, as described herein with reference to FIG. 43. A patient's peripheral contrast sensitivity can be improved or optimized when the patient receives a dual-optics IOL with a shape factor tailored according to the method 2200, where the improvement is relative to a typical IOL or a dual-optic IOL with a typical shape factor.

The step 2205 includes calculating a shape factor of the IOL. The shape factor of the IOL depends on the optical power of the anterior and posterior lenses in the dual-optic IOL, as described herein.

In step 2210, a computer model can be used to simulate or determine peripheral aberrations at a retina of a patient with the dual-optic IOL of step 2205. The peripheral aberrations can be considered for different eccentricities, field angles, and the like. The peripheral aberrations can be one or more of the aberrations chose from the group consisting of spherical aberrations, coma, astigmatism, field curvature, distortion, longitudinal chromatic aberration, or lateral chromatic aberration. In some embodiments, a combination of peripheral aberrations can be computed which comprises a weighted sum or weighted average of aberrations. The weighting of the aberrations can be done based at least in part on its contribution to loss of visual acuity.

In step 2215, the shape factor of the dual-optics IOL are modified to change the peripheral aberrations. As tested in step 2225, the total optical power of the dual-optic IOL can be configured to remain constant when changes are made to the shape factor.

In step 2220, the performance of the modified dual-optic IOL (as modified in step 2215), is compared to the dual-optic IOL of the previous iteration. If image quality improves based at least in part on a reduction of peripheral aberrations, then the modified IOL can be used in place of the previous IOL. This process can be iterated any number of times and/or until an optimal or acceptable IOL is produced. An optimal IOL can be an IOL which minimizes one or more peripheral aberrations (or a weighted combination of aberrations). An acceptable IOL can be an IOL which improves peripheral contrast sensitivity based on a determined, selected, or desired threshold of performance, where the threshold of performance can be based at least in part on one or more peripheral aberrations (or a weighted combination of aberrations).

In step 2225, the total optical power of the dual-optic IOL is computed. If the total optical power changes, the method 2200 returns to step 2215 to modify the shape factor to maintain a constant total optical power.

In step 2230, when an acceptable or optimized dual-optic IOL has been determined, the dual-optic IOL can be implanted into a patient's eye to improve the patient's vision by reducing peripheral aberrations relative to a typical IOL.

In some embodiments, the method 2200 can be implemented for an IOL with more than two lenses. In some embodiments, the method 2200 can include an additional step of modifying the asphericity of one or more surfaces of the anterior and/or posterior lenses. With such modifications, a similar procedure is followed where the effects on the peripheral aberrations are verified to improve peripheral refraction effects and the total optical power is verified to remain constant.

Binocular Summation to Improve Peripheral Vision

Image quality produced by artificial IOLs can be optimized by varying different design parameters such as index of refraction of the material of the IOL, radii of curvature, asphericity, etc. In various implementations of artificial IOLs it may not be practical to simultaneously optimize the acuity for central vision as well contrast sensitivity for peripheral vision due to the limited available degrees of freedom. Accordingly, in such implementations, optimizing the acuity for central vision could degrade the acuity for peripheral vision. Furthermore, due to limited available degrees of freedom, it may not be practical to remove all peripheral astigmatism, coma and peripheral defocus even when performing optimization procedures solely for peripheral vision. The methods and systems described herein can use binocular summation to overcome visual losses caused by peripheral aberrations.

Figure 23:
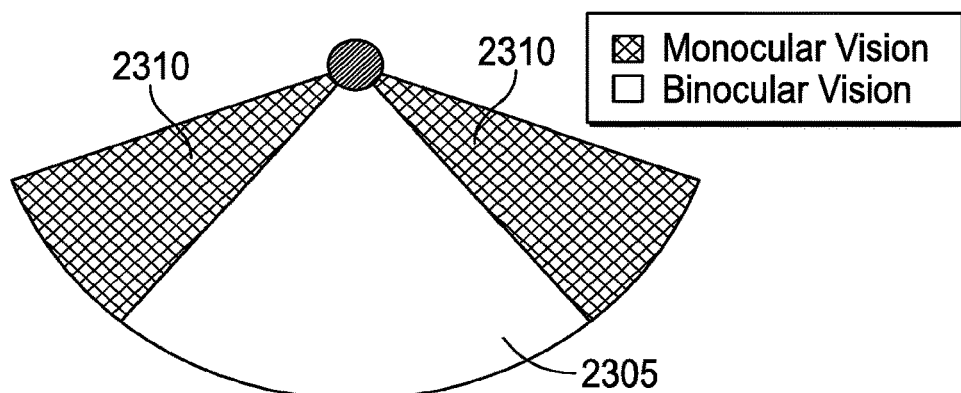
FIG. 23 shows the substantial part of the peripheral field of view that is visible to both eyes for an implementation of an IOL implanted in the eye.

Without subscribing to any particular theory, humans have a forward facing horizontal field of view of approximately 190 degrees with two eyes, approximately 120 degrees of which makes up the binocular field of view (i.e., seen by both eyes). FIG. 23 represents the forward facing horizontal field of view. The forward facing horizontal field of view includes a central region 2305 that represents the binocular field of view and edge regions 2310 that represents the monocular field of view (i.e., seen by one eye). In general the binocular field of view includes the peripheral field of view used for most daily tasks. Thus optimizing visual acuity in the binocular field of view can increase the contrast sensitivity for peripheral vision as well.

One approach to increase contrast sensitivity in the binocular field of view is to implant a first IOL in one eye that is adapted to view tangential targets (targets in the tangential plane) better than the sagittal targets and a second IOL in another eye that is adapted to view sagittal targets (targets in the sagittal plane) better than the tangential targets. For example, in the horizontal visual field, the left eye could be implanted with an IOL that is better at seeing vertical lines whereas the right eye could be implanted with an IOL that is better at seeing horizontal lines. The brain combines the information received from the first and the second eyes through binocular summation such that the combined vision has more contrast sensitivity than the vision provided by one eye alone.

In various embodiments, visual acuity in the binocular field of view can be increased by implanting an IOL that is optimized to provide increased contrast sensitivity in the sagittal plane in a first eye and by implanting an IOL that is optimized to provide increased contrast sensitivity in the tangential plane in a second eye. In various embodiments, the increased contrast sensitivity in the sagittal plane can come at the expense of decreased visual acuity in the tangential plane and vice versa. The various embodiments, the IOL configured to provide increased visual acuity in the sagittal and tangential planes can include a single ring microstructure as discussed above. In various embodiments, the IOL configured to provide increased contrast sensitivity in the sagittal and tangential planes can also provide increased visual acuity at near or far distances. Without any loss of generality, the tangential plane is the plane that contains the principal ray and the optical axis of the IOL and the sagittal plane is the plane that contains only the principal ray and is oriented perpendicular to the tangential plane.

One approach to optimize the visual image in the sagittal/tangential planes is to implant an IOL at a first distance from the pupil in a first eye and implant an IOL at a second distance from the pupil in a second eye. The first and second distance can be different. For example, in various embodiments, a difference between the first and second distance can be approximately 0.5 mm to approximately 10 mm.

Figure 24A:
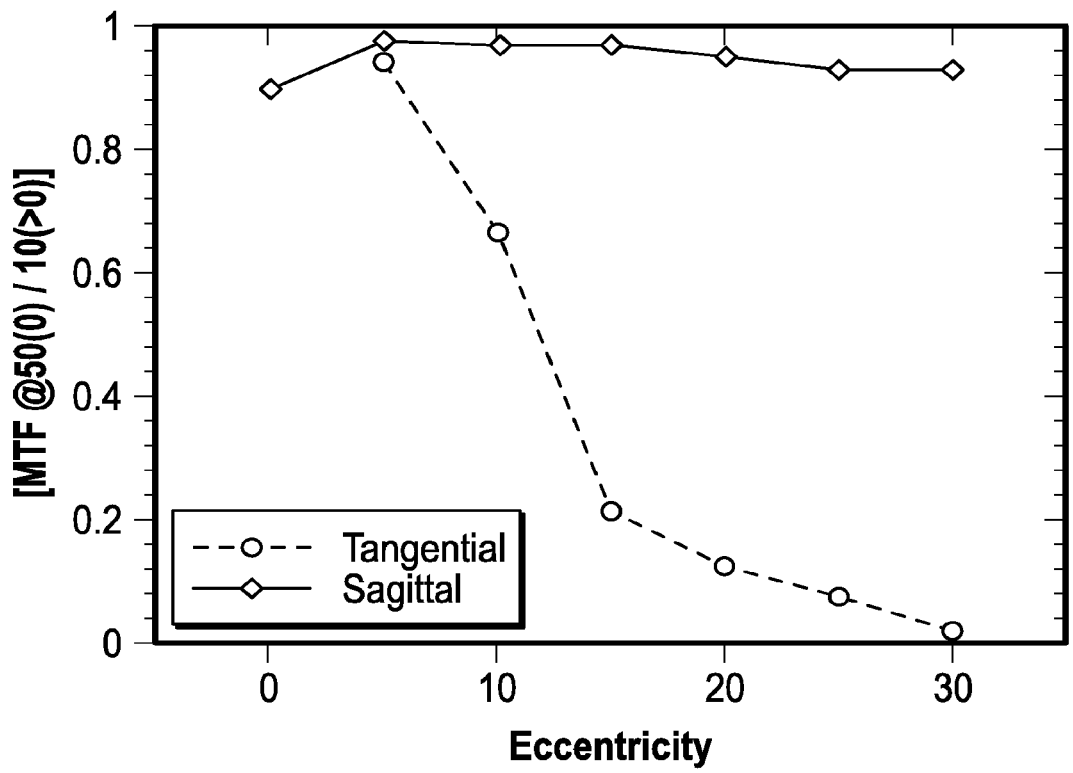
FIG. 24A is a graph illustrating the modulation transfer function (or MTF) as a function of eccentricity for sagittal and tangential vision for an implementation of an IOL at a first axial focus position.
Figure 24B:
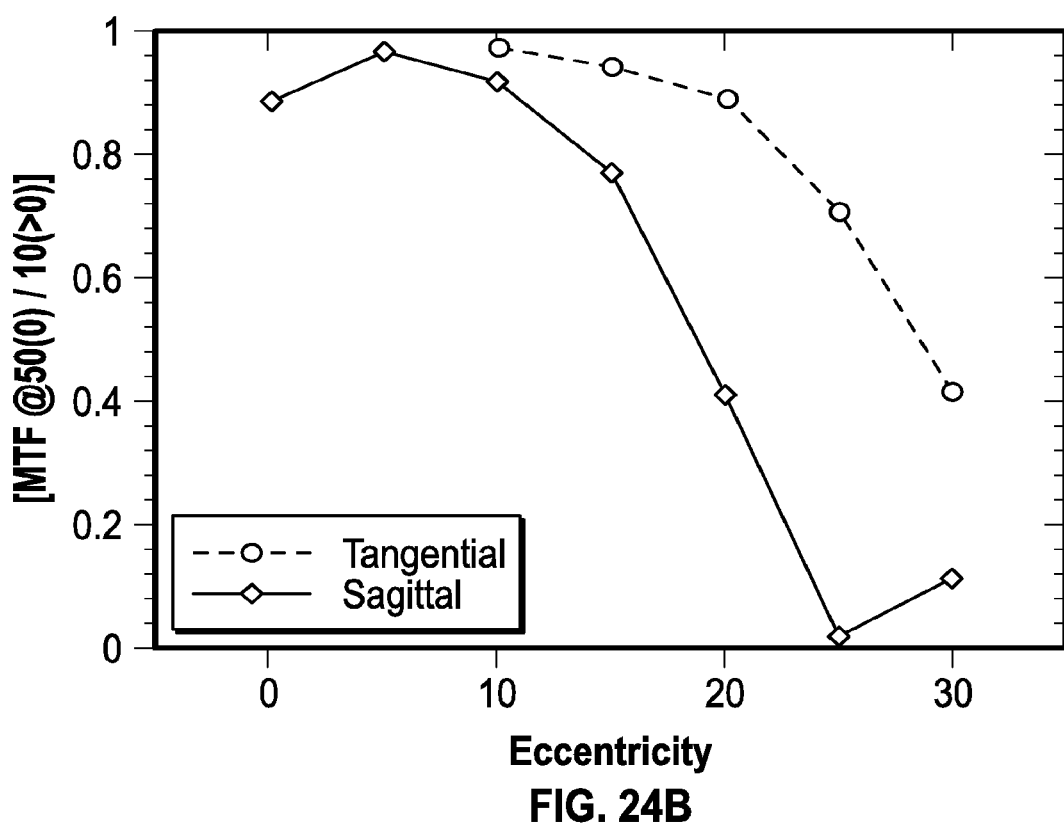
FIG. 24B is a graph illustrating MTF as a function of eccentricity for sagittal and tangential vision for an implementation of the IOL at a second axial focus position.

FIG. 24A is a graph illustrating MTF as a function of eccentricity for sagittal and tangential vision for an implementation of an IOL implanted at a first distance from the pupil in a first eye such that incident light is focused at a first axial focus position. FIG. 24B is a graph illustrating MTF as a function of eccentricity for sagittal and tangential vision for an implementation of the IOL implanted at a second distance from the pupil in a second eye such that incident light is focused at a second axial focus position. The second distance is about 2 mm further from the pupil as compared to the first distance. As noted from FIG. 24A, for the IOL implanted at the first distance, the sagittal vision (represented by solid line) has almost uniform visual acuity at different values of eccentricity from about 0 to about 30 degrees. However, the visual acuity for tangential vision (represented by dashed line) decreases sharply as the eccentricity increases from about 0 to about 30 degrees for the IOL implanted at the first distance.

It is noted from FIG. 24B that optical quality for tangential vision (represented by dashed line) for the IOL implanted at the second distance is better than the optical quality for tangential vision (represented by dashed line) for the IOL implanted at the first distance for higher values of eccentricity. It is further noted from FIG. 24B that optical quality for sagittal vision (represented by solid line) for the IOL implanted at the second distance is lower than the optical quality for sagittal vision (represented by solid line) for the IOL implanted at the first distance for higher values of eccentricity. Accordingly, due to binocular summation, the combined image produced by the two IOLs implanted at different distances will give better vision for both tangential and sagittal vision as compared to two IOLs implanted at the same distance.

In various embodiments, other parameters of the IOLs such as coma, radius of curvature, focal length, etc. can be optimized separately monocularly such that visual acuity in the periphery for the image produced by combining information from each eye by employing binocular summation can be increased. A binocular visual simulator can be used to optimized different parameters of the IOLs such as coma, radius of curvature, focal length, implant distance, etc. for each eye of a patient to obtain increased visual acuity in the entire binocular field of view that includes the central visual zone and the peripheral visual zone. In some embodiments, the stop-shift equations and associated methods described herein can be used to improve or optimize the individual IOLs in the binocular system, where each side is improved or optimized to achieve an appropriate performance standard (e.g., by reducing peripheral aberrations along an appropriate direction).

IOL that Provides Astigmatic Correction to Improve Peripheral Vision

Figure 25:
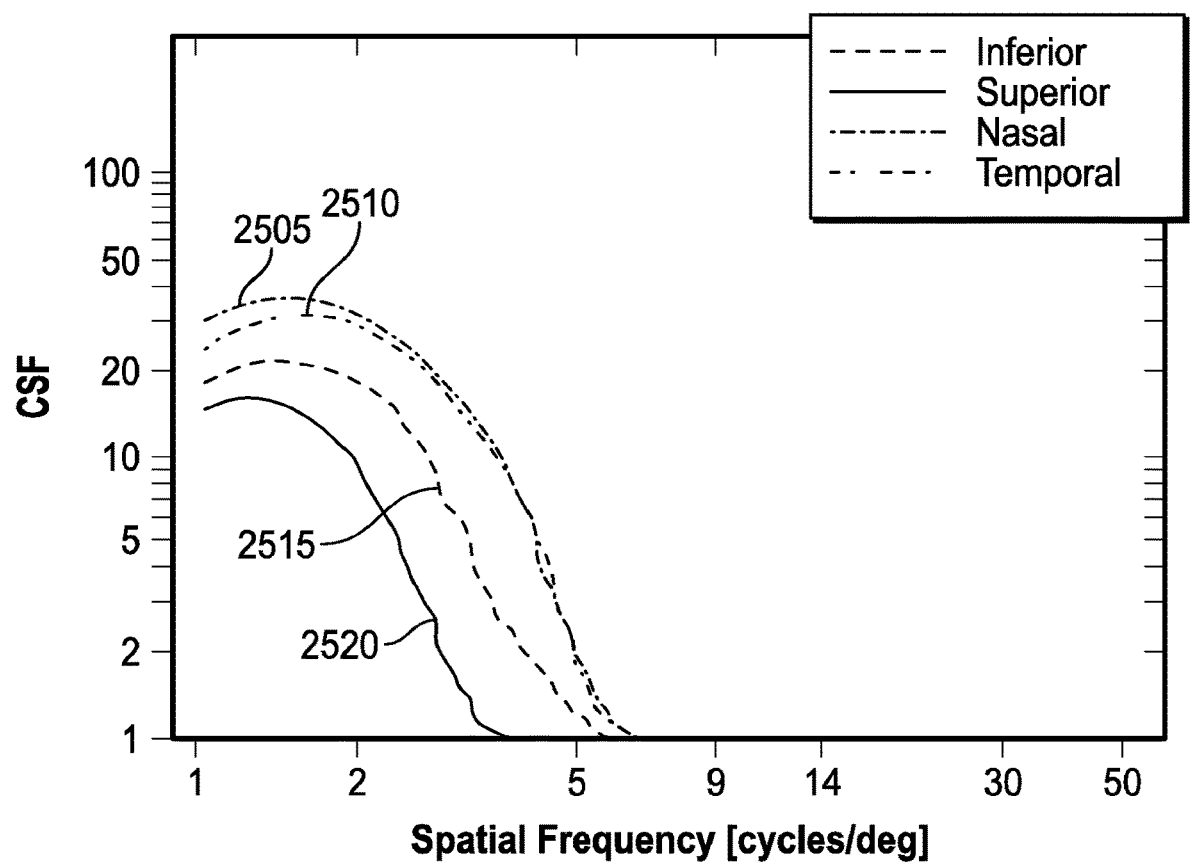
FIG. 25 is a graph illustrating contrast sensitivity function in four different field directions.

The field of view can be vertically divided into a first vertical hemi-field that is oriented nasally (referred to as nasal field of view) and a second vertical hemi-field oriented temporally (referred to as temporal field of view). The field of view can be horizontally divided into an upper horizontal hemi-field oriented upwards towards the brow (referred to as superior field of view) and a lower horizontal hemi-field oriented downwards towards the cheek (referred to as inferior field of view). The nasal and temporal fields of view correspond to a view along the horizontal direction while the superior and inferior fields of view correspond to a view along the vertical direction. FIG. 25 is a graph illustrating contrast sensitivity function (CSF) in the nasal, temporal, superior and inferior fields of view. The CSF values plotted in the graph are corrected for optical errors using an adaptive optics system. Thus, the CSF values depend only on the neural limits. Curve 2505 depicts the CSF 20 degrees in the periphery of the nasal field of view. Curve 2505 depicts the CSF 20 degrees in the periphery of the temporal field of view. Curve 2515 depicts the CSF 20 degrees in the periphery of the inferior field of view. Curve 2520 depicts the CSF 20 degrees in the periphery of the superior field of view. It is noted from FIG. 25 that the CSF values 20 degrees in the periphery of the nasal and temporal fields of view are larger than the CSF values 20 degrees in the periphery of the inferior and superior fields of view. This indicates that the vision is less limited by neural factors along the horizontal direction corresponding to the nasal and temporal fields of view than along the vertical direction corresponding to inferior and superior fields of view. Thus, providing optical correction along the horizontal direction may be more advantageous than providing optical correction along the vertical direction.

In various embodiments, optical correction along the horizontal direction can be provided by implanting an IOL with a toric component. In various embodiments, the toric component can be included even when the patient has good central vision and does not need an astigmatic or toric correction and. The IOL with the toric component has a higher optical power along the vertical axis corresponding to an axis of 90-degrees using the common negative cylinder sign convention than the horizontal axis corresponding to an axis of 180-degrees using the common negative cylinder sign convention. Such a lens can improve image quality in the horizontal field of view. This can be beneficial to patients, as most relevant visual tasks are carried out in the horizontal field of view.

Additionally, the IOL can be configured to provide an astigmatic correction along the vertical and/or the horizontal axis. An astigmatic correction when combined with the correct higher order aberrations can provide a good on-axis depth of focus, which can advantageously reduce the need for glasses to improve near distance vision. For example, as discussed above, vision is less limited by neural factors in the horizontal direction, thus providing optical correction along the horizontal direction is beneficial as compared to providing optical correction along the vertical direction.

Moreover, for most daily activities peripheral vision along the horizontal direction is more common and relevant than peripheral vision along the vertical direction. For example, when driving the objects in the peripheral vision along the vertical direction includes portions of the sky and the interior of the car which are relatively less important to monitor as compared to objects in the peripheral vision along the horizontal direction which include portions of the street, street lights, incoming traffic, traffic signs, pedestrians, etc. To drive safely, objects in the peripheral vision along the horizontal direction should be monitored, detected, identified and resolved with sufficient acuity. Thus providing optical correction that improves visual acuity for objects in the peripheral vision along the horizontal direction can be beneficial for accomplishing most daily activities.

In various embodiments, the optical correction provided to increase visual acuity along the horizontal direction can include a refractive IOL configured such that a part of an anterior or posterior surface of the IOL is a toric surface and a part of the same anterior or posterior surface of the IOL is a non-toric surface. In various embodiments, the non-toric part of the IOL can be a spherical surface or an aspheric surface. The toric surface can provide astigmatic correction. In various embodiments, the toric surface can have higher optical power along the vertical axis than the horizontal axis.

The view through such an IOL can increase the contrast sensitivity along the horizontal field of view to a larger extent than the contrast sensitivity along the vertical field of view.

In various embodiments, the toric surface of the IOL can be configured to provide a single add power. In some embodiments, the toric surface of the IOL can be configured to provide multiple add powers. In various embodiments, the IOL can include more than one toric surface. In various embodiments, one or more toric surface of the IOL can either be sectorial or concentric.

In various embodiments, the contrast sensitivity of the field of view can be optimized by selecting the add power provided by the toric surface and the position and/or orientation of the toric surface to satisfy the individual needs of the patient. For example, a patient who desires a good image quality indoors could be provided with an IOL that includes the non-toric portions in the center of the IOL and toric portions toward the edges of the IOL. Another patient may desire to have increased visual acuity in the peripheral vision along with increased depth of focus. Such patients can be provided with an IOL that includes toric portions in the center of the IOL.

The optical correction provided to increase contrast sensitivity along the horizontal direction can include corrections for astigmatism (e.g., with the rule and/or against the rule astigmatism) and other spherical and/or non-spherical aberrations (e.g., coma, trefoil, etc.). In various embodiments, the optical correction provided to increase visual acuity along the horizontal direction can also increase on-axis depth of focus. In various embodiments, aberrations can be included in the IOL to provide on-axis depth of focus. The aberrations included to provide on-axis depth of focus can be a combination of spherical aberration and coma or other higher order aberrations. In various embodiments, the IOL can include diffractive features to extend depth of focus. In various embodiments, one eye can be implanted with an IOL having a first amount of astigmatic correction and a first amount of aberrations and the second eye can be implanted with an IOL having a second amount of astigmatic correction and a second amount of aberrations such that increased visual acuity for peripheral vision and increased depth of focus is obtained due to binocular summation.

IOLs that Compensate for Peripheral Refractive Errors

Figure 26:
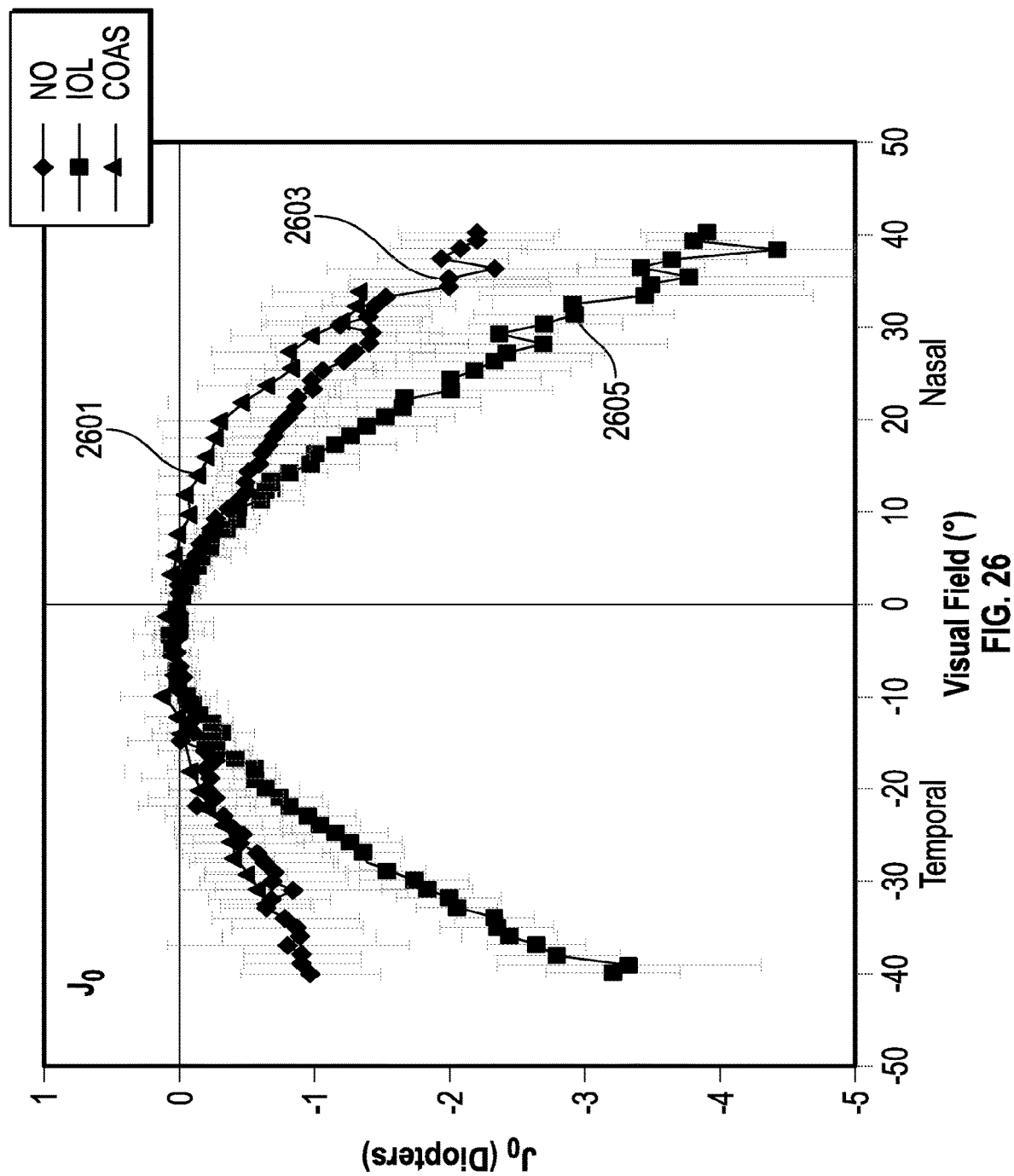
FIG. 26 illustrates a comparison of the optical image quality (horizontal astigmatism) in the periphery of phakic and pseudophakic eyes.

FIG. 26 illustrates a comparison of the cylinder in the periphery of phakic (having a natural lens) eyes (represented by curve 2603) and pseudophakic (implanted with an IOL) eyes (represented by curve 2605). The data represented by curves 2603 and 2605 were obtained using a scanning aberrometer on 12 subjects in the age group between 64 and 80 years in phakic and pseudophakic eyes with a pupil size of 3 mm. Using Curves 2603 and 2605 are reproduced from the article "Comparison of the Optical Image Quality in the Periphery of Phakic and Pseudophakic Eyes," by Bart Jaeken, Sandra Mirabet, Jose Maria Marin and Pablo Artal that was published in the journal Investigative Ophthalmology & Visual Science, Vol. 54, No. 5, pages 3594-3599, May 2013. A scanning aberrometer (e.g., a Hartmann-Shack (HS) wavefront sensor) was used to obtain values for defocus (M), cylindrical power along two axes oriented at 0 degrees and 45 degrees ($J_0$ and $J_{45}$) and higher order aberrations (e.g. spherical aberrations and coma) included in curves 2603 and 2605. FIG. 26 also illustrates data obtained from 14 phakic eyes in the age group less than 30 years old (represented by curve 2601). The data includes values for defocus (M), cylindrical power along two axes oriented at 0 degrees and 45 degrees ($J_0$ and $J_{45}$) with respect to the equator of the IOL and higher order aberrations (e.g. spherical aberrations and coma), obtained using a complete ophthalmic analysis system (COAS). FIG. 26 illustrates the variation of the power along the cylinder axis oriented at 0 degrees with respect to the equator ($J_0$) as a function of the visual field. The visual field is measured in degrees and varies between about ±40 degrees as a patient's gaze shifts from temporal vision to nasal vision along the natural convergence path. The terms visual field angle and eccentricity can be used interchangeably in the context of this application.

Comparison of curves 2601 and 2603 indicates a good agreement between the COAS and the scanning aberrometer systems. Comparison of curves 2601 and 2603 further indicates that the cylinder power is independent of age. It is also observed from FIG. 26 that the cylindrical power component $J_0$ increases in the temporal and nasal peripheral visions in pseudophakic eyes as compared with phakic eyes indicating a possible increase in peripheral refractive errors in patients implanted with IOLs. This increase in peripheral refractive errors can have a measurable impact on visual function and could affect day-to-day tasks such as driving, locomotion, gist recognition etc. Various systems and methods to improve peripheral vision disclosed herein are based on the recognition that certain peripheral aberrations can depend not only on the visual field angle but also on the foveal refractive correction and therefore in the IOL power. Thus, it would be advantageous if embodiments of IOLs take into account the effect of refractive power of the IOL on peripheral vision and optimize the refractive characteristics in the periphery of the IOL accordingly.

Figure 27:
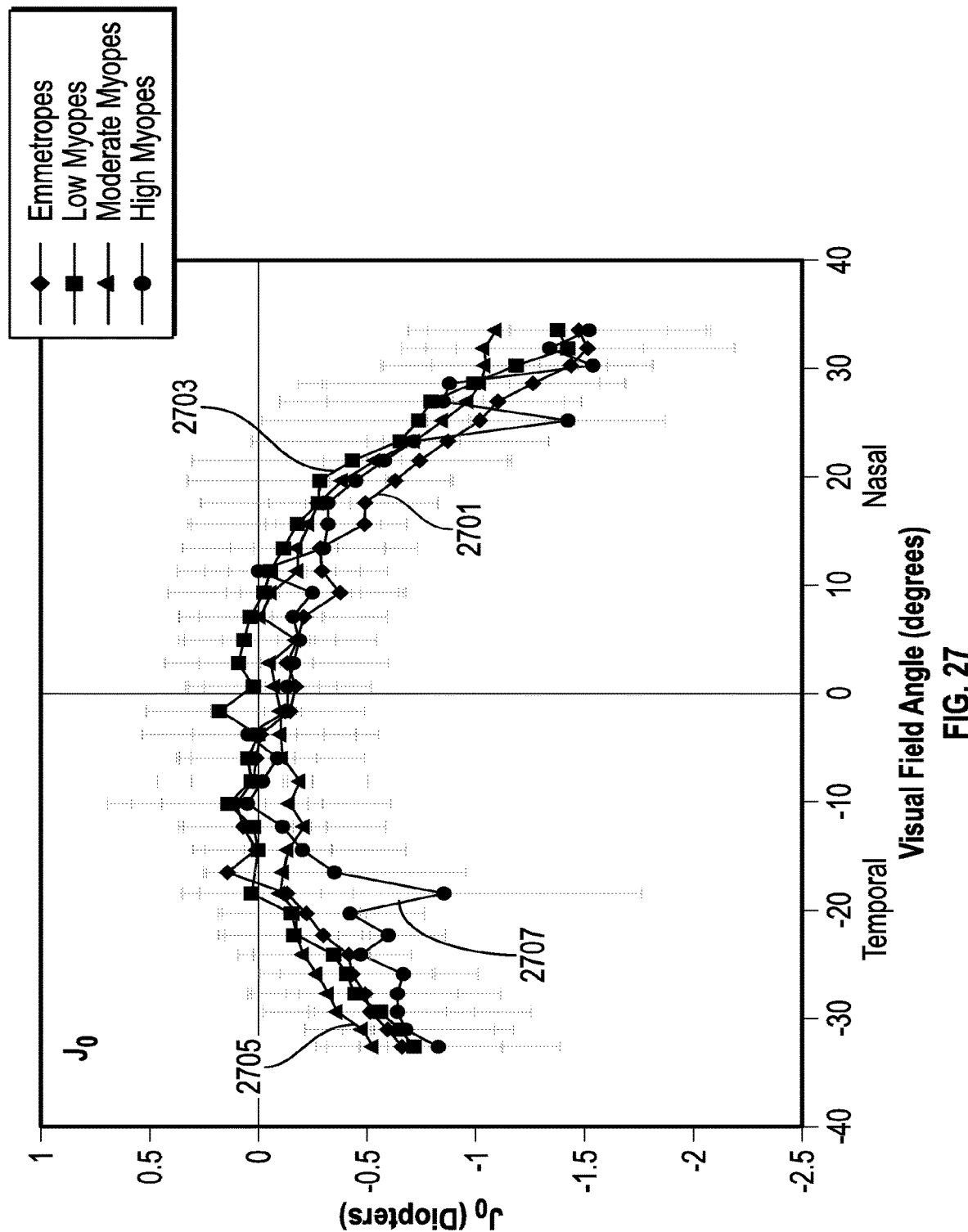
FIG. 27 is a graph illustrating the variation of cylinder power along the axis oriented at 0-degrees with respect to the equator ($J_0$) as a function of visual field for patients with different refractive error on axis.

Recent data indicates that peripheral astigmatism and/or horizontal coma can be patient independent. For example, peripheral astigmatism and/or horizontal coma can be independent of the age of the patient and on its geometrical and optical properties. FIG. 27 is a graph illustrating the variation of cylinder power along the axis oriented at 0-degrees with respect to the equator ($J_0$) as a function of visual field for young subjects with different visual conditions (e.g., emmetropia, low myopia, moderate myopia and high myopia). Curve 2701 illustrates the variation of $J_0$ with visual field angle for an eye in an emmetropic state. Without any loss of generality, an eye in an emmetropic state has a foveal spherical equivalent power between about −0.5 Diopter and about +0.5 Diopter. Curve 2703 illustrates the variation of $J_0$ with visual field angle for patients with low amounts of myopia. Without any loss of generality, patients with low amounts of myopia have a foveal spherical equivalent power between about −0.5 Diopter and about −1.5 Diopter. Curve 2705 illustrates the variation of $J_0$ with visual field angle for patients suffering from moderate amounts of myopia. Without any loss of generality, patients with moderate amounts of myopia have a foveal spherical equivalent power between about −1.5 Diopter and about −2.5 Diopter. Curve 2707 illustrates the variation of $J_0$ with visual field angle for patients suffering from high amounts of myopia. Without any loss of generality, patients with high amounts of myopia have a foveal spherical equivalent power between about −2.5 Diopter and −6.0 Diopter. It is noted from FIG. 27 that there is no significant difference in cylinder power $J_0$ for an emmetropic eye and patients with low, moderate and high amounts of myopia. It is further noted from FIG. 27 that cylinder power $J_0$ varies with visual field angle for the different groups of patients with increased astigmatism in the peripheral regions (e.g., at visual field angles with absolute value greater than about 10 degrees) as compared to the central region (e.g., at visual field angles between −10 degrees and +10 degrees).

Recent studies indicate that the amount of peripheral astigmatism is approximately the same for emmetropes, hypertoropes, low myopes, moderate myopes and high myopes. Thus, peripheral astigmatism can be considered to be independent of the foveal refractive state of the patient. Accordingly, the optical refractive characteristics of an IOL that is configured to correct for peripheral astigmatism can be determined without taking the foveal refractive state of the patient's eye. For example, in various embodiments of the IOL, the optical refractive characteristics of an IOL that is configured to correct for peripheral astigmatism can be determined by considering only the oblique incidence of light without taking into consideration any other ocular characteristics of the patient, such as for example, foveal refractive data, axial length of the eye, curvature of the cornea, etc.

As discussed above and noted from FIG. 27, the cylinder power varies nonlinearly with visual field angle. This nonlinear variation of the cylinder power with visual field angle can be quadratic with higher magnitude of cylindrical power in the peripheral regions (e.g., at visual field angles having an absolute value greater than or equal to 10 degrees) as compared to the central region (e.g., at visual field angles between −10 degrees and +10 degrees). In FIG. 27, the variation of the cylinder power decreases from a lower cylinder power in the central region, such as, for example, within a visual field angle of about ±10 degrees to a higher negative cylinder power in the peripheral regions, such as, for example, at visual field angle greater than or equal to about +10 degrees and/or less than or equal to −10 degrees. Accordingly, an IOL that is configured to correct for peripheral astigmatism can have an optical power distribution that varies inversely with the variation of the cylinder power such that the combination of the eye and the IOL reduces peripheral astigmatism. For example, the cylinder power of an IOL that compensates for peripheral astigmatism can increase nonlinearly from a lower cylinder power in the central region to a higher positive cylinder power in the peripheral regions such that the combination of the eye and the IOL has negligible astigmatic power in the peripheral regions. Various embodiments of the IOL can be configured to provide peripheral astigmatic correction at all visual field angles. Some embodiments of the IOL can be configured to provide astigmatic correction at certain specific visual field angles (e.g., ±15 degrees, ±20 degrees, ±25 degrees, ±30 degrees). An IOL configured to correct for peripheral astigmatism can include an arrangement of optical features (e.g. optical elements, grooves, volume or surface diffractive features, regions of varying refractive index, regions of varying curvatures, etc.) that results in the peripheral astigmatism having a desired dependence on eccentricity or field of view. Other methods of compensating peripheral astigmatism discussed above (such as correcting peripheral astigmatism using IOLs different shape factors, lens displacement or binocular summation) can be used simultaneously with designing an IOL having a cylinder power that varies nonlinearly with visual field angle (e.g., quadratic as discussed herein).

Figure 28:
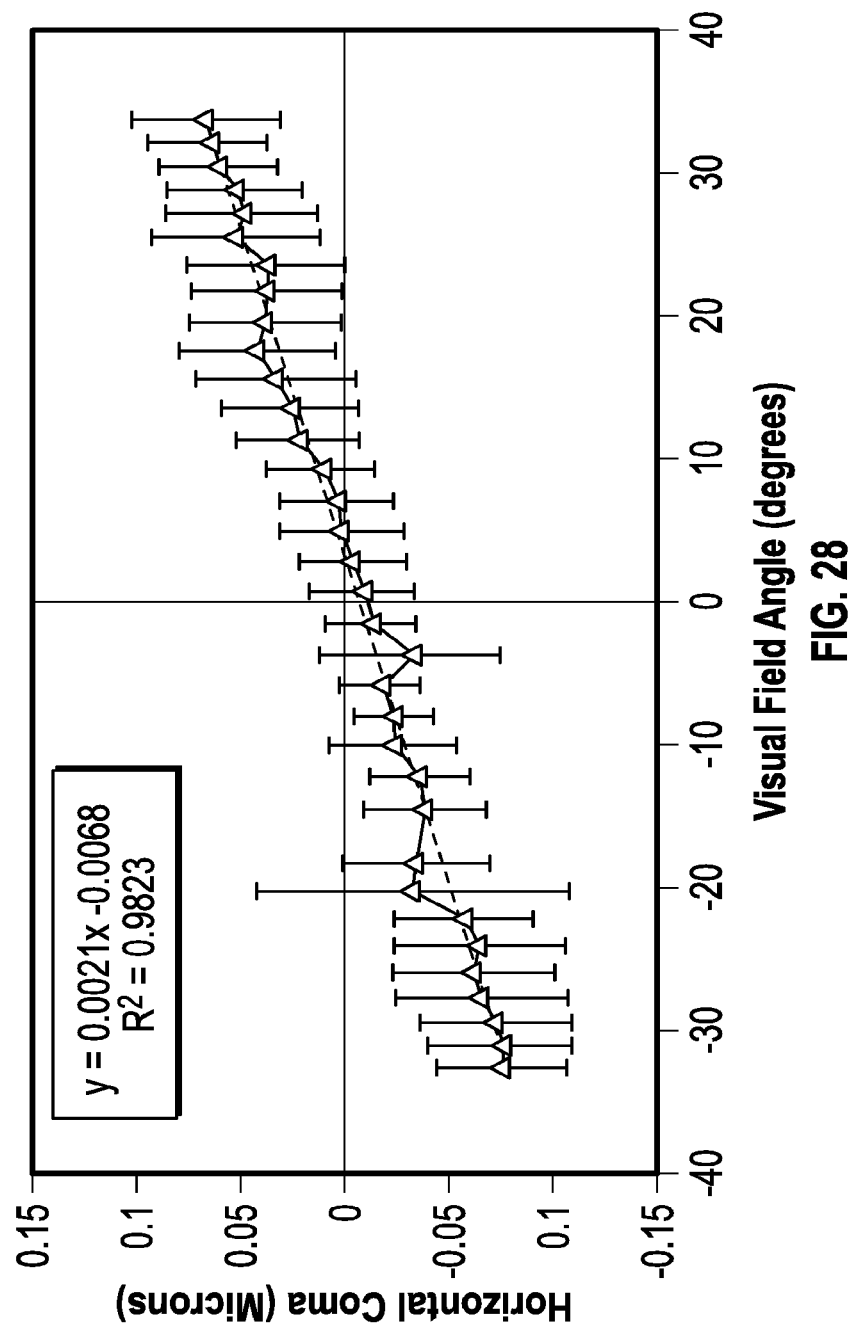
FIG. 28 is a graph illustrating the variation of horizontal coma as a function of visual field.

Another peripheral aberration that can be compensated to improve peripheral vision is horizontal coma. Recent studies indicate that similar to peripheral astigmatism, horizontal coma is also independent of the patient's ocular data, such as, for example, foveal refractive state, axial length of the cornea, corneal curvature, etc. FIG. 28 is a graph illustrating the variation of horizontal coma as a function of visual field. It is observed from FIG. 28 that horizontal coma increases linearly from a negative value at a visual field angle of about −30 degrees to a positive value at a visual field angle of about +30 degrees. Accordingly, an IOL configured to compensate for horizontal coma can have a horizontal coma that decreases linearly from a positive value at a visual field angle of about −30 degrees to a negative value at a visual field angle of about +30 degrees such that a combination of the eye and the IOL has negligible horizontal coma in the peripheral regions. Various embodiments of the IOL can be configured to compensate for horizontal coma at all visual field angles. Alternately, some embodiments of the IOL can be configured to compensate for horizontal coma at certain specific visual field angles (e.g., ±15 degrees, ±20 degrees, ±25 degrees, ±30 degrees). An IOL configured to correct for horizontal coma can include an arrangement of optical features (e.g. optical elements, grooves, volume or surface diffractive features, regions of varying refractive index, etc.) that results in the horizontal coma having a desired dependence on eccentricity or field of view. Other methods of compensating horizontal coma discussed above (such as correcting horizontal using IOLs different shape factors, lens displacement, etc.) can be used simultaneously with designing an IOL having a horizontal coma that varies linearly (e.g., decreases linearly) with visual field angle. It is advantageous to consider binocular mirror symmetry in higher order aberrations in IOLs configured to correct coma. For example, due to binocular mirror symmetry, horizontal coma in right and left eye have same magnitude but opposite sign. Thus, for the right eye, horizontal coma increases from negative values in the nasal peripheral region to positive values in the temporal peripheral region and for the left eye, horizontal coma increases from negative values in the temporal peripheral region to positive values in the nasal peripheral region. Accordingly, embodiments of IOL configured to correct horizontal coma can be designed by adopting appropriate sign conventions for right and left eye. Alternately, embodiments of IOL configured to correct horizontal coma can include markings that indicate the orientation for placement in right and left eyes.

Figure 29:
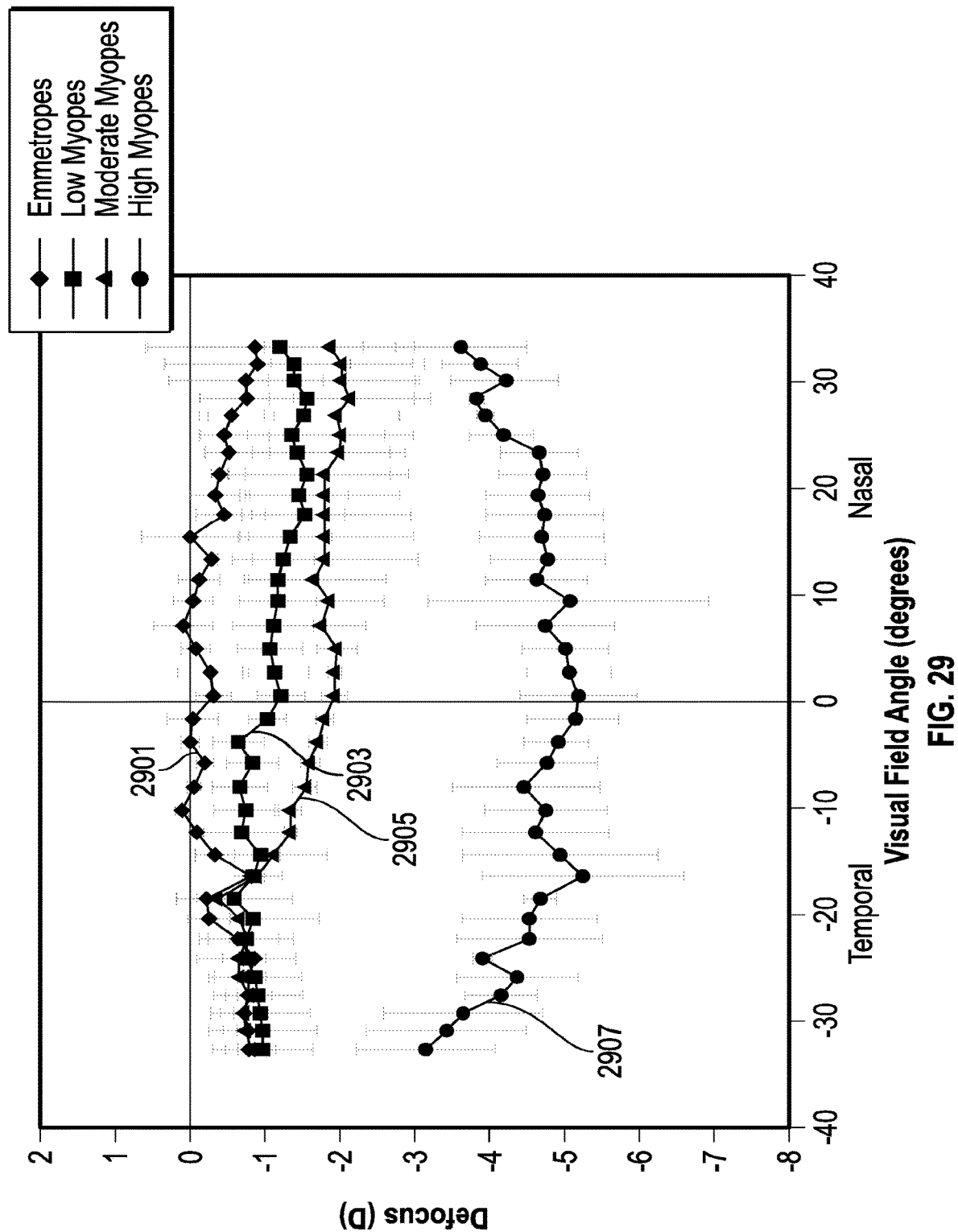
FIG. 29 is a graph illustrating the variation of defocus as a function of visual field for patients with different refractive error on axis.

Another peripheral aberration that can be compensated to improve peripheral vision is defocus. Unlike peripheral astigmatism and coma, peripheral defocus depends on the foveal refractive state of the patient. The effect of foveal refractive state on peripheral defocus is shown in FIG. 29 which illustrates the variation of defocus as a function of visual field angle for patients with different foveal refractive state (e.g., emmetropic eye, low myopia, moderate myopia and high myopia). Referring to FIG. 29, curve 2901 shows the variation of defocus versus visual field angle for an emmetropic eye as measured by COAS. In FIG. 29, curve 2903 shows the variation of defocus versus visual field angle for patients with low amount of myopia as measured by COAS. In FIG. 29, curve 2905 shows the variation of defocus versus visual field angle for patients with moderate amount of myopia as measured by COAS. In FIG. 29, curve 2907 shows the variation of spherical optical power versus visual field angle for patients with high amount of myopia as measured by COAS.

As noted from FIG. 29, peripheral defocus changes from a relative myopic shift characterized by higher negative optical power in the peripheral regions (e.g., at visual field angles having an absolute value greater than 10 degrees) as compared to the central region (e.g., at visual field angles between −10 degrees and +10 degrees) for an emmetropic eye or patients with low amount of myopia to a relative hyperopic shift characterized by lower negative optical power in the peripheral regions as compared to the central region for patients with moderate to high amounts of myopia. Accordingly, an IOL configured to compensate for peripheral defocus can have a greater amount of optical power in the peripheral regions as compared to the amount of optical power in the central region for an emmetropic eye or patients with low myopia and a smaller amount of optical power in the peripheral regions as compared to the optical power in the central region for patients with moderate to high myopia.

Various embodiments of an IOL configured to compensate for peripheral defocus in an emmetropic eye or patients with low amount of myopia can have a defocus power distribution that increases nonlinearly from the central region to the peripheral regions. In various embodiments, the optical power distribution can be symmetric about the central region such that the defocus power distribution for various embodiments of an IOL configured to compensate for peripheral defocus in an emmetropic eye or in patients with low amount of myopia is an increasing parabola. Various embodiments of an IOL configured to compensate for peripheral defocus in patients with moderate to high amount of myopia can have a defocus power distribution that decreases nonlinearly from the central region to the peripheral regions. In various embodiments, the defocus power distribution can be symmetric about the central region such that the defocus power distribution for various embodiments of an IOL configured to compensate for peripheral defocus in patients with moderate to high amount of myopia is a decreasing parabola.

In various implementations, the optical power distribution that can correct peripheral aberrations (e.g., astigmatism, coma, defocus, etc.) can depend on the refractive power of the IOL. In various embodiments, the refractive power of the IOL can be spherical and/or cylindrical power that can achieve emmetropia, Thus, patients with high myopia can benefit from low IOL powers while emmetropes can benefit from optical powers around 20-24 D and patients with hyperopia can benefit from high cylinder powers. Therefore, the optical power distribution that can reduce peripheral defocus can depend on the refractive power of the IOL. An example embodiment of an IOL configured to compensate for peripheral defocus in an emmetropic eye (e.g., an eye with spherical equivalent error between about −0.5 Diopter and about +0.5 Diopter) having a peripheral defocus power distribution similar to the distribution illustrated by curve 2901 has an optical defocus between about −0.1-+1.0 Diopter at visual field angles between about +10 degrees to +30 degrees and/or between about −10 degrees to −30 degrees. Another example embodiment of an IOL configured to compensate for peripheral defocus in patients with low myopia (e.g., with spherical equivalent power between about −0.5 Diopter and about −1.5 Diopter) having a defocus power distribution similar to the distribution illustrated by curve 2903 has an optical defocus between about −0.1-+2.0 Diopter at visual field angles between about +10 degrees to +30 degrees and/or between about −10 degrees to −30 degrees. Yet another example embodiment of an IOL configured to compensate for peripheral defocus in patients with moderate myopia (e.g., with spherical equivalent power between about −1.5 Diopter and about −2.5 Diopter) having a defocus power distribution similar to the distribution illustrated by curve 2905 has an optical defocus between about +1.0-+3.0 Diopter at visual field angles between about +10 degrees to +30 degrees and/or between about −10 degrees to −30 degrees. Another example embodiment of an IOL configured to compensate for peripheral defocus in patients with high myopia (e.g., with spherical equivalent power between about −2.5 Diopter and about −6.0 Diopter) having a defocus power distribution similar to the distribution illustrated by curve 2907 has an optical defocus between about +2.5-+6.0 Diopter at visual field angles between about +10 degrees to +30 degrees and/or between about −10 degrees to −30 degrees. Various embodiments of the IOL can be configured to compensate for defocus at all visual field angles. Alternately, some embodiments of the IOL can be configured to compensate for defocus at certain specific visual field angles (e.g., ±15 degrees, ±20 degrees, ±25 degrees, ±30 degrees). Other methods of compensating peripheral defocus discussed above (such as correcting horizontal using IOLs different shape factors, lens displacement, etc.) can be used simultaneously with designing an IOL having a defocus power distribution that is based on the foveal refractive state of the patient.

Because peripheral defocus is related to axial length and corneal power, and these parameters are the basic input for IOL power determination, the IOL designs to correct peripheral defocus also depends on the IOL spherical power to achieve emmetropia. Emmetropes (e.g., eyes with spherical equivalent error between about +0.5 Diopter and about −0.5 Diopter) have IOL powers around 20-24 D. Therefore, previous embodiments to correct peripheral defocus in emmetropes can be extended to lens with IOL powers around 20-24 D. Myopes require lower IOL powers than emmetropes (the higher the myopic error, the lower the IOL power) and hyperopes require higher IOL powers than emmetropes (the higher the hyperopic error, the higher the IOL power). Therefore, IOL designs described herein to correct peripheral defocus can depend on the spherical power of the IOL.

Metrics for Evaluating the Peripheral Image Quality of IOLs

Various implementations of IOLs described herein can improve peripheral image quality by correcting for peripheral errors. One method of designing implementations of IOLs that can improve peripheral image quality includes optimizing the image quality at multiple regions of the retina such as, for example, the fovea, and additional points in the region of the retina surrounding the fovea. While, it may be possible to optimize the image quality at every point of the central and peripheral visual field, this approach may be time intensive and/or computationally intensive. Accordingly, it is conceived that algorithms that determine the image quality at fewer points along the retina are employed to design implementations of IOLs that can improve peripheral image quality without degrading foveal image quality. Different metrics can be used to evaluate the peripheral image quality of various lens designs. The presence of large amounts of peripheral aberrations, such as coma, in the population can render the traditional metrics that have been developed to evaluate the foveal image quality of existing IOLs insufficient to evaluate the peripheral image quality of an IOL that is configured to improve peripheral image quality. For example, a frequently used metric to characterize the image quality at the fovea of existing IOLs, the visual Strehl OTF ratio, depends on foveal neural sensitivity which may not be suitable to evaluate peripheral image quality.

Figure 30A:
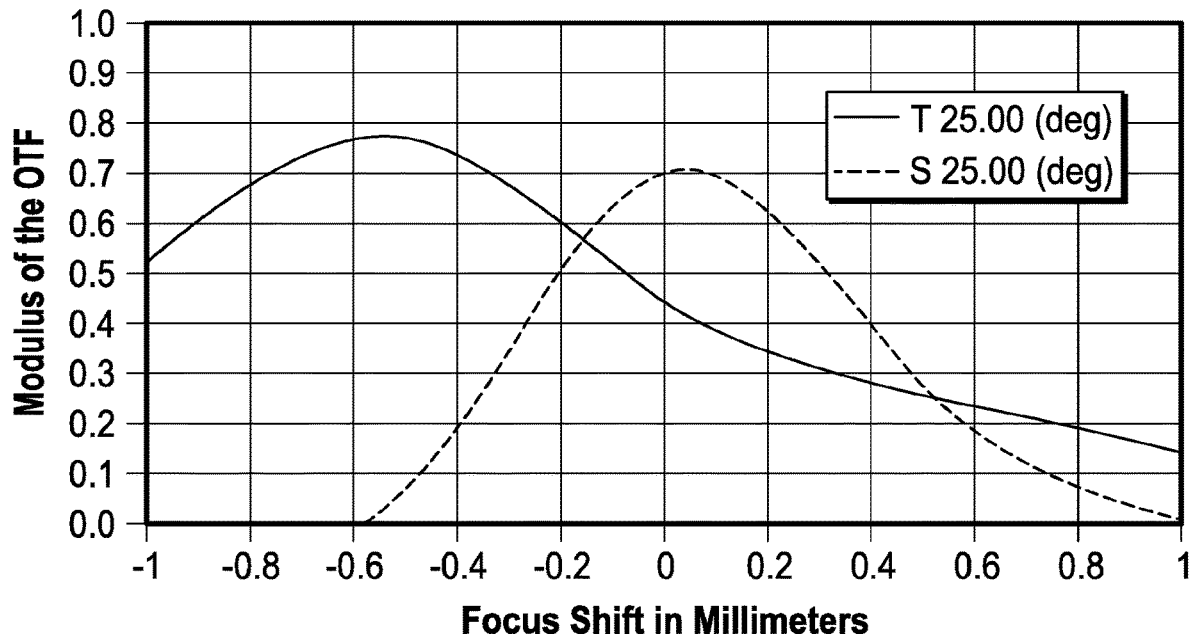
FIG. 30A illustrates the through-focus MTF for an implementation of a lens having a cylindrical error of about 8.4 Diopter for an image formed at a location of the peripheral retina centered at 25 degrees eccentricity in green light at 10 cycles/mm.
Figure 30B:
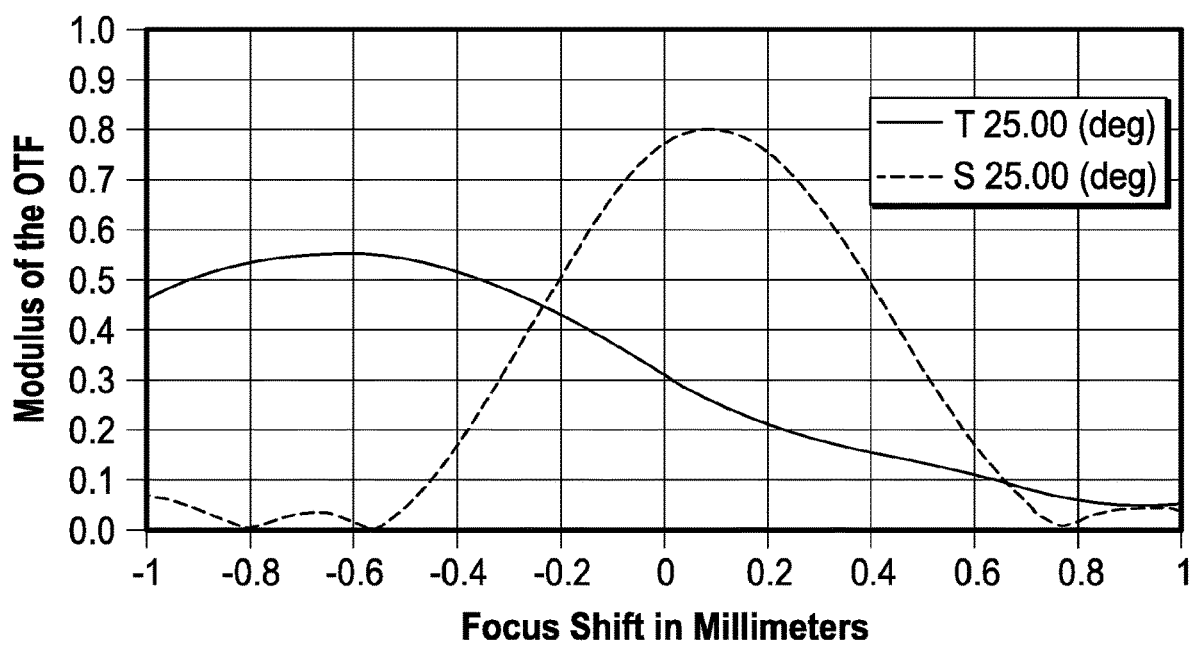
FIG. 30B illustrates the through-focus MTF for an implementation of a lens having a cylindrical error of about 1.2 Diopter for an image formed at a location of the peripheral retina centered at 25 degrees eccentricity in green light at 10 cycles/mm.
Figure 30C:
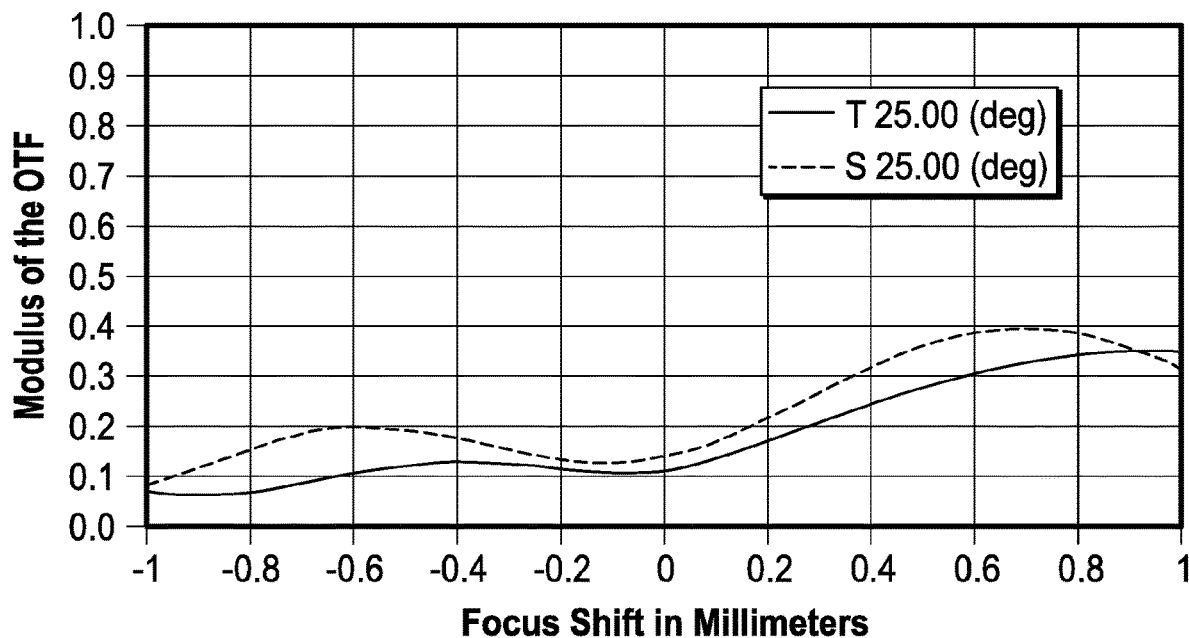
FIG. 30C illustrates the through-focus MTF for an implementation of a lens having a cylindrical error of about 0.75 Diopter for an image formed at a location of the peripheral retina centered at 25 degrees eccentricity in green light at 10 cycles/mm.

It has been proposed to use spherical and cylindrical errors in the peripheral visual field as a metric for evaluating the optical performance of different peripheral optics. This approach may be reasonable for phakic eyes, although some accuracy can be gained if higher order aberrations are included as well. However, when modeling lens designs that can improve peripheral image quality, metrics based on only spherical and/or cylindrical errors or single aberration coefficients can be inadequate. This is explained with reference to FIGS. 30A-30C which illustrate the through-focus MTF curves for three lens designs evaluated at 25 degrees eccentricity in green light at 10 cycles/mm. All the three lens designs have a spherical error of 0. The first lens design whose performance is illustrated in FIG. 30A has a cylindrical (or astigmatic) error J0=8.4 Diopters. The peak MTF for tangential rays focused by the first lens design is about 0.78 and the peak MTF for sagittal rays focused by the first lens design is about 0.7. The second lens design whose performance is illustrated in FIG. 30B has a cylindrical (or astigmatic) error J0=1.2 Diopter. The peak MTF for tangential rays focused by the second lens design is about 0.55 and the peak MTF for sagittal rays focused by the first lens design is about 0.8. The third lens design whose performance is illustrated in FIG. 30C has a cylindrical (or astigmatic) error J0=0.75 Diopter. The peak MTF for tangential rays focused by the third lens design is about 0.35 and the peak MTF for sagittal rays focused by the first lens design is about 0.4. It is observed from the MTF curves that while the astigmatic error for the third lens design is the lowest of the three lens designs, the peak MTF values for tangential rays and sagittal rays focused by the third lens design are lower than the peak MTF values for the first and the second lens. Thus, if only the refractive and cylindrical errors were considered to evaluate the different lens designs, then the third lens design would be selected over the first and second lens designs, even though the image quality provided the first and second lens designs at the peripheral retinal location is better than the third lens design. Therefore, it can advantageous to develop a new metric that can evaluate the image quality provided by different lens designs at the peripheral retinal location.

This disclosure contemplates utilizing a metric based on the Modulation Transfer Function (MTF) to evaluate the peripheral image quality for different lens designs that are configured to improve peripheral image quality. An example of a metric to evaluate the peripheral image quality can be a weighted average of MTF values at different spatial frequencies and at different eccentricities. Another example of a metric to evaluate the peripheral image quality can be an area under the through focus MTF curve obtained for multiple spatial frequencies and different eccentricities.

The metrics described herein can be obtained from pre-clinical measurements of an IOL design performed by a bench-top optical system or by performing simulations using an eye model. The metrics can be used to predict visual performance at different eccentricities for a range of spatial frequencies. For example, the metrics discussed herein can predict the image quality of a lens design when implanted in the eye for different eccentricities (e.g. 5 degrees, 10 degrees, 15 degrees, 20 degrees, 25 degrees, 30 degrees, or values therebetween) and a for a range of spatial frequencies between about 0 cycles per mm and about 50 cycles per mm, or about 0 cycles per mm and about 100 cycles per mm, or about 0 cycles per mm and about 200 cycles per mm.

The metrics described herein can be used to rank the visual performance of different lens designs and thus can be used to select lenses that would provide optical performance that would best suit the needs of a patient when implanted in the eye of the patient. The metrics described herein can also be used to preform pre-clinical assessment of safety and efficacy of new lens designs and select which among the new IOL designs can be used in clinical trials. The metrics described herein can also be used as a design tool to improve the performance of new and existing IOLs. The metrics described herein can be used for development and optimization of monofocal lenses, enhanced monofocal lenses, extended depth of focus lenses, multifocal lenses, extended range of vision lenses. The metrics described herein can be used to develop new categories of lenses.

Figure 31:
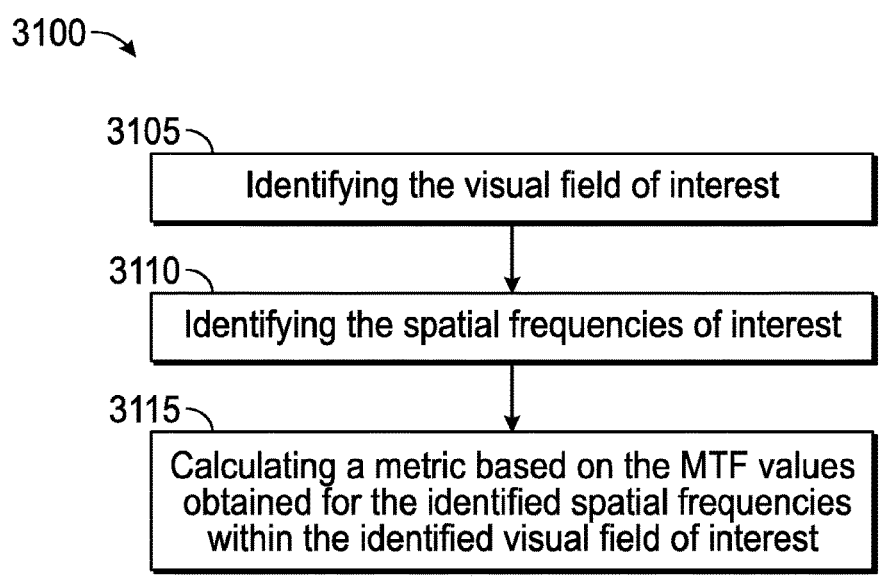
FIG. 31 illustrates a flowchart depicting an implementation of a method to obtain a metric used to evaluate the peripheral image quality provided by an implementation of a lens.

FIG. 31 illustrates a flowchart 3100 depicting an implementation of a method to obtain a metric (also referred to as a Figure of Merit (FoM)) that can be used to evaluate the peripheral image quality provided by a lens design. The method comprises identifying the visual field of interest as shown in block 3105. Identifying the visual field of interest can include, determining which part of the visual field should be considered to evaluate the optical performance of a lens design. For example, the visual field of interest can include the foveal region as well as the peripheral retinal region. As another example, the visual field of interest can include only the peripheral portions of the retina. In various implementations, the visual field of interest can include a region having eccentricity greater than or equal to about 0 degrees (corresponding to the foveal location) and less than or equal to about 30 degrees. For example, the visual field of interest can include regions having eccentricity greater than or equal to about 0 degrees (corresponding to the foveal location) and less than or equal to about 10 degrees, greater than or equal to about 0 degrees (corresponding to the foveal location) and less than or equal to about 15 degrees, greater than or equal to about 0 degrees (corresponding to the foveal location) and less than or equal to about 20 degrees, greater than or equal to about 0 degrees (corresponding to the foveal location) and less than or equal to about 30 degrees, greater than or equal to about 5 degrees (corresponding to the foveal location) and less than or equal to about 30 degrees, greater than or equal to about 10 degrees (corresponding to the foveal location) and less than or equal to about 30 degrees, etc. Without any loss of generality, a retinal location having an eccentricity of $\theta$ degrees can lie on a circle that is centered about the fovea and oriented such that a tangential line to the circle forms an angle of about $\theta$-degrees with respect to the optical axis of the eye.

The method further comprises identifying the spatial frequencies of interest for which the MTF is to be calculated, as shown in block 3110. The spatial frequencies of interest can be between greater than or equal to 0 cycles/mm and less than or equal to 200 cycles/mm. For example, the spatial frequencies of interest can be greater than or equal to 0 cycles/mm and less than or equal to 30 cycles/mm, greater than or equal to 0 cycles/mm and less than or equal to 50 cycles/mm, greater than or equal to 0 cycles/mm and less than or equal to 100 cycles/mm, greater than or equal to 10 cycles/mm and less than or equal to 200 cycles/mm, greater than or equal to 50 cycles/mm and less than or equal to 200 cycles/mm, greater than or equal to 0 cycles/mm and less than or equal to 100 cycles/mm, etc. The MTF can be calculated for different illumination conditions, such as, for example, illumination provided by a white light source or a green light source.

The method further comprises calculating a metric based on the MTF values obtained for the identified spatial frequencies within the identified visual field of interest, as shown in block 3115. The metric can be calculated by taking an average of the obtained MTF values. For example, the metric can be a weighted average of the obtained MTF values wherein different weights are assigned to the MTF values obtained for different spatial frequencies and different eccentricities.

The identification of the visual field of interest and the spatial frequencies can be based on the ocular anatomy and functional tasks that are desired to be improved. The functional tasks can include pattern detection, pattern recognition, luminance detection, car driving, walking, navigation, reading, tasks performed in photopic conditions, tasks performed in scotopic conditions, etc. The ocular anatomy can include photoreceptor density, iris structure, ganglion cell density, pupil size, shape and size of retina, etc. The metrics described herein can be calculated for an entire population or a group of patients based on average population statistic. Alternately, the metric can be calculated for a specific patient based on the patient's specific eye geometry and the specific functional requirements of the patient.

Example Metric to Evaluate Peripheral Image Quality

An example of a metric that can be used to evaluate peripheral image quality is described below. The visual field of interest is identified. As discussed above, the visual field of interest can be selected based on the functional tasks to be performed and/or the ocular anatomy. For the purpose of the illustrative example, the visual field of interest is selected to be a circular region of the retina having an eccentricity up to 30 degrees. The retinal region having an eccentricity up to 30 degrees is advantageous for driving. Different eccentricities can be selected for other tasks. For example, the visual field of interest selected for pattern detection and/or pattern recognition may be smaller than 30 degrees. In the illustrative example, MTF curves can be obtained for eccentricities in increments of 5 degrees between 0 degrees and 30 degrees. For example, MTF curves can be obtained at eccentricities of 0 degrees (corresponding to the foveal region), 5 degrees, 10 degrees, 15 degrees, 20 degrees, 25 degrees and 30 degrees. In other implementations, MTF curves can be obtained for more or less eccentricities in the selected visual field of interest.

Figure 32:
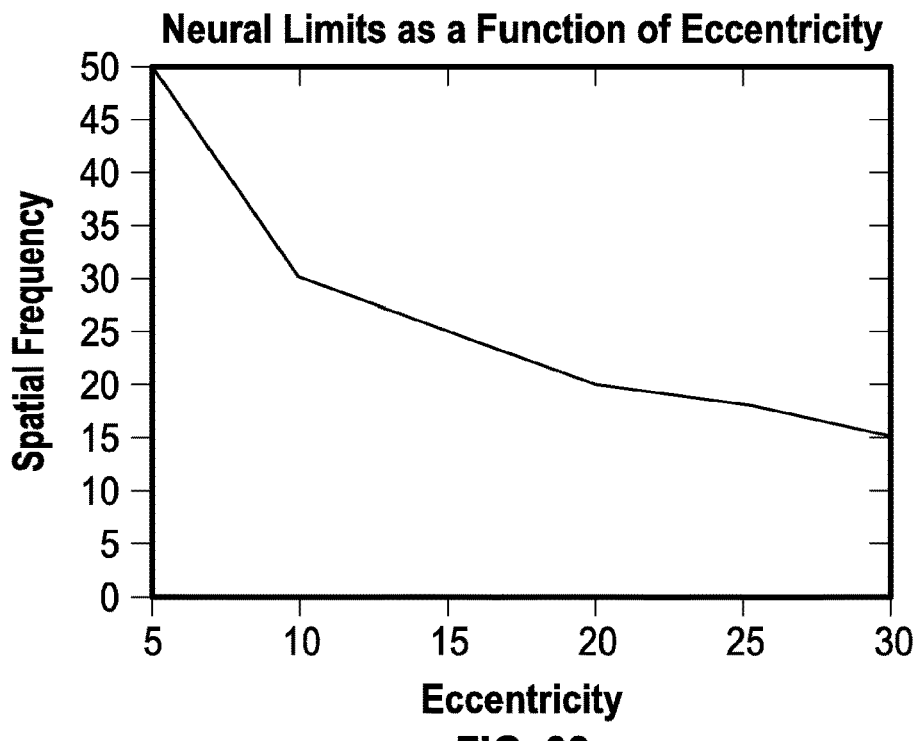
FIG. 32 illustrates the spatial frequency that is achievable based on the ganglion cell density at different eccentricities.

As discussed above, the spatial frequencies of interest can be selected based on the ocular anatomy and the functional tasks that are to be performed. The ganglion cell density in the peripheral retina is less than the ganglion cell density in the central retina. Accordingly, the contrast ratio of an image formed on the peripheral retina can be lower than the contrast ratio of an image formed on the central retina. Additionally, tasks (such as driving, walking, etc.) that can benefit from improved peripheral image quality can be performed at low spatial frequencies and low contrast ratios. Thus, it may not be necessary to evaluate lens designs for higher spatial frequencies (e.g., 50 cycles/mm, 100 cycles/mm or higher). Instead, it may be advantageous to evaluate lens designs for lower spatial frequencies. Since the ganglion cell density limits the maximum peripheral resolution that can be achieved if all peripheral errors and aberrations are corrected, the range of spatial frequencies can be selected using the distribution of ganglion cell density in the visual field of interest. FIG. 32 illustrates the spatial frequency that is achievable based on the ganglion cell density at different eccentricities. It is observed from FIG. 32 that the ganglion cell density limits the maximum achievable spatial frequency to about 50 cycles/mm at an eccentricity of about 5 degrees and to about 15 cycles/mm at an eccentricity of about 15 degrees. In the illustrative example, the selected range of spatial frequencies is from 0 cycles/mm to 20 cycles/mm. In other example, the upper limit on the range of spatial frequencies can be greater than 20 cycles/mm. For example, the selected range of spatial frequencies can be from 0 cycles/mm to 25 cycles/mm, 0 cycles/mm to 30 cycles/mm, 0 cycles/mm to 35 cycles/mm, 0 cycles/mm to 40 cycles/mm, 0 cycles/mm to 45 cycles/mm or 0 cycles/mm to 50 cycles/mm.

Figure 33:
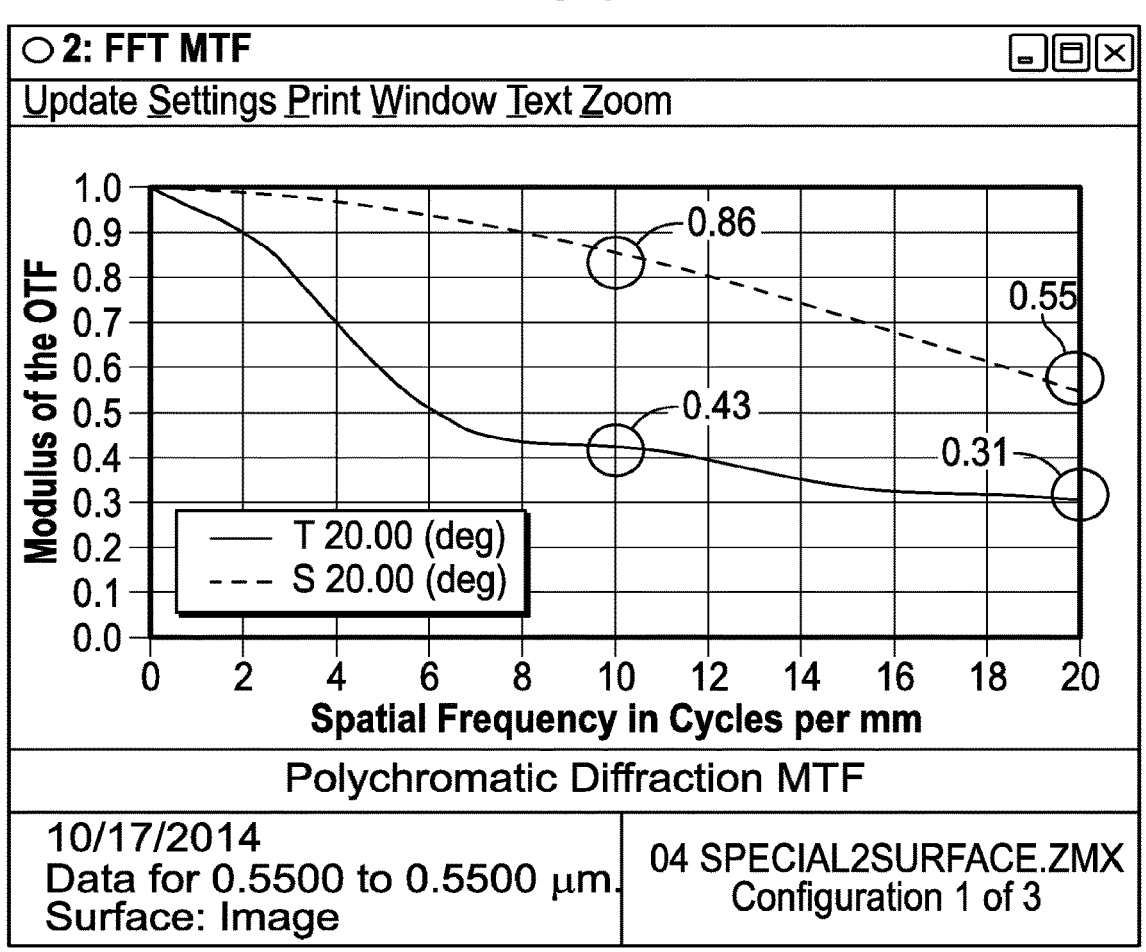
FIG. 33 shows the MTF curve for tangential and sagittal rays at an eccentricity of 20 degrees for spatial frequencies between 0 cycles/mm and 20 cycles/mm for an implementation of a lens in green light.

In the illustrative example, to calculate the metric MTF curves for tangential and sagittal rays are obtained at different eccentricity values from 5 degrees to 30 degrees in increments of 5 degrees for different spatial frequencies between 0 cycles/mm and 20 cycles/mm. FIG. 33 shows the MTF curve for tangential and sagittal rays at an eccentricity of 20 degrees for spatial frequencies between 0 cycles/mm and 20 cycles/mm for a lens design in green light. A metric can be obtained for each eccentricity to evaluate the image quality obtained at each eccentricity. A metric for the entire range of eccentricities can be obtained by averaging the metric obtained for each eccentricity.

In the illustrative example, the metric obtained at each eccentricity is based on the MTF values for tangential and sagittal rays at a spatial frequency of 10 cycles/mm and 20 cycles/mm. For example, the metric can be an arithmetic average or a geometric average of the MTF values for tangential and sagittal rays at a spatial frequency of 10 cycles/mm and 20 cycles/mm. As another example, the metric can be a weighted average of the MTF values for tangential and sagittal rays at a spatial frequency of 10 cycles/mm and 20 cycles/mm.

In other examples, the metric obtained at each eccentricity can be equal or proportional to the area under the MTF curve for all spatial frequencies in the selected range.

For the purpose of the illustrative example, the metric for each eccentricity is obtained by taking a geometric average of the MTF values for tangential and sagittal rays at a spatial frequency of 10 cycles/mm and 20 cycles/mm. Selecting geometric average as a metric can simplify the optimization process such that it converges toward a lens design in which the MTF values for both tangential and sagittal rays are above a threshold value thereby reducing the dependence of image quality on the orientation of the lens.

With reference to FIG. 33, the metric $FoM_{20}$ for an eccentricity of 20 degrees is given by:

$$FoM_{20} = \sqrt[4]{\sqrt{0.86 \times 0.43 \times 0.55 \times 0.31}} = 0.5$$

Once the metric for each eccentricity (e.g., 5-degrees, 10-degrees, 15-degrees, 20-degrees, 25-degrees and 30-degrees in the illustrative example) is obtained, the overall (also referred to as total) metric for the peripheral retina can be calculated. The overall metric can be an arithmetic average a geometric average or a weighted average of the metric obtained at each eccentricity.

With reference to FIG. 33, the overall metric $FoM_{total}$ is given by:

$$FoM_{total} = \sqrt[6]{FoM_5 \times FoM_{10} \times FoM_{15} \times FoM_{20} \times FoM_{25} \times FoM_{30}} = 0.64$$

The metrics described above can be used to compare and evaluate different lens designs. The foveal performance can be evaluated separately for each lens design. Alternately, the foveal performance can be included in the metric directly. For example, in various implementations, the overall metric can be calculated by including a figure of merit at 0 degree eccentricity ($FoM_0$) can be obtained for one or more spatial frequencies to include foveal performance. When included directly in the metric, the foveal performance can be weighted with an appropriate factor.

In various implementations, the range of spatial frequencies can be calculated based on photoreceptor data instead of ganglion cell density. Lenses optimized based on photoreceptor data instead of ganglion cell density can be suitable for detection tasks rather than tasks that require resolution. The pupil size can vary depending on the task. Accordingly, the variation of the pupil size can be taken into account when calculating the metrics to evaluate the optical performance of different lens designs. Chromatic effects can also be included into the metric. For example, transverse chromatic aberration can be larger in the periphery retina than in the fovea. Accordingly, correction of transverse chromatic aberration can be advantageous in improving the peripheral image quality. Other existing metrics adapted to foveal conditions can also be adapted to the peripheral conditions. For example, foveal metrics that take into consideration the elliptical pupil shape and reduced neural sensitivity can also be adapted to evaluate the peripheral image quality of various lens designs.

Lens Designs for Improving Peripheral Image Quality in IOLs

This disclosure contemplates a range of lens designs that can improve peripheral image quality while maintaining foveal image quality. The lens designs discussed herein can be applied to IOLs and other optical solutions (e.g., contact/spectacle lenses, laser ablation patterns, etc.). The implementations of lens designs described below include a lens with a first surface and a second surface intersected by an optical axis. The optical axis can pass through the geometric center of the lens and joins the centers of curvature of the first and the second surface. Various implementations of lenses discussed herein that are configured to improve peripheral image quality can be configured to be symmetric about the optical axis. An advantage of having symmetric lenses is that image quality in different visual fields can substantially equal. For example, if a symmetric lens is configured to provide good image quality in a left visual field, then it can also provide good image quality in a right visual field. Similarly, if a symmetric lens is configured to provide good image quality in a visual field upward with respect to an axis perpendicular to the optical axis, then it can also provide good image quality downward with respect to that axis. Another advantage of having symmetric lenses is that the image quality in a region around the optical axis is uniform. Accordingly, the image quality can be insensitive to the orientation of the lens. This may make the implantation process easier for the surgeon. Symmetric lenses may also have manufacturing advantages over the asymmetric lenses. The first and second surface of the implementations of lenses described herein can be spheric, aspheric, conic or any other shape. In various implementations of the lenses, one or both surfaces can be a higher order asphere described by the second, fourth, sixth, eight, tenth and $12^{th}$ order coefficients. Higher order aspheric surfaces can advantageously provide a plurality of degrees of freedom when designing the lens. Having plurality of degrees of freedom can be useful in designing lenses that provide sufficient image quality at the fovea as well as a peripheral retinal location.

The implementations of lenses described herein are configured to improve peripheral image quality without sacrificing foveal image quality. The implementations of lenses described below can be designed using the principles discussed above. For example, stop shift equations can be used to optimize the surfaces of the lenses based on their placement in the eye to reduce at least one optical aberration (e.g., defocus, astigmatism, coma, etc.) at the peripheral retinal location. As another example, the shape factor of the lenses described below can be optimized to reduce degradation of visual information obtained from the peripheral retinal location. As yet another example, the principal plane of the lenses described below can be shifted by modifying the shape factor of the lenses and/or by axially displacing the lenses to improve image quality at the peripheral retinal location. Additionally, the implementations of lenses described herein are configured to improve peripheral image quality without sacrificing foveal image quality in bright light (photopic conditions) as well as dim light (scotopic conditions). The peripheral image quality of each implementation of a lens is evaluated using a metric as described above, while the foveal image quality is evaluated by MTF at a spatial frequency of 100 cycles/mm in green light. Various implementations of lenses described herein have a through-focus MTF of at least 0.5 for a spatial frequency of 100 cycles/mm in green light for a large pupil having a diameter of 5 mm as well as a small pupil having a diameter of 3 mm. The surface profiles of the various lenses described below correspond to a base optical power of 20 Diopters.

Implementation of a Lens Currently Available in the Market Including an Aspheric Surface (Standard Lens)

The peripheral image quality of an implementation of a lens currently available in the market (also referred to as a standard lens) was evaluated using the metric discussed above as a baseline for comparing the different optical solutions. The standard lens can be similar to a standard toric IOL (e.g., TECNIS®). The overall figure of merit given by a geometric average of figures of merit obtained at different eccentricities between 5 degrees and 30 degrees in increments of 5 degrees as discussed above for the implementation of the standard lens was 0.40.

Figure 34A:
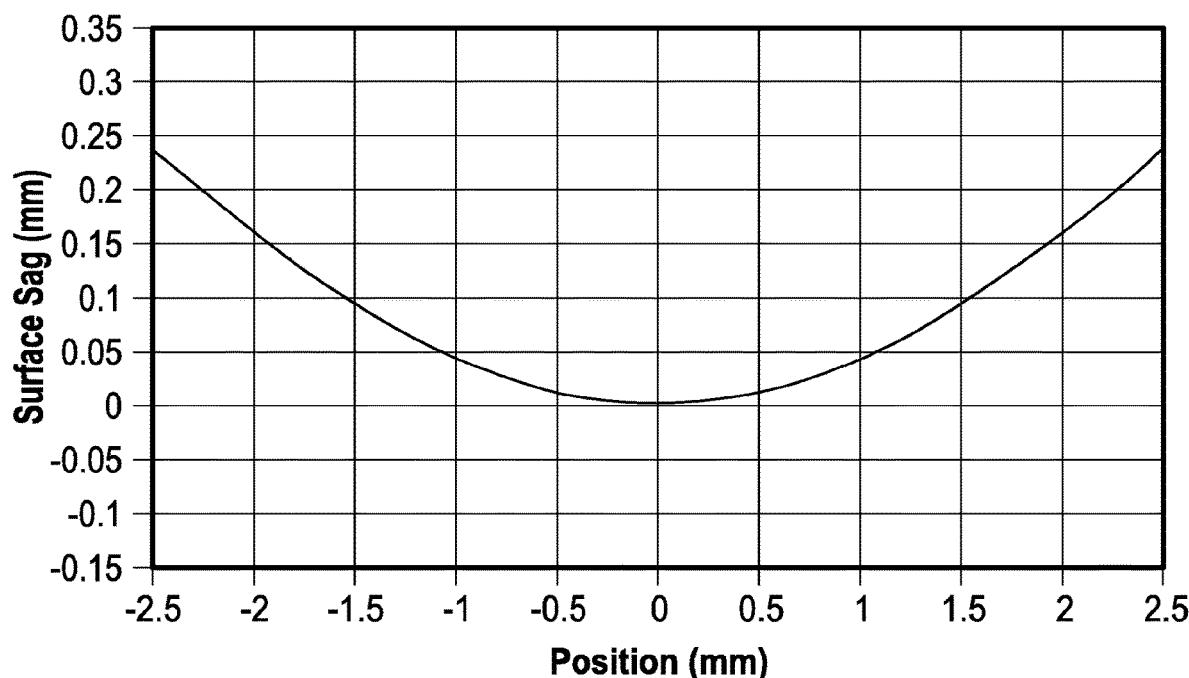
FIG. 34A illustrates the surface sag of a first surface of an implementation of a standard IOL and FIG. 34B illustrates the surface sag of a second surface of the standard IOL. FIG.
Figure 34B:
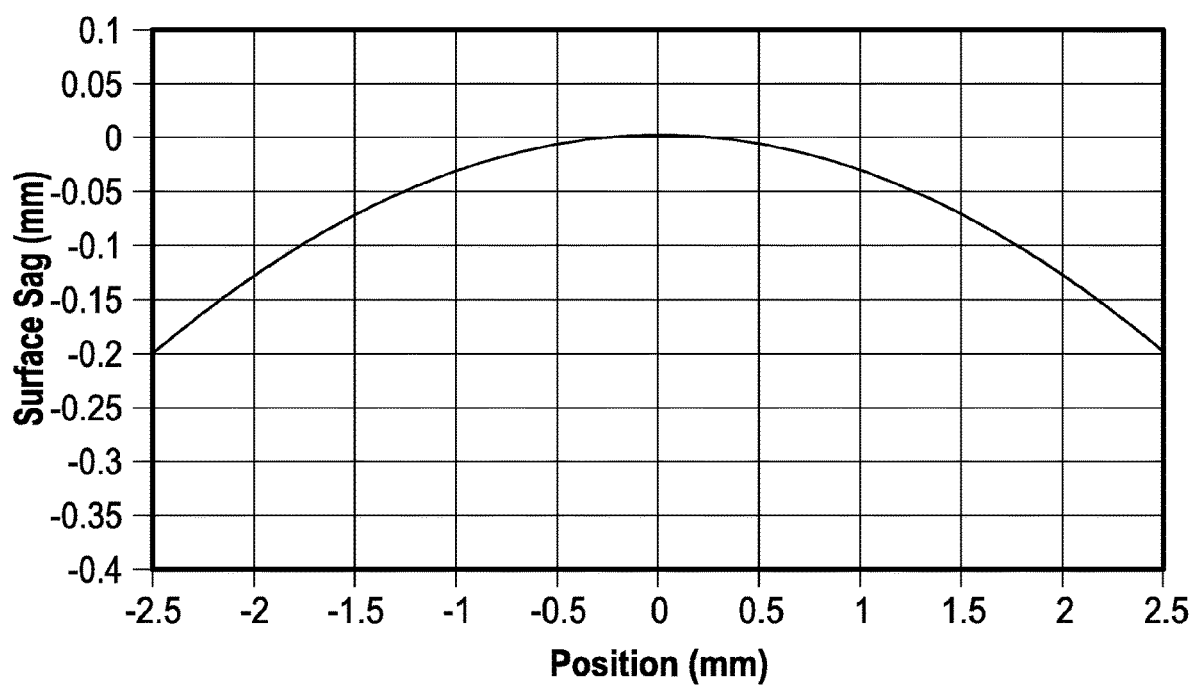

The implementation of the standard lens has a first surface and a second surface intersected by an optical axis that passes through the geometric center of the standard lens and joins the center of curvatures of the first and second surfaces. The first surface and second surface are both convex as noted from the surface sag profiles shown in FIGS. 34A and 34B. FIG. 34A illustrates the surface sag of the first surface on which light from the object is incident. The first surface of the lens can be referred to as an anterior surface which will face the cornea when the lens is implanted in the eye. FIG. 34B illustrates the surface sag of the second surface from which light incident on the lens exits the lens. The second surface of the lens can be referred to as a posterior surface which will face the retina when the lens is implanted in the eye. At least one of the first or the second surface of the lens is aspheric such that the lens is configured to enhance foveal image quality.

Figure 34C:
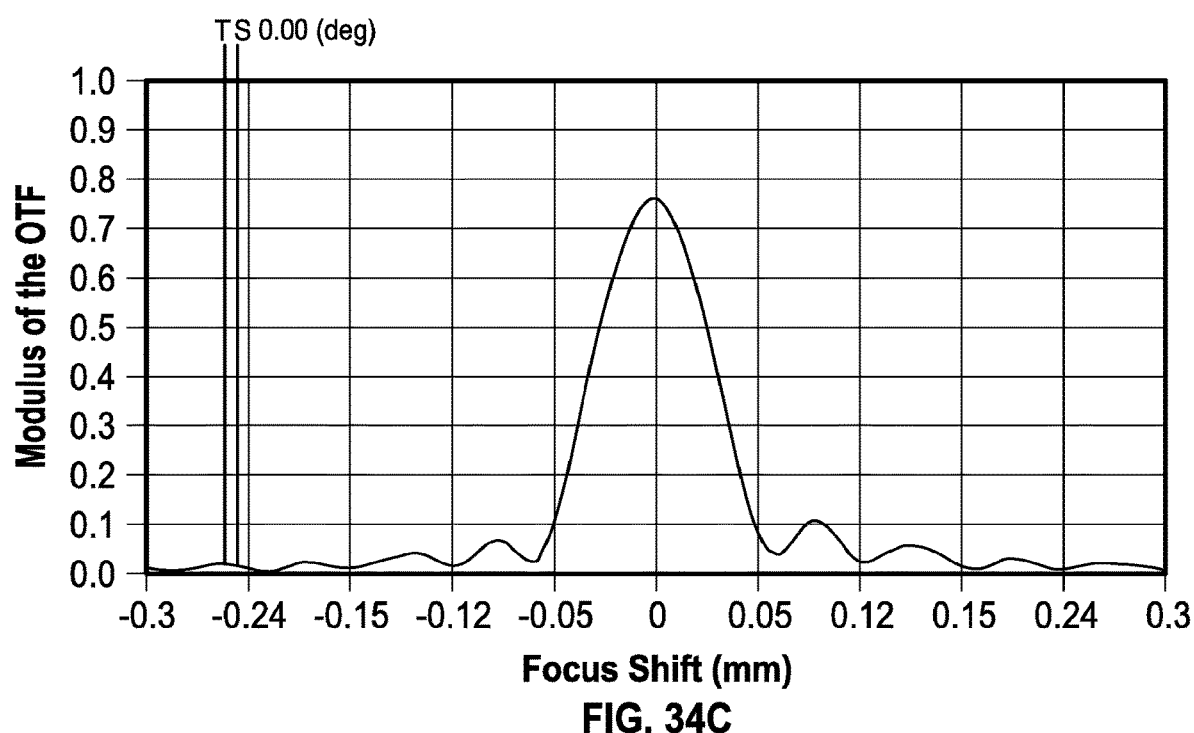

FIG. 34C illustrates the through-focus MTF at a spatial frequency of 100 cycles/mm in green light for a 5 mm pupil, which can be used to measure of the foveal image quality. As noted from FIG. 34C, the through-focus MTF at a spatial frequency of 100 cycles/mm in green light is about 0.76 indicating sufficient image quality at the fovea. Optical performance of the lens at different eccentricities between 0 to 30-degrees in increments of 5 degrees can be deduced from the data provided in Table 7.1 below. With reference to Table 7.1, M is the spherical defocus and J0 is the astigmatic error. It is observed from Table 7.1 that at an eccentricity of about 30-degrees, the implementation of the standard lens has an astigmatic error of −1.89 Diopters and a spherical defocus value of about −1.28 Diopters.

The maximum distance between the two surfaces of the standard lens along the optical axis (also referred to as thickness of the standard lens) can be between 0.5 mm and 1 mm. The standard lens can be placed in the capsular such that the distance between the pupil and the anterior surface of the lens is small. For example, the implementation of lenses disclosed above can be implanted such that the distance between the pupil and the anterior surface of the lens is between 0.9 mm and 1.5 mm (e.g., 0.75 mm).

TABLE 7.1

| Angle | M | J0 |
|---|---|---|
| 0 | 0 | 0 |
| 5 | −0.05 | −0.06 |
| 10 | −0.18 | −0.24 |
| 15 | −0.39 | −0.53 |
| 20 | −0.66 | −0.92 |
| 25 | −0.96 | −1.38 |
| 30 | −1.28 | −1.89 |

Meniscus Lens

An implementation of a meniscus lens was designed according to the concepts discussed above to improve peripheral image quality without sacrificing foveal image quality. The implementation of the meniscus lens has a first surface and a second surface intersected by an optical axis that passes through the geometric center of the meniscus lens and joins the center of curvatures of the first and second surfaces. FIG. 35A illustrates the surface sag of the first surface on which light from the object is incident. The first surface of the lens can be referred to as an anterior surface which will face the cornea when the lens is implanted in the eye. FIG. 35B illustrates the surface sag of the second surface from which light incident on the lens exits the lens. The second surface of the lens can be referred to as a posterior surface which will face the retina when the lens is implanted in the eye. The first surface is concave and the second surface is convex as noted from the surface sag profiles shown in FIGS. 35A and 35B. In other words, the first surface and the second surface bend the same way with a vertex of the lens curving inwards from the edges of the lens. The thickness and the placement of the meniscus lens can be similar to the thickness and the placement of the standard lens discussed above. The meniscus lens is designed based on an assumption that a distance between the pupil and the lens will, when combined with the right shape factor, substantially decrease the peripheral astigmatism. The overall figure of merit given by a geometric average of figures of merit obtained at different eccentricities between 5 degrees and 30 degrees in increments of 5 degrees as discussed above for the implementation of meniscus lens was 0.41.

The foveal image quality for the implementation of the meniscus lens can be evaluated using the through-focus MTF at a spatial frequency of 100 cycles/mm in green light for a 5 mm pupil, illustrated in FIG. 35C. As noted from FIG. 35C, the through-focus MTF at a spatial frequency of 100 cycles/mm in green light is about 0.75 indicating sufficient image quality at the fovea. Optical performance of the lens at different eccentricities between 0 to 30-degrees in increments of 5 degrees can be deduced from the data provided in Table 7.2 below. With reference to Table 7.2, M is the spherical defocus and J0 is the astigmatic error. It is observed from Table 7.2 that at an eccentricity of about 30-degrees, the implementation of the meniscus lens has an astigmatic error of −1.14 Diopters and a spherical defocus value of about −0.31 Diopters.

TABLE 7.2

| Angle | M | J0 |
|---|---|---|
| 0 | 0 | 0 |
| 5 | 0 | −0.04 |
| 10 | 0 | −0.15 |
| 15 | 0 | −0.33 |
| 20 | 0.04 | −0.57 |
| 25 | 0.13 | −0.84 |
| 30 | 0.31 | −1.14 |

A comparison of the optical performance of the implementation of the meniscus lens and the standard lens shows that the implementation of the meniscus lens configured to improve peripheral image quality has a foveal image quality that is substantially equal to or within a margin of error of the foveal image quality of the standard lens. Additionally, the implementation of the meniscus lens has a depth of focus, represented by the full width of the through-focus MTF peak at a threshold MTF value (e.g., 0.2, 0.3, 0.4 or 0.5) that is substantially equal to or within a margin of error of the depth of focus provided by the standard lens. Spherical defocus (M) and the astigmatic error (J0) provided by the implementation of the meniscus lens is lower than the spherical defocus (M) and the astigmatic error (J0) provided by the standard lens. Accordingly, the implementation of the meniscus lens can reduce peripheral refraction errors without degrading the foveal image quality. Various physical and optical characteristics of the meniscus lens described herein can be similar to the physical and optical characteristics of the various lenses that are configured to focus obliquely incident light at a peripheral retinal location as described in U.S. application Ser. No. 14/644,101 filed on Mar. 10, 2015, titled 'Dual-Optic Intraocular Lens that Improves Overall Vision where there is a Local Loss of Retinal Function;" U.S. application Ser. No. 14/644,110 filed on Mar. 10, 2015, titled 'Enhanced Toric Lens that Improves Overall Vision where there is a Local Loss of Retinal Function;" U.S. application Ser. No. 14/644,107 filed on Mar. 10, 2015, titled 'Piggyback Intraocular Lens that Improves Overall Vision where there is a Local Loss of Retinal Function;" and U.S. application Ser. No. 14/644,082 filed on Mar. 10, 2015, titled 'Intraocular Lens that Improves Overall Vision where there is a Local Loss of Retinal Function." Each of the above-identified application is hereby incorporated by reference herein in its entirety for all that it discloses and is made a part of this application.

Double Aspheric Lens

An implementation of a double aspheric lens was designed according to the concepts discussed above to improve peripheral image quality without sacrificing foveal image quality. The implementation of the double aspheric lens has a first surface and a second surface intersected by an optical axis that passes through the geometric center of the double aspheric lens and joins the center of curvatures of the first and second surfaces. FIG. 36A illustrates the surface sag of the first surface on which light from the object is incident. The first surface of the lens can be referred to as an anterior surface which will face the cornea when the lens is implanted in the eye. FIG. 36B illustrates the surface sag of the second surface from which light incident on the lens exits the lens. The second surface of the lens can be referred to as a posterior surface which will face the retina when the lens is implanted in the eye. Both the first and the second surface are higher order aspheric surfaces including up to twelfth ($12^{th}$) order aspheric terms. For example, the first surface and/or the second surface can be described mathematically by the equation below:

$$z = \frac{cr^2}{1 + \sqrt{1-(1+k)c^2r^2}} + \sum_{i=1}^{6} \alpha_i r^{2i}$$

where z is the sag of the surface, c is the curvature of the surface, r the radial distance from the optical axis, k the conic constant and $\alpha_1, \ldots, \alpha_{12}$, are the aspheric coefficients. Without any loss of generality, the curvature of the surface can be correlated to the inverse of the radius of curvature R. The surface described by the above equation is symmetric about the optical axis and thus does not have any angular dependency. Accordingly, the optical effect (and/or image quality) is independent of angular location.

The values of the surface parameters such as radius of curvature, aspheric coefficients, conic constant, etc. can be different for the first and the second surface. For example, the surface that faces the cornea can have a high conic constant (e.g., between 10 and 1000) and the surface that faces the retina can have a low conic constant (e.g., between 0 and 10). The curvature of the second surface can be greater than or lesser than the curvature of the first surface. In the particular implementation described herein, other parameters of the lens (e.g., thickness and placement) are similar to the standard lens.

The foveal image quality for the implementation of the double aspheric lens can be evaluated using the through-focus MTF at a spatial frequency of 100 cycles/mm in green light for a 5 mm pupil, illustrated in FIG. 36C. As noted from FIG. 36C, the through-focus MTF at a spatial frequency of 100 cycles/mm in green light is about 0.74 indicating sufficient image quality at the fovea. Optical performance of the double aspheric lens at different eccentricities between 0 to 30-degrees in increments of 5 degrees can be deduced from the data provided in Table 7.3 below. With reference to Table 7.3, M is the spherical defocus and J0 is the astigmatic error. It is observed from Table 7.3 that at an eccentricity of about 30-degrees, the implementation of the double aspheric lens has an astigmatic error of −1.39 Diopters and a spherical defocus value of about −0.27 Diopters. The overall figure of merit given by a geometric average of figures of merit obtained at different eccentricities between 5 degrees and 30 degrees in increments of 5 degrees as discussed above for the implementation of double aspheric lens was 0.50 corresponding to an average contrast ratio increase of about 25% as compared to the standard lens.

TABLE 7.3

| Angle | M | J0 |
|---|---|---|
| 0 | −0.02 | 0 |
| 5 | −0.04 | −0.05 |
| 10 | −0.09 | −0.19 |
| 15 | −0.17 | −0.41 |
| 20 | −0.24 | −0.70 |
| 25 | −0.28 | −1.04 |
| 30 | −0.27 | −1.39 |

A comparison of the optical performance of the implementation of the double aspheric lens and the standard lens shows that the implementation of the double aspheric lens configured to improve peripheral image quality has a foveal image quality that is substantially equal to or within a margin of error of the foveal image quality of the standard lens. Additionally, the implementation of the double aspheric lens has a depth of focus, represented by the full width of the through-focus MTF peak at a threshold MTF value (e.g., 0.2, 0.3, 0.4 or 0.5) that is substantially equal to or within a margin of error of the depth of focus provided by the standard lens. Spherical defocus (M) and the astigmatic error (J0) provided by the implementation of the double aspheric lens is lower than the spherical defocus (M) and the astigmatic error (J0) provided by the standard lens. Additionally, the implementation of the double aspheric lens provides about 25% increase in the contrast ratio as compared to the standard lens. Accordingly, the implementation of the double aspheric lens can reduce peripheral refraction errors and improve peripheral image quality without degrading the foveal image quality. Various physical and optical characteristics of the double aspheric lens described herein can be similar to the physical and optical characteristics of the various lenses that are configured to focus obliquely incident light at a peripheral retinal location as described in U.S. application Ser. No. 14/644,101 filed on Mar. 10, 2015, titled 'Dual-Optic Intraocular Lens that Improves Overall Vision where there is a Local Loss of Retinal Function;" U.S. application Ser. No. 14/644,110 filed on Mar. 10, 2015, titled 'Enhanced Toric Lens that Improves Overall Vision where there is a Local Loss of Retinal Function;" U.S. application Ser. No. 14/644,107 filed on Mar. 10, 2015, titled 'Piggyback Intraocular Lens that Improves Overall Vision where there is a Local Loss of Retinal Function;" and U.S. application Ser. No. 14/644,082 filed on Mar. 10, 2015, titled 'Intraocular Lens that Improves Overall Vision where there is a Local Loss of Retinal Function." Each of the above-identified application is hereby incorporated by reference herein in its entirety for all that it discloses and is made a part of this application.

Thick Lens

An implementation of a thick lens was designed according to the concepts discussed above to improve peripheral image quality without sacrificing foveal image quality. The implementation of the thick lens has a first surface and a second surface intersected by an optical axis that passes through the geometric center of the thick lens and joins the center of curvatures of the first and second surfaces. FIG. 37A illustrates the surface sag of the first surface on which light from the object is incident. The first surface of the lens can be referred to as an anterior surface which will face the cornea when the lens is implanted in the eye. FIG. 37B illustrates the surface sag of the second surface from which light incident on the lens exits the lens. The second surface of the lens can be referred to as a posterior surface which will face the retina when the lens is implanted in the eye. Both the first and the second surface are higher order aspheric surfaces including up to eighth ($8^{th}$) order aspheric terms. In the particular implementation described herein, the placement of the thick lens in the eye is similar to the standard lens. However, the thickness of the thick lens is increased to 1.5 mm.

The foveal image quality for the implementation of the thick lens can be evaluated using the through-focus MTF at a spatial frequency of 100 cycles/mm in green light for a 5 mm pupil, illustrated in FIG. 37C. As noted from FIG. 37C, the through-focus MTF at a spatial frequency of 100 cycles/mm in green light is about 0.73 indicating sufficient image quality at the fovea. Optical performance of the double aspheric lens at different eccentricities between 0 to 30-degrees in increments of 5 degrees can be deduced from the data provided in Table 7.4 below. With reference to Table 7.4, M is the spherical defocus and J0 is the astigmatic error. It is observed from Table 7.4 that at an eccentricity of about 30-degrees, the implementation of the double aspheric lens has an astigmatic error of −1.19 Diopters and a spherical defocus value of about −0.15 Diopters. The overall figure of merit given by a geometric average of figures of merit obtained at different eccentricities between 5 degrees and 30 degrees in increments of 5 degrees as discussed above for the implementation of thick lens was 0.48 corresponding to an average contrast ratio increase of about 25% as compared to the standard lens.

TABLE 7.4

| Angle | M | J0 |
|---|---|---|
| 0 | −0.02 | 0 |
| 5 | −0.03 | −0.04 |
| 10 | −0.04 | −0.16 |
| 15 | −0.06 | −0.35 |
| 20 | −0.05 | −0.60 |
| 25 | −0.01 | −0.89 |
| 30 | −0.15 | −1.19 |

A comparison of the optical performance of the implementation of the thick lens and the standard lens shows that the implementation of the thick lens configured to improve peripheral image quality has a foveal image quality that is substantially equal to or within a margin of error of the foveal image quality of the standard lens. Additionally, the implementation of the thick lens has a depth of focus, represented by the full width of the through-focus MTF peak at a threshold MTF value (e.g., 0.2, 0.3, 0.4 or 0.5) that is substantially equal to or within a margin of error of the depth of focus provided by the standard lens. Spherical defocus (M) and the astigmatic error (J0) provided by the implementation of the thick lens is lower than the spherical defocus (M) and the astigmatic error (J0) provided by the standard lens. Additionally, the implementation of the thick lens provides about 25% increase in the contrast ratio as compared to the standard lens. Accordingly, the implementation of the thick lens can reduce peripheral refraction errors and improve peripheral image quality without degrading the foveal image quality.

It is further noted from a comparison of the double aspheric lens and the thick lens that while the extra thickness of the thick lens decreases spherical and cylindrical errors, it does not substantially affect the overall figure of merit. Various physical and optical characteristics of the thick lens described herein can be similar to the physical and optical characteristics of the various lenses that are configured to focus obliquely incident light at a peripheral retinal location as described in U.S. application Ser. No. 14/644,101 filed on Mar. 10, 2015, titled 'Dual-Optic Intraocular Lens that Improves Overall Vision where there is a Local Loss of Retinal Function;" U.S. application Ser. No. 14/644,110 filed on Mar. 10, 2015, titled 'Enhanced Toric Lens that Improves Overall Vision where there is a Local Loss of Retinal Function," U.S. application Ser. No. 14/644,107 filed on Mar. 10, 2015, titled 'Piggyback Intraocular Lens that Improves Overall Vision where there is a Local Loss of Retinal Function;" and U.S. application Ser. No. 14/644,082 filed on Mar. 10, 2015, titled 'Intraocular Lens that Improves Overall Vision where there is a Local Loss of Retinal Function." Each of the above-identified application is hereby incorporated by reference herein in its entirety for all that it discloses and is made a part of this application.

Shifted or (Moved) Aspheric Lens

As discussed above, the implementations of lenses discussed above can be implanted in the eye such that the distance between the pupil and the anterior surface of the lens is small. For example, the implementation of lenses disclosed above can be implanted such that the distance between the pupil and the anterior surface of the lens is between 0.9 mm and 1.5 mm. However, it is also conceived that the implementations of the lens discussed above can be implanted as far back in the eye as possible. For example, in some implementations, the lens can be implanted such that it is still in the capsular bag but is closer to the retina. In such implementations, the distance between the pupil and the anterior surface of the lens can be between distance between 1.5 mm and 3.2 mm. As discussed above, axially displacing the lens can modify the principal plane of the lens which in turn can affect the peripheral aberrations. Accordingly, parameters (e.g., the asphericity) of the various surfaces of an aspheric lens can change if the lens is placed closer to the retina. The surface profiles of an aspheric lens that is placed closer to the retina that would reduce peripheral aberrations can be obtained using the stop-shift equations described above. The surface profiles of an aspheric lens that is configured to be placed at a distance of about 2 mm from the position of the standard lens when implanted is shown in FIGS. 38A and 38B. The implementation of the shifted aspheric lens was designed according to the concepts discussed above to improve peripheral image quality without sacrificing foveal image quality. FIG. 38A illustrates the surface sag of the first surface on which light from the object is incident also referred to as the anterior surface and FIG. 38B illustrates the surface sag of the second surface from which light incident on the lens exits the lens also referred to as the posterior surface. Both the first and the second surface are configured as higher order aspheric surfaces including up to tenth ($10^{th}$) order aspheric terms. In the particular implementation described herein, the thickness of the aspheric lens is similar to the standard lens. However, the aspheric lens is displaced by about 2.0 mm towards the retina when implanted in the eye as compared to the standard lens.

The foveal image quality for the implementation of the shifted aspheric lens can be evaluated using the through-focus MTF at a spatial frequency of 100 cycles/mm in green light for a 5 mm pupil, illustrated in FIG. 38C. As noted from FIG. 38C, the through-focus MTF at a spatial frequency of 100 cycles/mm in green light is about 0.73 indicating sufficient image quality at the fovea. Optical performance of the double aspheric lens at different eccentricities between 0 to 30-degrees in increments of 5 degrees can be deduced from the data provided in Table 7.5 below. With reference to Table 7.5, M is the spherical defocus and J0 is the astigmatic error. It is observed from Table 7.5 that at an eccentricity of about 30-degrees, the implementation of the double aspheric lens has an astigmatic error of −1.87 Diopters and a spherical defocus value of about −0.75. The overall figure of merit given by a geometric average of figures of merit obtained at different eccentricities between 5 degrees and 30 degrees in increments of 5 degrees as discussed above for the implementation of shifted aspheric lens was 0.56 corresponding to an average contrast ratio increase of about 40% as compared to the standard lens.

TABLE 7.5

| Angle | M | J0 |
|---|---|---|
| 0 | −0.01 | 0 |
| 5 | 0 | −0.03 |
| 10 | 0.02 | −0.12 |
| 15 | 0.06 | −0.28 |
| 20 | 0.08 | −0.52 |

TABLE 7.5-continued

| Angle | M | J0 |
|---|---|---|
| 25 | −0.05 | −0.94 |
| 30 | −0.75 | −1.87 |

A comparison of the optical performance of the implementation of the thick lens and the standard lens shows that the implementation of the shifted aspheric lens configured to improve peripheral image quality has a foveal image quality that is substantially equal to or within a margin of error of the foveal image quality of the standard lens. Additionally, the implementation of the thick lens has a depth of focus, represented by the full width of the through-focus MTF peak at a threshold MTF value (e.g., 0.2, 0.3, 0.4 or 0.5) that is substantially equal to or within a margin of error of the depth of focus provided by the standard lens. The shifted aspheric lens provides some reduction in the spherical defocus (M) over the standard lens but does not provide significant improvement in the astigmatic error (J0) over the standard lens. Additionally, the implementation of the shifted aspheric lens provides about 50% increase in the contrast ratio as compared to the standard lens. Accordingly, the implementation of the shifted aspheric lens can reduce peripheral refraction errors and improve peripheral image quality without degrading the foveal image quality. Various physical and optical characteristics of the shifted aspheric lens described herein can be similar to the physical and optical characteristics of the various lenses that are configured to focus obliquely incident light at a peripheral retinal location as described in U.S. application Ser. No. 14/644,101 filed on Mar. 10, 2015, titled 'Dual-Optic Intraocular Lens that Improves Overall Vision where there is a Local Loss of Retinal Function;" U.S. application Ser. No. 14/644,110 filed on Mar. 10, 2015, titled 'Enhanced Toric Lens that Improves Overall Vision where there is a Local Loss of Retinal Function;" U.S. application Ser. No. 14/644,107 filed on Mar. 10, 2015, titled 'Piggyback Intraocular Lens that Improves Overall Vision where there is a Local Loss of Retinal Function;" and U.S. application Ser. No. 14/644,082 filed on Mar. 10, 2015, titled 'Intraocular Lens that Improves Overall Vision where there is a Local Loss of Retinal Function." Each of the above-identified application is hereby incorporated by reference herein in its entirety for all that it discloses and is made a part of this application.

Dual Optic Lens

An implementation of a dual optic aspheric lens was designed according to the concepts discussed above to improve peripheral image quality without sacrificing foveal image quality. The implementation of the dual optic lens includes two optics that are separated from each other by a distance of 1.5 mm. The distance between the two optics of the dual optic lens is fixed in the particular implementation described herein. Each optic of the dual optic lens has a first surface and a second surface intersected by an optical axis that passes through the geometric center of the lens and joins the center of curvatures of the first and second surfaces. The optical axis of each of the two optics can coincide with each other, be tilted with respect to each other or be offset from each other. FIG. 39A illustrates the surface sag of the first surface of the first optic of the dual optic lens, the first surface of the first optic can be the surface on which light from the object is incident and can be referred to as an anterior surface which will face the cornea when the dual optic lens is implanted in the eye. FIG. 39B illustrates the surface sag of the second surface of the first optic of the dual optic lens from which light exits the first optic. FIG. 39C illustrates the surface sag of the first surface of the second optic of the dual optic lens which receives light that exits the first optic. FIG. 39D illustrates the surface sag of the second surface of the second optic of the dual optic lens from which light exits the dual optic lens. The second surface of the second optic can be referred to as a posterior surface which will face the retina when the dual optic lens is implanted in the eye. The first and the second surfaces of the first and second optics can be aspheric surfaces including up to eighth ($8^{th}$) order aspheric terms. In the particular implementation described herein, the thickness of the first optic is 0.557 mm and the thickness of the second optic is 0.916 mm.

The foveal image quality for the implementation of the dual optic lens can be evaluated using the through-focus MTF at a spatial frequency of 100 cycles/mm in green light for a 5 mm pupil, illustrated in FIG. 39C. As noted from FIG. 39C, the through-focus MTF at a spatial frequency of 100 cycles/mm in green light is about 0.74 indicating sufficient image quality at the fovea. Optical performance of the dual optic lens at different eccentricities between 0 to 30-degrees in increments of 5 degrees can be deduced from the data provided in Table 7.6 below. With reference to Table 7.6, M is the spherical defocus and J0 is the astigmatic error. It is observed from Table 7.6 that at an eccentricity of about 30-degrees, the implementation of the double aspheric lens has an astigmatic error of −0.66 Diopters and a spherical defocus value of about −1.03 Diopters. The overall figure of merit given by a geometric average of figures of merit obtained at different eccentricities between 5 degrees and 30 degrees in increments of 5 degrees as discussed above for the implementation of the dual optic lens was 0.56 corresponding to an average contrast ratio increase of about 40% as compared to the standard lens.

TABLE 7.6

| Angle | M | J0 |
|---|---|---|
| 0 | 0.01 | 0 |
| 5 | 0.05 | −0.03 |
| 10 | 0.07 | −0.10 |
| 15 | 0.17 | −0.22 |
| 20 | 0.33 | −0.39 |
| 25 | 0.58 | −0.55 |
| 30 | 1.03 | −0.66 |

A comparison of the optical performance of the implementation of the dual optic lens and the standard lens shows that the implementation of the dual optic lens configured to improve peripheral image quality has a foveal image quality that is substantially equal to or within a margin of error of the foveal image quality of the standard lens. Additionally, the implementation of the dual optic lens has a depth of focus, represented by the full width of the through-focus MTF peak at a threshold MTF value (e.g., 0.2, 0.3, 0.4 or 0.5) that is substantially equal to or within a margin of error of the depth of focus provided by the standard lens. Spherical defocus (M) and the astigmatic error (J0) provided by the implementation of the dual optic lens is lower than the spherical defocus (M) and the astigmatic error (J0) provided by the standard lens. Additionally, the implementation of the dual optic lens provides about 50% increase in the contrast ratio as compared to the standard lens. Accordingly, the implementation of the dual optic lens can reduce peripheral refraction errors and improve peripheral image quality without degrading the foveal image quality. Various physical and optical characteristics of the dual optic lens described herein can be similar to the physical and optical characteristics of the various lenses that are configured to focus obliquely incident light at a peripheral retinal location as described in U.S. application Ser. No. 14/644,101 filed on Mar. 10, 2015, now U.S. Pat. No. 9,579,192, titled 'Dual-Optic Intraocular Lens that Improves Overall Vision where there is a Local Loss of Retinal Function;" U.S. application Ser. No. 14/644,110 filed on Mar. 10, 2015, now U.S. Pat. No. 9,636,215, titled 'Enhanced Toric Lens that Improves Overall Vision where there is a Local Loss of Retinal Function;" U.S. application Ser. No. 14/644,107 filed on Mar. 10, 2015, now U.S. Pat. No. 10,136,990, titled 'Piggyback Intraocular Lens that Improves Overall Vision where there is a Local Loss of Retinal Function;" and U.S. application Ser. No. 14/644,082 filed on Mar. 10, 2015, now U.S. Pat. No. 9,867,693, titled 'Intraocular Lens that Improves Overall Vision where there is a Local Loss of Retinal Function." Each of the above-identified application is hereby incorporated by reference herein in its entirety for all that it discloses and is made a part of this application.

Accommodating Dual Optic Lens

An implementation of an accommodating dual optic lens was designed according to the concepts discussed above to improve peripheral image quality without sacrificing foveal image quality. Without any loss of generality, an IOL that is configured to change the axial position of the optic and/or shape and size of the optic in response to ocular forces applied by the capsular bag and/or ciliary muscles can be referred to as an accommodating lens. The implementation of the accommodating dual optic lens includes two optics that are separated from each other by a variable distance. The distance between the two optics of the accommodating dual optic lens can be varied in response to ocular forces exerted by the capsular bag, the zonules and/or the cillary muscles. The dual optic lens can be configured to provide up to about 1.0 Diopter of additional optical power when the distance between the two optics is varied.

Each optic of the dual optic lens has a first surface and a second surface intersected by an optical axis that passes through the geometric center of the lens and joins the center of curvatures of the first and second surfaces. The optical axis of each of the two optics can coincide with each other, be tilted with respect to each other or be offset from each other. In the particular implementation described herein, a first optic of the accommodating dual optic lens which is configured to receive incident light from the object (also referred to as an anterior optic) can be a spherical lens having an optical power of about 25 Diopter. In the particular implementation described herein, a second optic of the accommodating dual optic lens from which light exits the dual optic lens (also referred to as a posterior optic) includes two aspheric surfaces. The surfaces of the posterior optic can include up to eighth ($8^{th}$) order aspheric terms. In the particular implementation described herein, the thickness of the first and the second optic is about 0.9 mm. Various physical and optical characteristics of the accommodating dual optic lens described herein can be similar to the physical and optical characteristics of the various lenses that are configured to focus obliquely incident light at a peripheral retinal location as described in U.S. application Ser. No. 14/644,101 filed on Mar. 10, 2015, titled 'Dual-Optic Intraocular Lens that Improves Overall Vision where there is a Local Loss of Retinal Function;" U.S. application Ser. No. 14/644,110 filed on Mar. 10, 2015, titled 'Enhanced Toric Lens that Improves Overall Vision where there is a Local Loss of Retinal Function;" U.S. application Ser. No. 14/644,107 filed on Mar. 10, 2015, titled 'Piggyback Intraocular Lens that Improves Overall Vision where there is a Local Loss of Retinal Function;" and U.S. application Ser. No. 14/644,082 filed on Mar. 10, 2015, titled 'Intraocular Lens that Improves Overall Vision where there is a Local Loss of Retinal Function." Each of the above-identified application is hereby incorporated by reference herein in its entirety for all that it discloses and is made a part of this application.

FIG. 40A illustrates the surface sag of the first surface of the first optic of the dual optic lens, the first surface of the first optic can be the surface on which light from the object is incident and can be referred to as an anterior surface which will face the cornea when the dual optic lens is implanted in the eye. FIG. 40B illustrates the surface sag of the second surface of the first optic of the dual optic lens from which light exits the first optic. FIG. 40C illustrates the surface sag of the first surface of the second optic of the dual optic lens which receives light that exits the first optic. FIG. 40D illustrates the surface sag of the second surface of the second optic of the dual optic lens from which light exits the dual optic lens. The second surface of the second optic can be referred to as a posterior surface which will face the retina when the dual optic lens is implanted in the eye.

The foveal image quality for the implementation of the accommodating dual optic lens can be evaluated using the through-focus MTF at a spatial frequency of 100 cycles/mm in green light for a 5 mm pupil, illustrated in FIG. 40C. As noted from FIG. 40C, the through-focus MTF at a spatial frequency of 100 cycles/mm in green light is about 0.57 which is lesser than the MTF of the standard lens described above. However, the MTF of the accommodating dual optic lens at a spatial frequency of 100 cycles/mm in green light is similar to the MTF achieved by a standard spherical lens having accommodating capabilities.

Optical performance of the dual optic lens at different eccentricities between 0 to 30-degrees in increments of 5 degrees can be deduced from the data provided in Table 7.7 below. With reference to Table 7.7, M is the spherical defocus and J0 is the astigmatic error. It is observed from Table 7.7 that at an eccentricity of about 30-degrees, the implementation of the double aspheric lens has an astigmatic error of −13.7 Diopters and a spherical defocus value of about −21.15 Diopters. Although, the refractive errors are larger as compared to the standard lens, the overall figure of merit given by a geometric average of figures of merit obtained at different eccentricities between 5 degrees and 30 degrees in increments of 5 degrees as discussed above for the implementation of the accommodating dual optic lens was 0.53 corresponding to an average contrast ratio increase of about 40% as compared to the standard lens.

TABLE 7.7

| Angle | M | J0 |
| --- | --- | --- |
| 0 | −0.13 | 0 |
| 5 | −0.29 | 0.12 |
| 10 | −0.92 | −0.56 |
| 15 | −0.246 | −1.63 |
| 20 | −5.61 | −3.73 |
| 25 | −11.36 | −7.47 |
| 30 | −21.15 | −13.70 |

Summary of Various Optical Lens Designs

The peripheral and the foveal image quality for the various lens designs discussed above are summarized in Tables 7.8 and 7.9 below. Table 7.8 provides the summary of the optical performance for a 5 mm pupil and table 7.9 provides the summary of the optical performance for a 3 mm pupil. As discussed above, the various lens designs represent different optical surface configurations that through the use of optimization algorithms and metrics, as described above, are configured to provide improved peripheral image quality. From Tables 7.8 and 7.9, it is noted that the different lens designs with the exception of the meniscus lens design, gives a figure of merit increase corresponding to an average MTF gain in a peripheral image between about 25%-50% as compared to the standard lens, with the more complex designs providing a higher MTF gain. It is also noted that it is advantageous to use MTF based metrics to evaluate the peripheral image quality instead of the optical errors (e.g., spherical defocus or astigmatic error) in the peripheral image. For example, although the meniscus lens design significantly reduced optical errors in the peripheral image as compared to the standard lens, the overall figure of merit for the meniscus lens design was equal to the overall figure of merit of the standard lens. The lack of improvement in the overall MTF of the meniscus lens design can be attributed to a combination of higher order aberrations. As another example, the accommodating dual optic lens had a higher overall figure of merit as compared to the standard lens despite having large optical errors.

TABLE 7.8

Optical Performance of Various Lens designs for 5 mm pupil

| Design | Overall Figure of merit | Foveal MTF 100 c/mm |
|---|---|---|
| Standard lens | 0.40 | 0.76 |
| Meniscus lens | 0.41 | 0.75 |
| Double aspheric lens | 0.50 | 0.74 |
| Thick lens | 0.48 | 0.73 |
| Shifted aspheric lens | 0.56 | 0.72 |
| Dual optic lens | 0.56 | 0.74 |
| Accommodating Dual optic lens | 0.53 | 0.57 |

TABLE 7.9

Optical Performance of Various Lens designs for 3 mm pupil

| Design | Overall Figure of merit | Foveal MTF 100 c/mm |
|---|---|---|
| Standard lens | 0.44 | 0.61 |
| Meniscus lens | 0.61 | 0.59 |
| Double aspheric lens | 0.66 | 0.61 |
| Thick lens | 0.70 | 0.61 |
| Shifted aspheric lens | 0.69 | 0.60 |
| Dual optic lens | 0.68 | 0.62 |
| Accommodating Dual optic lens | 0.67 | 0.61 |

A comparison of the optical performance of the different lens designs in bright conditions (pupil size of 3 mm) tabulated in Table 7.9 indicates that the overall figures of merits are increased for the different lens designs as compared to the standard lens whereas the foveal MTF remains substantially equal to the foveal MTF provided by the standard lens. It is further noted that the optical performance of the thick lens thickness is comparable to the optical performance of the other lens designs. Furthermore, the meniscus lens has a higher overall figure of merit as compared to the overall figure of merit of the standard lens since higher order aberrations introduced by the meniscus less are less relevant when the pupil size is small. It is also observed that the foveal image quality of the accommodating dual optic lens is comparable to the other lens designs.

The various lens designs discussed above can be implemented in an IOL including an optic having surfaces similar to the surface profiles described above and an haptic that holds the IOL in place when implanted in the eye. The haptic can comprise a biocompatible material that is suitable to engage the capsular bag of the eye, the iris, the sulcus and/or the ciliary muscles of the eye. For example, the haptic can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrene, polyurethanes, hydrogels, etc. In various implementations, the haptic can include a one or more arms that are coupled to the optic of the IOL. For example, the haptic can be configured to have a structure similar to the structure of the biasing elements disclosed in U.S. Publication No. 2013/0013060 which is incorporated by reference herein in its entirety. In various implementations, the haptic can include one or more arms that protrude into the optic. In various implementations, the haptic can be configured to move the optic along the optical axis of the eye in response to ocular forces applied by the capsular bag and/or the ciliary muscles. For example, the haptic can include one or more hinges to facilitate axial movement of the optic. As another example, the haptic can include springs or be configured to be spring-like to effect movement of the optic. In this manner, the axial position of the optic can be varied in response to ocular forces to provide vision over a wide range of distances. In various implementations, the haptic can also be configured to change a shape of the optic in response to ocular forces. As discussed above, varying the axial position of the optic or the shape of the optic can shift the principal plane which can affect (e.g., reduce) one or more peripheral optical aberrations. Thus, the haptic can be configured to reduce at least one optical aberration in an image formed at a peripheral retinal location.

The optic of the lens can be configured such that the refractive properties of the optic can be changed in response to the eye's natural process of accommodation. For example, the optic can comprise a deformable material that can compress or expand in response to ocular forces applied by the capsular bag and/or the ciliary muscles. As another example, the optic can be configured to change their shape in response to ocular forces in the range between about 1 gram to about 10 grams, 5 to 10 grams, 1 to 5 grams, about 1 to 3 grams or values therebetween to provide an optical power change between about 0.5 Diopters and about 6.0 Diopters. In various implementations, the optic can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrenes, polyurethanes, hydrogels, etc. The optic can comprise structures and materials that are described in U.S. Publication No. 2013/0013060 which is incorporated by reference herein in its entirety.

The lens designs discussed above can be configured such that light incident on the cornea parallel to the optical axis of the eye is focused on the central portion of the retina so as to produce a functional foveal image having sufficient image quality. For example, the foveal image can have a MTF of at least 0.5 at a spatial frequency greater than or equal to 50 cycles/mm in green light for a pupil size of 3-5 mm. Additionally, light incident at oblique angles from is focused at a location of the peripheral retina away from the fovea so as to produce a functional peripheral image with sufficient image quality. The light can be incident obliquely from the vertical field of view or the horizontal field of view. For example, the implementations of lenses discussed herein can be configured to focus light incident at oblique angles between about 5 degrees and about 30 degrees with respect to the optical axis of the eye, between about 10 degrees and about 25 degrees with respect to the optical axis of the eye, between about 15 degrees and about 20 degrees with respect to the optical axis of the eye, or there between at a location on the peripheral retina away from the fovea. Additionally, the lenses discussed herein can also be configured to accommodate to focus objects located at different distances on to the retina (e.g., at a location on the periphery of the retina and/or the fovea) in response to ocular forces exerted by the capsular bag and/or ciliary muscles. Portions of the first or second surface of the lenses described above can be toric so as to provide corneal astigmatic correction. The first or the second surface of the lenses described above can include diffractive features to provide a larger depth of field. The first or the second surface of the lenses described above can include extra apertures to further enhance peripheral image quality. The first or the second surface of the lenses described above can include asymmetric parts to selectively improve parts of the visual field. For example as discussed above, the first or second surface of the lenses described above can include a toric component having a higher optical power along the vertical axis corresponding to an axis of 90-degrees using the common negative cylinder sign convention than the horizontal axis corresponding to an axis of 180-degrees using the common negative cylinder sign convention. Such a lens can improve image quality in the horizontal field of view which can be beneficial to patients, as most relevant visual tasks are carried out in the horizontal field of view. The various lens designs discussed above can be implemented as add-on lenses to existing IOLs to improve peripheral image quality of existing IOLs.

The implementations of lenses described in this disclosure can be configured to correct lower order errors (e.g. sphere and cylinder), higher order aberrations (e.g., coma, trefoil) or both resulting from the oblique incidence of light in the image formed at a location of the peripheral retina. The geometry of the various surfaces of the lenses described in this disclosure, the thickness of the lenses described in this disclosure, the placement of the various implementations of lenses described in this disclosure and other parameters can be configured such that the lenses can focus light incident parallel to the optical axis at the fovea with sufficient visual contrast and light incident at a plurality of oblique angles (e.g., between about −25 degree and about +25 degrees with respect to the optical axis of the eye) in an area around a location on the peripheral retina spaced away from the fovea with sufficient visual contrast. The various lens designs discussed above can be implemented as an add-on lens to improve image quality at a peripheral location by reducing one or more optical aberrations at the peripheral location in patients who have been fitted with a standard intraocular lens currently available in the market.

Example Method of Designing an IOL to Compensate for Peripheral Aberrations

An example method of designing an IOL to compensate for peripheral aberrations is illustrated in FIG. 41. The method 3000 includes obtaining ocular measurements for a patient as shown in block 3005. The ocular measurements can be obtained using a COAS and any biometer which is currently available in ophthalmology practice. The ocular measurements can include obtaining axial length of the eye, corneal power and the spherical power that achieves emmetropia. The ocular measurements can include obtaining the variation of the peripheral astigmatism, horizontal coma and spherical optical power as a function of visual field angle.

The method 3000 is configured to determine an IOL design including a plurality of optical features that compensates for peripheral astigmatism, horizontal coma and peripheral defocus as shown in the block 3025. The plurality of optical features can include one or more optical elements (e.g., focusing elements, diffracting elements), grooves, volume or surface diffractive features, etc. In various embodiments, the plurality of optical features can include regions of varying refractive index and/or regions with varying curvatures. In various embodiments, some of the plurality of optical features can be arranged regularly to form a pattern. In various embodiments, some of the plurality of optical features can be arranged in a random manner. The plurality of optical features can include or be based on a first set of optical features configured to compensate for peripheral astigmatism as shown in block 3010, a second set of optical features configured to compensate for horizontal coma, as shown in block 3015 and a third set of optical features configured to compensate for peripheral defocus as shown in block 3020.

As discussed above, peripheral astigmatism is independent of the patient's biometric inputs. Accordingly, the determination of the first set of optical features that result in an optical power distribution that corrects for peripheral astigmatism can be independent of the patient's biometric inputs. In various embodiments, the arrangement of the first set of optical features can provide greater cylinder power in the peripheral regions at visual field angles having an absolute value greater than about 10 degrees as compared to the cylinder power provided in the central region at visual field angles between about −10 degrees and about +10 degrees. In various embodiments, the arrangement of the first set of optical features can provide cylinder power that continuously increases from the central region to the peripheral regions such that peripheral astigmatism is compensated at most or all visual field angles. This variation can be nonlinear in different embodiments. For example, in various embodiments, the cylinder power resulting from the arrangement of the first set of optical features can increase quadratically from the central region to the peripheral regions. In some embodiments, the arrangement of the first set of optical features can provide additional cylinder power that compensates for peripheral astigmatism only at certain specific visual field angles (e.g., ±15 degrees, ±20 degrees, ±25 degrees, ±30 degrees).

As discussed above, horizontal coma is independent of the patient's biometric inputs. Accordingly, the determination of the second set of optical features that results in an optical power distribution that corrects for horizontal coma can be independent of the patient's biometric inputs. In various embodiments, the amount of horizontal coma provided by the arrangement of the second set of optical features can decrease linearly from positive values at a visual field angle of about −40 degrees to negative values at a visual field angle of about +40 degrees. In various embodiments, the arrangement of the second set of optical features can provide a horizontal coma value that varies continuously (e.g., increasing for right eyes and decreasing for left eyes) from the temporal peripheral region to the nasal temporal region such that horizontal coma is compensated at most or all visual field angles. Alternately, in some embodiments, the IOL can be configured to compensate for horizontal coma only at certain specific visual field angles (e.g., ±15 degrees, ±20 degrees, ±25 degrees, ±30 degrees).

As discussed above, peripheral defocus is related to a patient's biometric inputs, such as, for example, axial length and corneal power. Since, these parameters are also used to calculate the spherical power of an IOL, IOLs configured to correct peripheral defocus also depend on the foveal refractive state or the IOL spherical power to achieve emmetropia. In various embodiments of an IOL configured to compensate for peripheral defocus in an emmetropic eye or in patients with low amounts of myopia, the arrangement of the third set of optical features can provide greater amount of optical defocus in the peripheral regions as compared to the central region. In various embodiments of an IOL configured to compensate for peripheral defocus, in patients with moderate to high amounts of myopia, the arrangement of the third set of optical features can provide lesser amount of optical defocus in the peripheral regions as compared to the central region. In various embodiments, the arrangement of the third set of optical features can result in an optical power distribution that is symmetric about the central region. In various embodiments, the the arrangement of the third set of optical features can result in an optical power distribution that is nonlinear with eccentricity. In various embodiments, the arrangement of the third set of optical features can result in an optical power distribution that varies continuously from the central region to the peripheral regions such that defocus is compensated at most or all visual field angles. Alternately, in some embodiments, the arrangement of the third set of optical features can be configured to compensate for defocus only at certain specific visual field angles (e.g., ±15 degrees, ±20 degrees, ±25 degrees, ±30 degrees). The various operations illustrated in method 3000 can be performed sequentially or simultaneously. In various embodiments, the first, second and third sets of optical features can be disposed on an IOL having a base optical power. In various embodiments, the IOL can be designed considering the variation of the peripheral astigmatism, peripheral defocus and horizontal coma with respect to field of view simultaneously. In various embodiments, the method 3000 can be iterative wherein the operations in blocks 3010, 3015, 3020 and 3025 can be repeated several times to obtain an optimized IOL power distribution that corrects for peripheral errors, such as, for example, peripheral astigmatism, horizontal coma and peripheral defocus.

Referring to FIG. 42, in certain embodiments, a method 200 for optimizing peripheral vision comprises an element 205 of determining one or more physical and/or optical properties of the eye 100 including a geographical map of retinal functionality and/or the retinal shape.

The method 200 additionally comprises an element 210 of either designing or determining the type of intraocular lens 100 suitable for optimizing visual acuity, including peripheral visual acuity. The design of the lens may be of any detailed herein, as well as modifications and alternate constructions that are apparent to a person having ordinary skill in the art.

The method 200 also comprises an element 215 of calculating a desired position of the intraocular lens 100 or the optic 102 after an ocular surgical procedure.

Referring to FIG. 43, in certain embodiments, a computer system 300 for improving or optimizing peripheral vision comprises a processor 302 and a computer readable memory 304 coupled to the processor 302. The computer readable memory 304 has stored therein an array of ordered values 308 and sequences of instructions 310 which, when executed by the processor 302, cause the processor 302 to perform certain functions or execute certain modules. For example, a module can be executed that is configured to calculate a postoperative lens position within an eye and/or for selecting an ophthalmic lens or an optical power thereof. As another example, a module can be executed that is configured to perform one or more of the steps in method 1700, 2200, 3100, 3000 or 200 as described with reference to FIGS. 17, 22, 31, 41 and 42 respectively. As another example, a module can be executed that is configured to determine an improved or optimal IOL design through the evaluation of aberrations after a shift in the relative positions of a stop and a lens, by using the stop-shift equations as described herein. As another example, a module can be executed which is configured to determine binocular IOL properties for improving peripheral contrast sensitivity. As another example, a module can be executed which is configured to determine an optical correction which is provided to increase contrast sensitivity along the horizontal direction which can include corrections for astigmatism and other spherical and/or non-spherical aberrations.

The array of ordered values 308 may comprise, for example, one or more ocular dimensions of an eye or plurality of eyes from a database, a desired refractive outcome, parameters of an eye model based on one or more characteristics of at least one eye, and data related to an IOL or set of IOLs such as a power, an aspheric profile, and/or a lens plane. In some embodiments, the sequence of instructions 310 includes determining a position of an IOL, performing one or more calculations to determine a predicted refractive outcome based on an eye model and a ray tracing algorithm, comparing a predicted refractive outcome to a desired refractive outcome, and based on the comparison, repeating the calculation with an IOL having at least one of a different power, different design, and/or a different IOL location.

The computer system 300 may be a general purpose desktop or laptop computer or may comprise hardware specifically configured performing the desired calculations. In some embodiments, the computer system 300 is configured to be electronically coupled to another device such as a phacoemulsification console or one or more instruments for obtaining measurements of an eye or a plurality of eyes. In other embodiments, the computer system 300 is a handheld device that may be adapted to be electronically coupled to one of the devices just listed. In yet other embodiments, the computer system 300 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions of the system 300 will include elements of the method 200, 1700, 2200, 3000, 3100 and/or parameters and routines for performing calculations of one or more of Equations above, such as the stop-shift equations or the metrics.

In certain embodiments, the system 300 includes or is part a phacoemulsification system, laser treatment system, optical diagnostic instrument (e.g, autorefractor, aberrometer, and/or corneal topographer, or the like). For example, the computer readable memory 304 may additionally contain instructions for controlling the handpiece of a phacoemulsification system or similar surgical system. Additionally or alternatively, the computer readable memory 304 may additionally contain instructions for controlling or exchanging data with an autorefractor, aberrometer, tomographer, and/or topographer, or the like.

In some embodiments, the system 300 includes or is part of a refractive planner. The refractive planner may be a system for determining one or more treatment options for a subject based on such parameters as patient age, family history, vision preferences (e.g., near, intermediate, distant vision), activity type/level, past surgical procedures.

CONCLUSION

The above presents a description of the best mode contemplated of carrying out the concepts disclosed herein, and of the manner and process of making and using it, in such full, clear, concise, and exact terms as to enable any person skilled in the art to which it pertains to make and use the concepts described herein. The systems, methods and devices disclosed herein are, however, susceptible to modifications and alternate constructions from that discussed above which are fully equivalent. Consequently, it is not the intention to limit the scope of this disclosure to the particular embodiments disclosed. On the contrary, the intention is to cover modifications and alternate constructions coming within the spirit and scope of the present disclosure as generally expressed by the following claims, which particularly point out and distinctly claim the subject matter of the implementations described herein.

Although embodiments have been described and pictured in an example form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

As used herein, the term "processor" refers broadly to any suitable device, logical block, module, circuit, or combination of elements for executing instructions. For example, the processor 302 can include any conventional general purpose single- or multi-chip microprocessor such as a Pentium® processor, a MIPS® processor, a Power PC® processor, AMD® processor, ARM processor, or an ALPHA® processor. In addition, the processor 302 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Processor 302 can be implemented as a combination of computing devices, e.g., a combination of a DSP and a microprocessor, a plurality of microprocessors, one or more microprocessors in conjunction with a DSP core, or any other such configuration.

Computer readable memory 304 can refer to electronic circuitry that allows information, typically computer or digital data, to be stored and retrieved. Computer readable memory 304 can refer to external devices or systems, for example, disk drives or solid state drives. Computer readable memory 304 can also refer to fast semiconductor storage (chips), for example, Random Access Memory (RAM) or various forms of Read Only Memory (ROM), which are directly connected to the communication bus or the processor 302. Other types of memory include bubble memory and core memory. Computer readable memory 304 can be physical hardware configured to store information in a non-transitory medium.

Methods and processes described herein may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

What is claimed is:

1. A method of selecting an intraocular lens (IOL) configured to be implanted in a patient's eye, the method comprising:

obtaining at least one physical or optical characteristic of the patient's eye using a diagnostic instrument; and selecting an IOL having an optic with a shape factor that is configured to focus light incident along a direction parallel to an optical axis at a fovea to produce a functional foveal image and is configured to improve image quality at a peripheral retinal location disposed at a distance from the fovea by reducing at least one optical aberration at the peripheral retinal location, the peripheral retinal location having an eccentricity between 1 and 30 degrees, an object in the central vision zone and an object in the peripheral vision zone defining a visual field angle, wherein the shape factor of the IOL is selected based on the at least one physical or optical characteristic of the patient's eye, and wherein a horizontal coma of the optic varies linearly with visual field angle.

2. The method of claim 1, wherein the shape factor of the IOL is adjusted based by adjusting a parameter of the optic, the parameter selected from the group consisting of a curvature of the first or the second surface, an axial position of the optic with respect to the retina and a thickness of the optic.

3. The method of claim 1, wherein at least one surface of the IOL is aspheric.

4. The method of claim 1, wherein the optic has a modulation transfer function (MTF) of at least 0.5 at a spatial frequency of 100 cycles/mm for both the tangential and the sagittal foci in green light for a pupil size between 3-5 mm.

5. The method of claim 1, wherein an average MTF of the optic obtained for a range of spatial frequencies between 0 cycles/mm and 30 cycles/mm obtained at different eccentricities between 1 and 30 degrees is at least 0.5.

6. The method of claim 1, wherein the at least one optical aberration is selected from the group consisting of defocus, peripheral astigmatism and coma.

7. The method of claim 2, wherein the first or the second surface comprises a plurality of optical features that are configured to reduce the at least one optical aberration.

8. The method of claim 1, wherein the optic is a meniscus lens with a vertex curving inwards from edges of the optic.

9. The method of claim 1, wherein the optic has a thickness between about 0.3 mm and about 2.0 mm.

10. The method of claim 1, further comprising a second optic separated from the optic by a distance.

11. The method of claim 10, wherein the optic is configured to be disposed in the capsular bag of the patient's eye, and the second optic is configured to be disposed between the iris and the patient's eye.

12. The method of claim 10, wherein the optic and the second optic are both configured to be disposed in the capsular bag of the patient's eye.

13. The method of claim 1, wherein horizontal coma of the optic decreases linearly with visual field angle.

14. The method of claim 13, wherein horizontal coma of the optic decreases linearly from a positive value at a visual field angle of −40 degrees to a negative value at a visual field angle of +40 degrees.

* * * * *